(12) United States Patent
Bolchi et al.

(10) Patent No.: US 10,736,954 B2
(45) Date of Patent: Aug. 11, 2020

(54) L2 PEPTIDE IMMUNOGENICITY

(71) Applicant: Deutsches Krebsforschungszentrum, Heidelberg (DE)

(72) Inventors: Angelo Bolchi, Parma (IT); Martin Müller, Neckargemünd (DE); Simone Ottonello, Parma (IT); Somayeh Pouyanfard, Heidelberg (DE); Gloria Spagnoli, Collecchio (IT)

(73) Assignee: Deutsches Krebsforschungzentrum, Heidelberg (DE)

( * ) Notice: Subject to any disclaimer, the term of this patent is extended or adjusted under 35 U.S.C. 154(b) by 0 days.

(21) Appl. No.: 16/308,358

(22) PCT Filed: Jun. 7, 2017

(86) PCT No.: PCT/EP2017/063833
§ 371 (c)(1),
(2) Date: Dec. 7, 2018

(87) PCT Pub. No.: WO2017/211886
PCT Pub. Date: Dec. 14, 2017

(65) Prior Publication Data
US 2019/0125856 A1 May 2, 2019

(30) Foreign Application Priority Data
Jun. 7, 2016 (EP) ..................... 16173313

(51) Int. Cl.
*A61K 39/12* (2006.01)
*C07K 14/025* (2006.01)
*C07K 14/005* (2006.01)
*A61K 39/00* (2006.01)

(52) U.S. Cl.
CPC ............ *A61K 39/12* (2013.01); *C07K 14/005* (2013.01); *A61K 2039/55566* (2013.01); *A61K 2039/55572* (2013.01); *A61K 2039/645* (2013.01); *A61K 2039/70* (2013.01); *C07K 2319/35* (2013.01); *C12N 2710/20022* (2013.01); *C12N 2710/20034* (2013.01)

(58) Field of Classification Search
None
See application file for complete search history.

(56) References Cited

U.S. PATENT DOCUMENTS 9,303,082 B2 * 4/2016 Mueller ............... A61K 39/12

FOREIGN PATENT DOCUMENTS

| WO | 02070004 A2 | 9/2002 |
| WO | 2008140474 A1 | 11/2008 |
| WO | 2009059325 A2 | 5/2009 |
| WO | 2010070052 A2 | 6/2010 |
| WO | 2011151335 A1 | 12/2011 |

OTHER PUBLICATIONS

Jagu et al. Optimization of Multimeric Human Papillomavirus L2 Vaccines. PLoS One , 2013, 8(1): e55538.*
Jagu et al., "Optimization of Multimeric Human Papillomavirus L2 Vaccines," PLOS One, Jan. 2013, vol. 8, No. 1, p. e55538.
Seitz et al., "A three component mix of thioredoxin-L2 antigens elicits broadly neutralizing responses against oncogenic human papillomaviruses," Vaccine, vol. 32 (2014), pp. 2610-2617.
Tyler et al., "Second-Generation Prophylactic HPV Vaccines: Successes and Challenges," Expert Rev Vaccines, Feb. 2014, vol. 13, No. 2, pp. 247-255.
International Searching Authority—European Patent Office, International Search Report and Written Opinion of the International Searching Authority for PCT/EP2017/063833, dated Aug. 3, 2017.
Schmiedeskamp et al.; Human Papillomavirus Vaccines; New Drug Developments; The Annals of Pharmacotherapy; Jul./Aug. 2006; 9 pages; vol. 40; www.theannals.com.
Roden et al.; How Will HPV Vaccines Effect Cervical Cancer?; Nature Reviews; Oct. 2006; 11 pages; vol. 6; © 2006 Nature Publishing Group.
Muller et al.; A Long Way: History of the Prophylactic Papillomavirus Vaccine; Disease Markers; 2007; 7 pages; © 2007 IOS Press and the authors.
Huh et al.; The Future of Vaccines for Cervical Cancer; ScienceDirect/Gynecologic Oncology; 2008; 9 pages; © 2008 Elsevier Inc.
Giroglou et al.; Immunological Analyses of Human Papillomavirus Capsids; Vaccine; 2001; 11 pages; © 2001 Elsevier Science Ltd.
Kondo et al.; Neutralization of HPV16, 18, 31, and 58 Pseudovirions with Antisera Induced by Immunizing Rabbits with Synthetic Peptides Representing Segmets of the HPV16 Minor Capsid Protein L2 Surface Region; ScienceDirect; Virology; 2007; 7 pages; © 2006 Elsevier Inc.
Gambhira et al.; A Protective and Broadly Cross-Neutralizing Epitope of Human Papillomavrus L2; Journal of Virology; Dec. 2007; 5 pages; vol. 81, No. 24; © 2007 American Society for Microbiology.
Yang et al.; Cell Surface-Binding Motifs of L2 That Facilitate Papillomavirus Infection; Journal of Virology; Mar. 2003; 11 pages; © 2003 American Society for Microbiology.
Kawana et al.; Human Papillomavirus Type 16 Minor Capsid Protein L2 N-Terminal Region Containing a Common Neutralization Epitope Binds to the Cell Surface and Enters the Cytoplasm; Journal of Virology; Mar. 2001; 6 pages; © 2001 American Society for Microbiology.

(Continued)

*Primary Examiner* — Nianxiang Zou
(74) *Attorney, Agent, or Firm* — Taft Stettinius & Hollister LLP

(57) ABSTRACT

The present invention relates to an immunogenic polypeptide comprising a multitude of human papillomavirus (HPV) L2 N-terminal peptides corresponding to amino acids 20 to 50 of the L2 polypeptide of HPV16, wherein said HPV L2 N-terminal peptides are L2 N-terminal peptides from at least two different HPV genotypes. The present invention also relates to said immunogenic polypeptide for use in medicine and for use in vaccination against HPV infection. Moreover, the present invention relates to a polynucleotide encoding the immunogenic polypeptide and to a host cell comprising the same. Moreover, the present invention relates to kits, methods, and uses related to the immunogenic polypeptide of the invention.

14 Claims, 24 Drawing Sheets
Specification includes a Sequence Listing.

(56) References Cited

OTHER PUBLICATIONS

Kawana et al.; Nasal Immunization of Mice with Peptide Having a Cross-Neutralization Epitope on Minor Capsid Protein L2 of Human Papillomavirus Type 16 Elicit Systemic and Mucosal Antibodies; Vaccine; 2001; 7 pages; © 2001 Elsevier Science Ltd.

Day et al.; A Human Papillomavirus (HPV) In Vitro Neutralization Assay That Recapitulates the In Vitro Process of Infection Provides a Sensitive Measure of HPV L2 Infection-Inhibiting Antibodies; Clinical and Vaccine Immunology; Jul. 2012; 8 pages; vol. 19 No. 7.

Pastrana et al.; Cross-neutralization of Cutaneous and Mucosal Papillomavirus Types with Anti-sera to the Amino Terminus of L2; Virology; 2005; 8 pages; © 2005 Elsevier Inc.

Canali et al.; A High-Performance Thioredoxin-based Scaffold for Peptide Immunogen Construction; Proof-of-concept Testing with a Human Papillomavirus Epitope; Scientific Reports; Apr. 22, 2014; 11 pages; www.nature.com/scientificreports.

De Villiers et al.; Classification of Papillomaviruses; Virology; 2004; 11 pages; © 2004 Elsevier Inc.

Alphs et al.; Protection Against Heterologous Human Papillomavirus Challenge by a Synthetic Lipopeptide Vaccine Containing a Broadly Cross-Neutralizing Epitope of L2; PNAS; Apr. 15, 2008; 6 pages; vol. 105 No. 15; www.pnas.org/cgi/doi/10.1073/pnas.0800868105.

* cited by examiner

Figure 1:
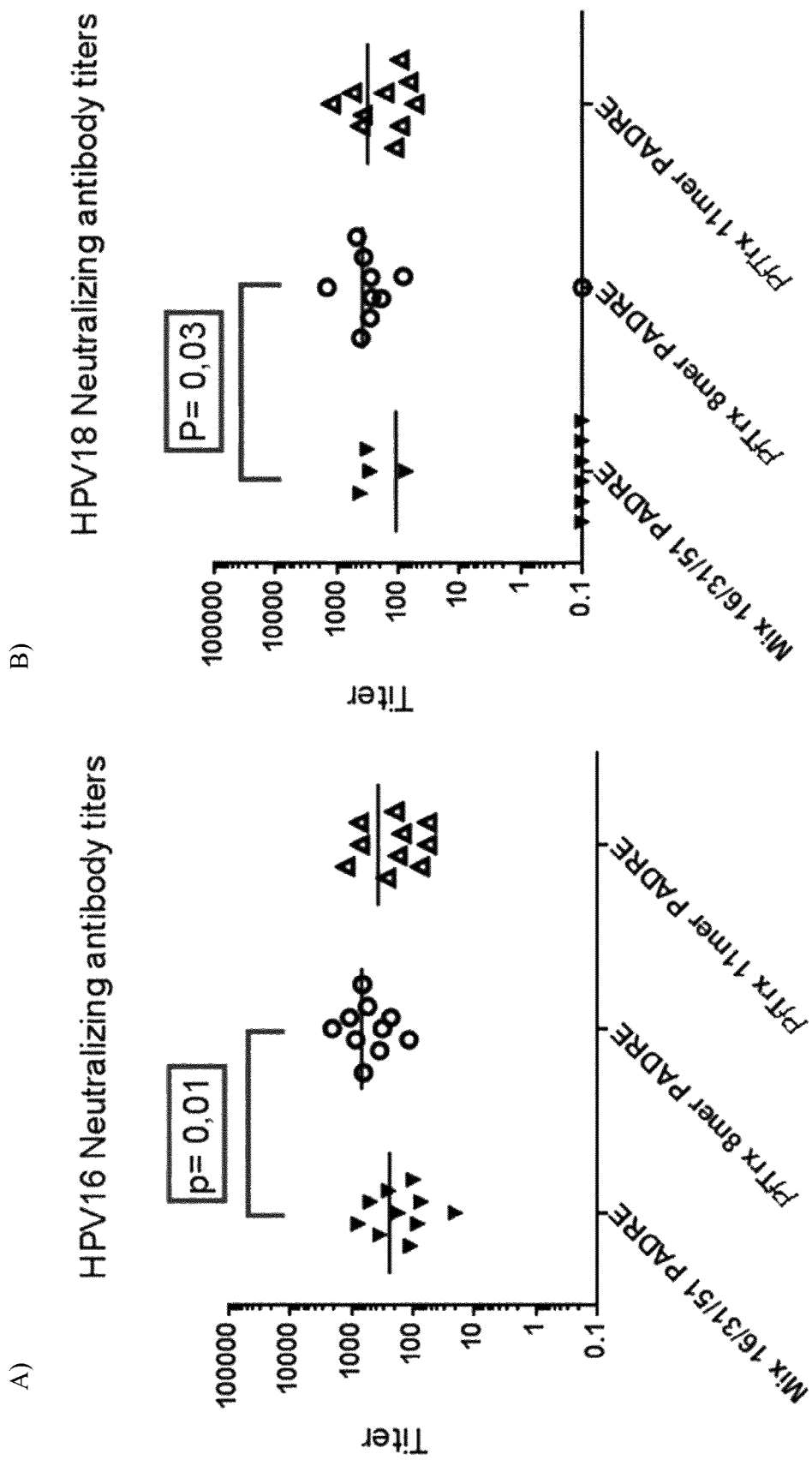
Figure 1:
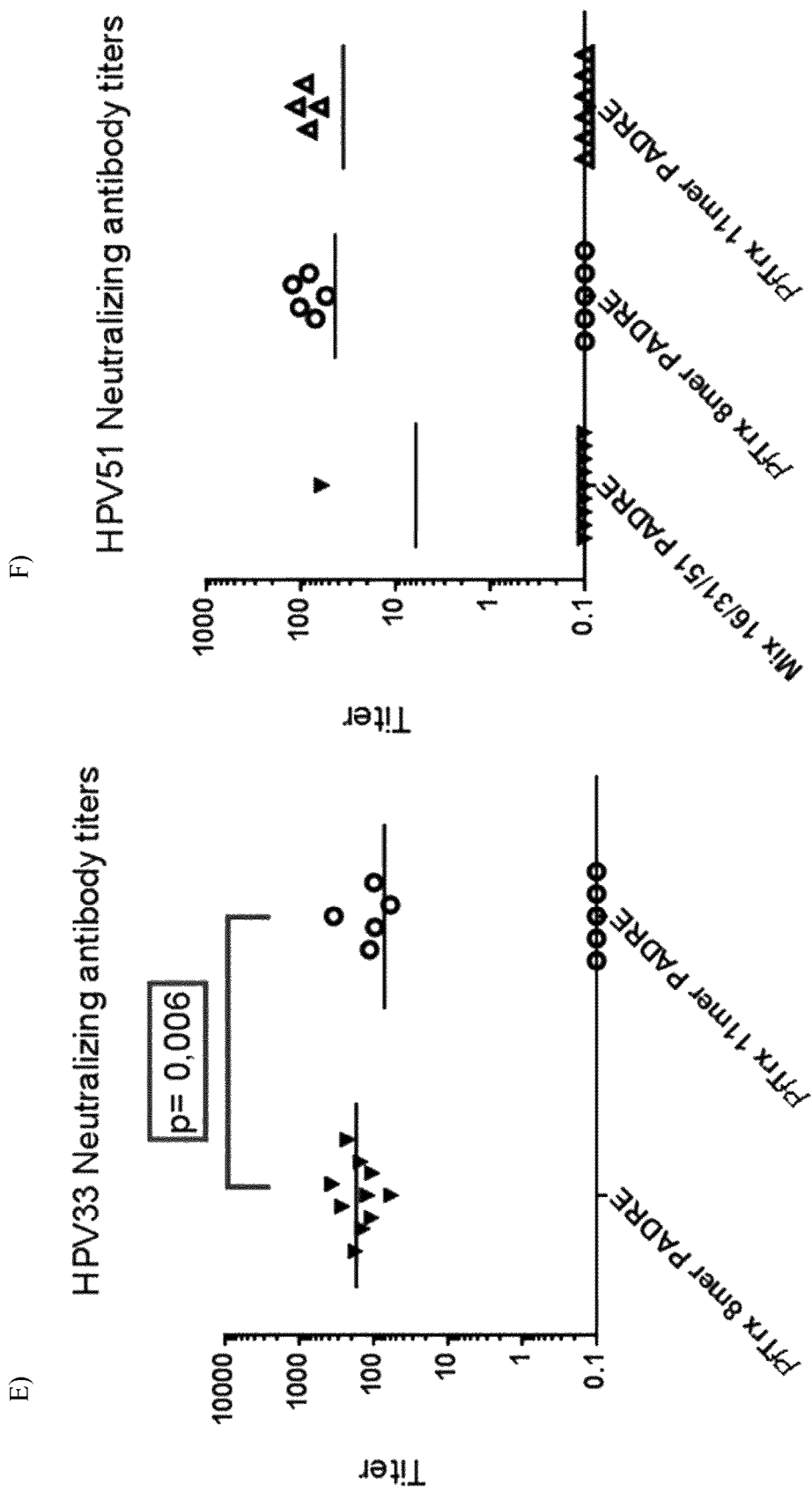
Figure 1:
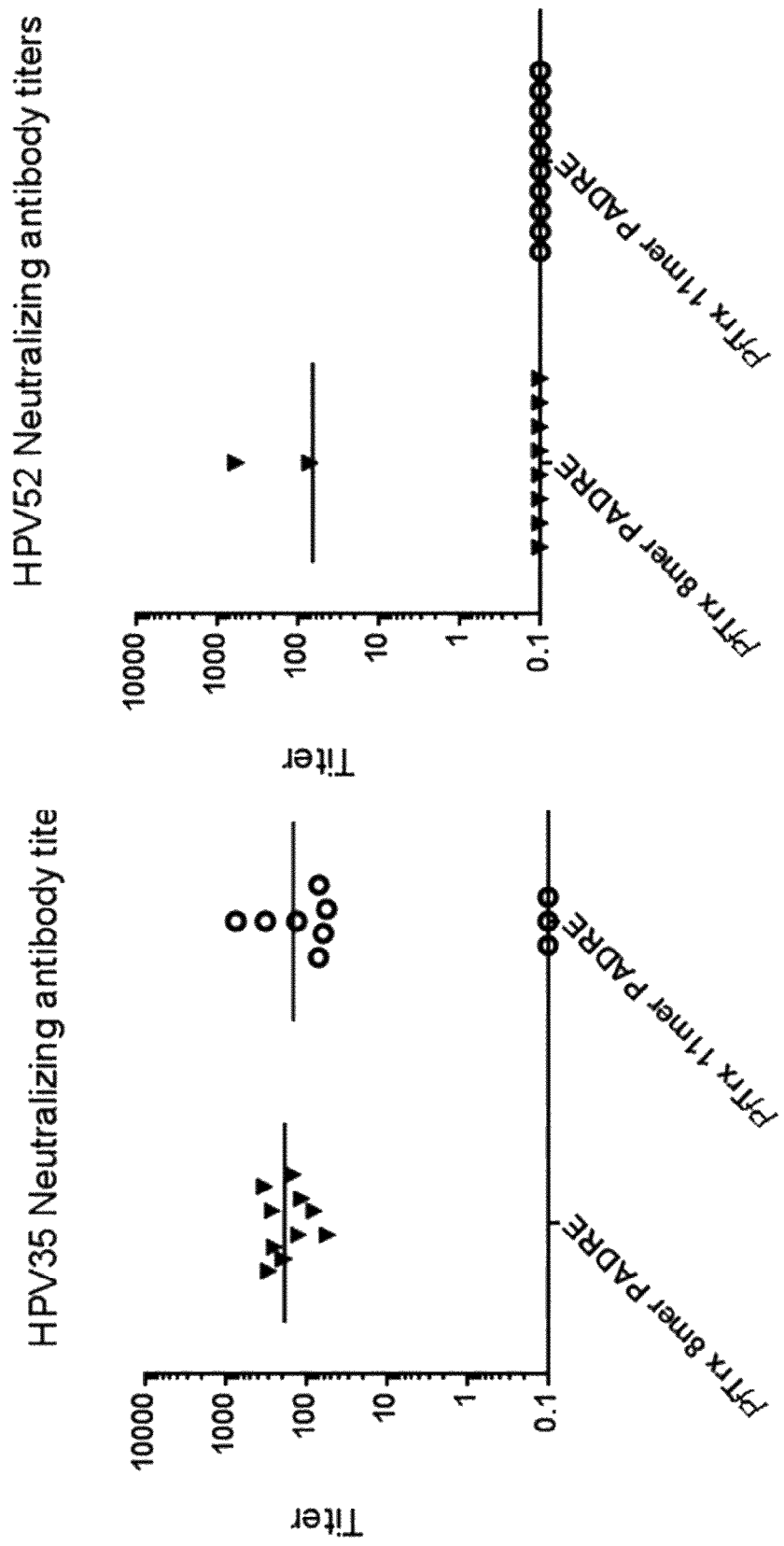
Figure 1:
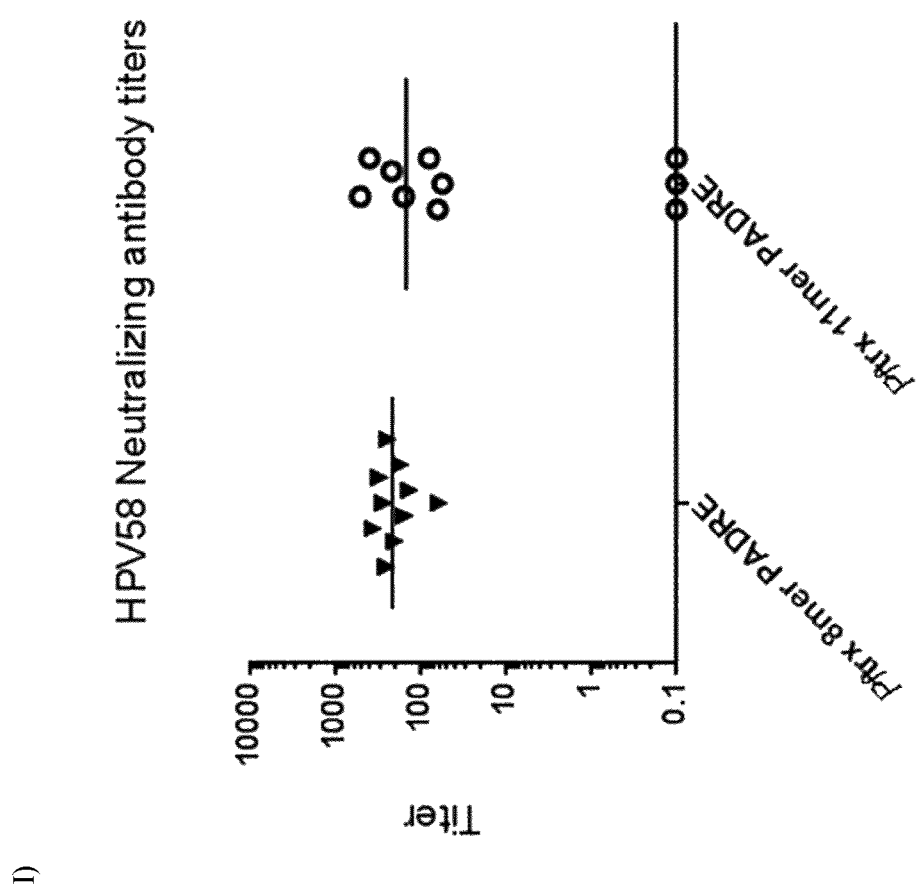

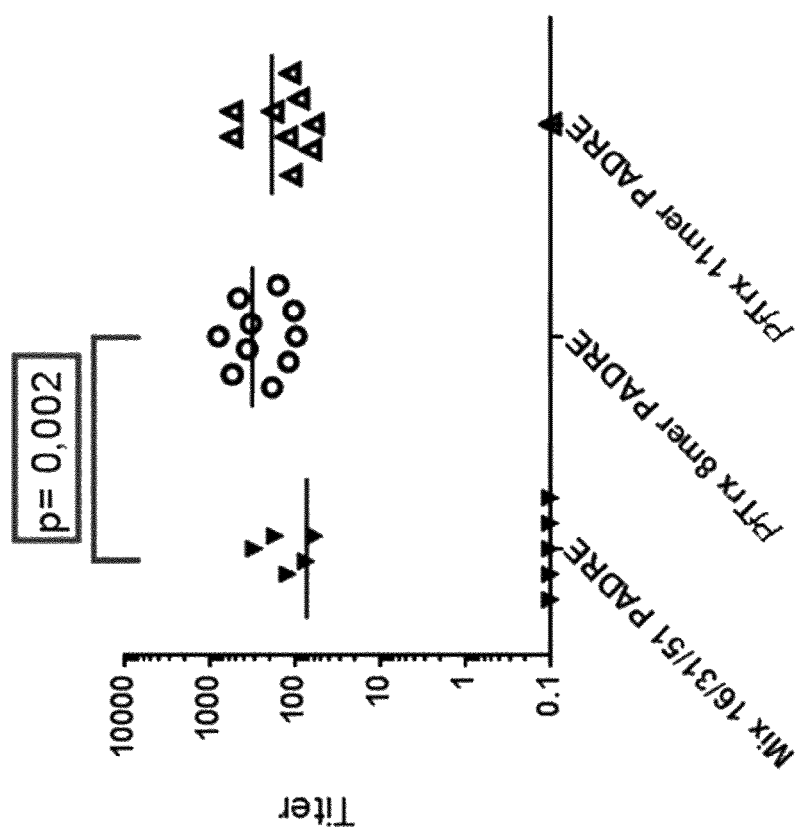
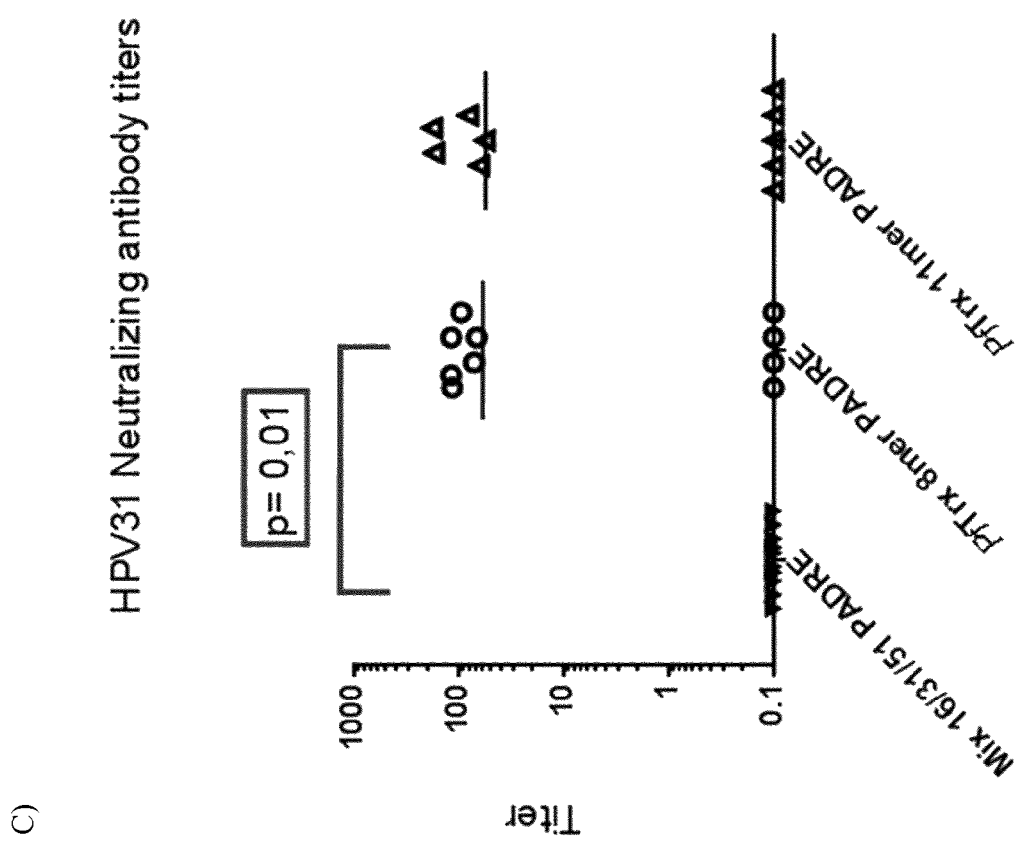
Fig. 1 (continued)

Figure 3:
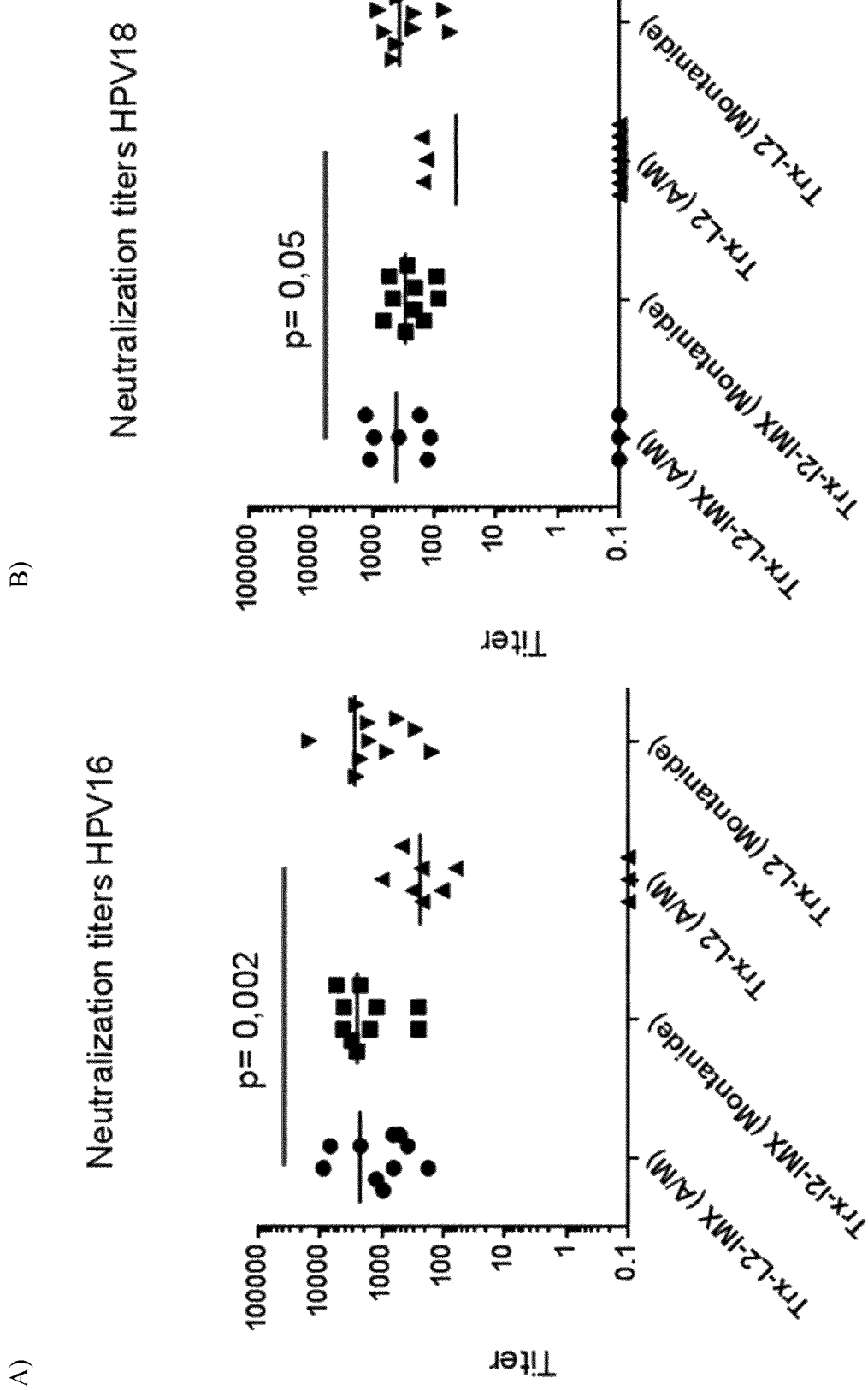
Figure 3:
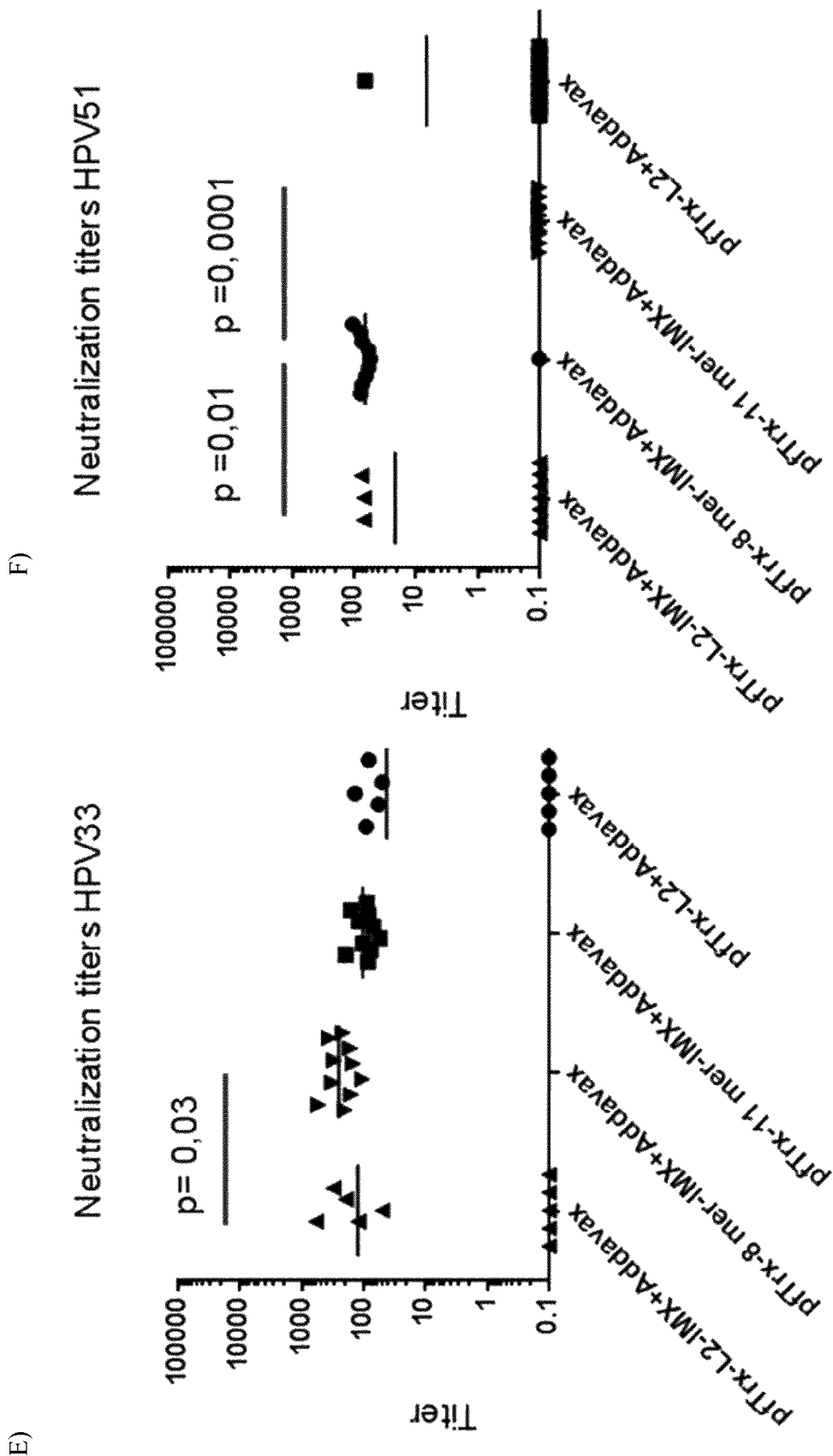
Figure 3:
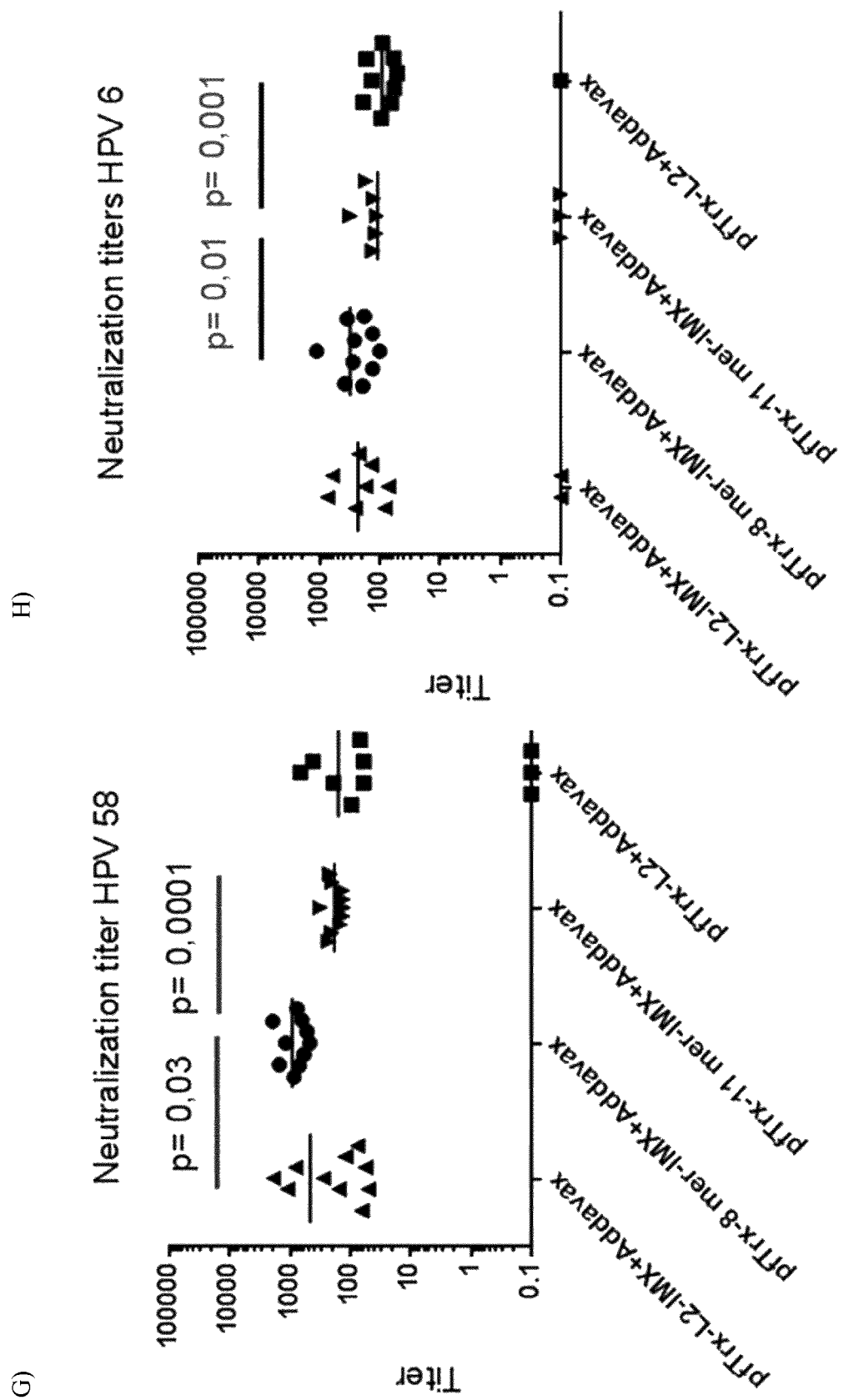

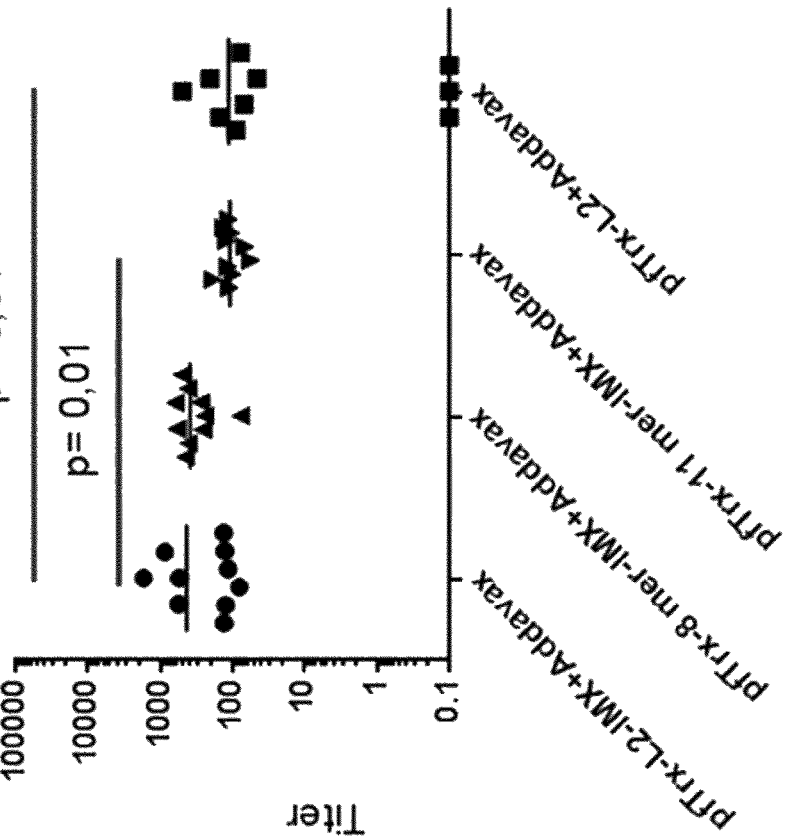
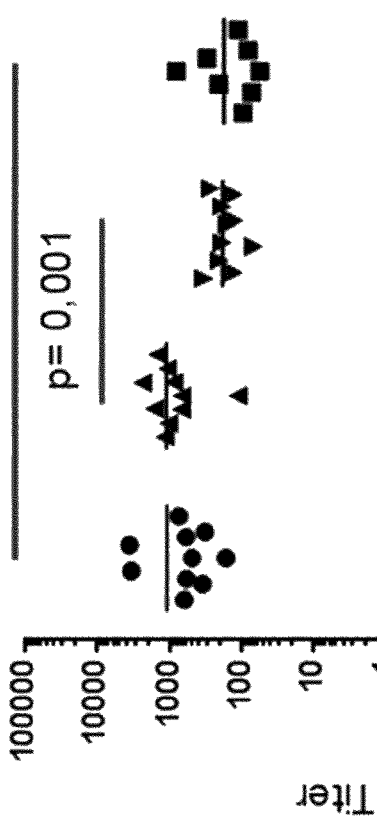
Fig. 3 (continued)

Figure 4:
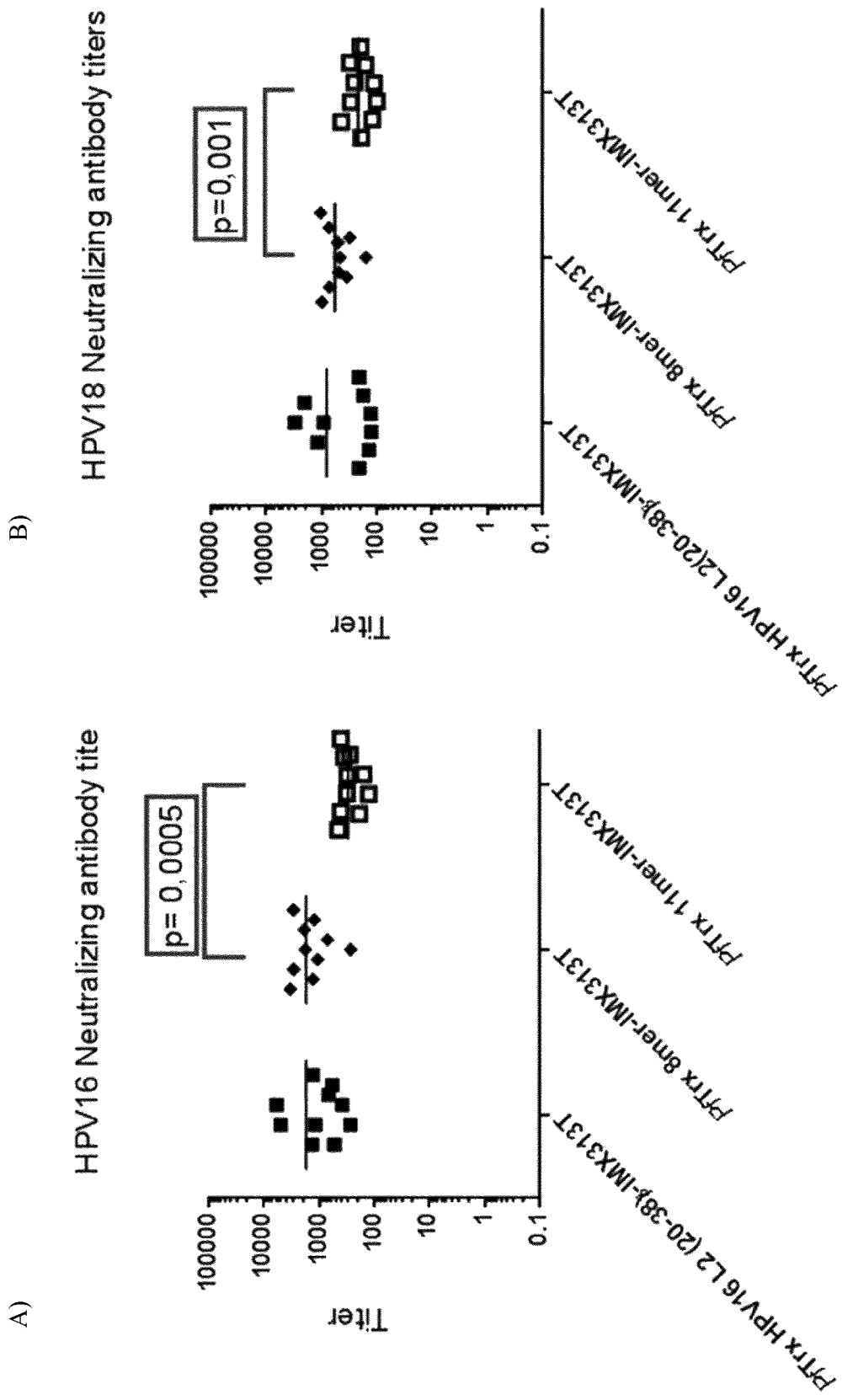
Figure 4:
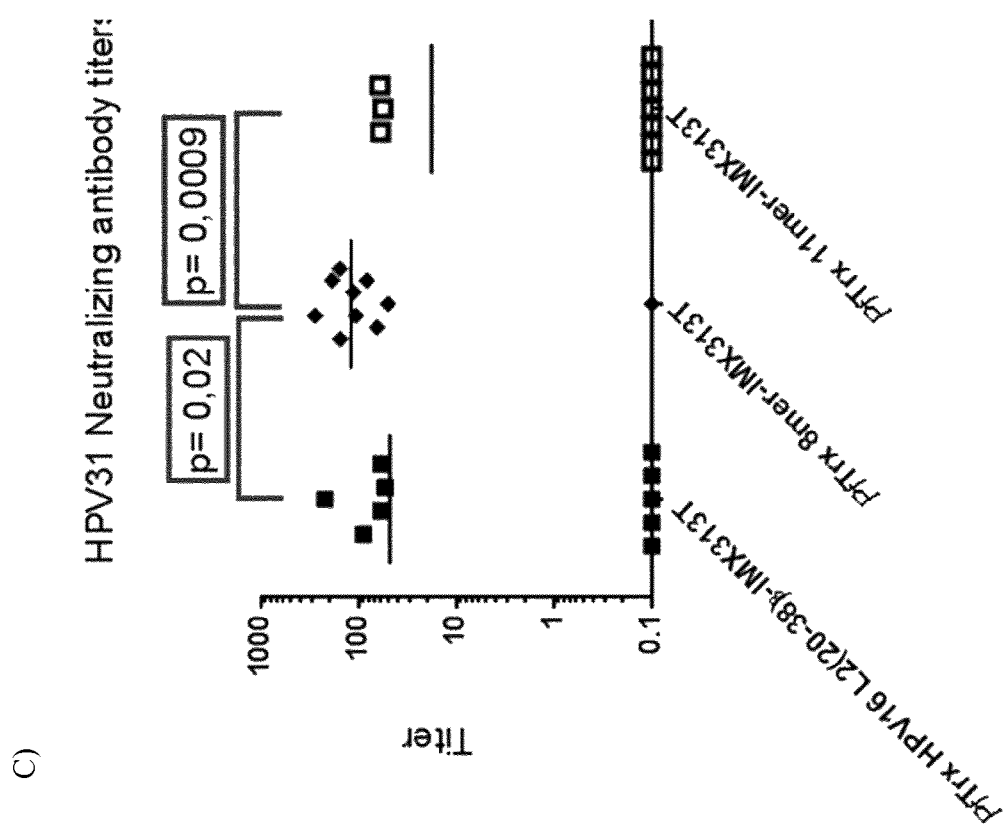
Figure 4:
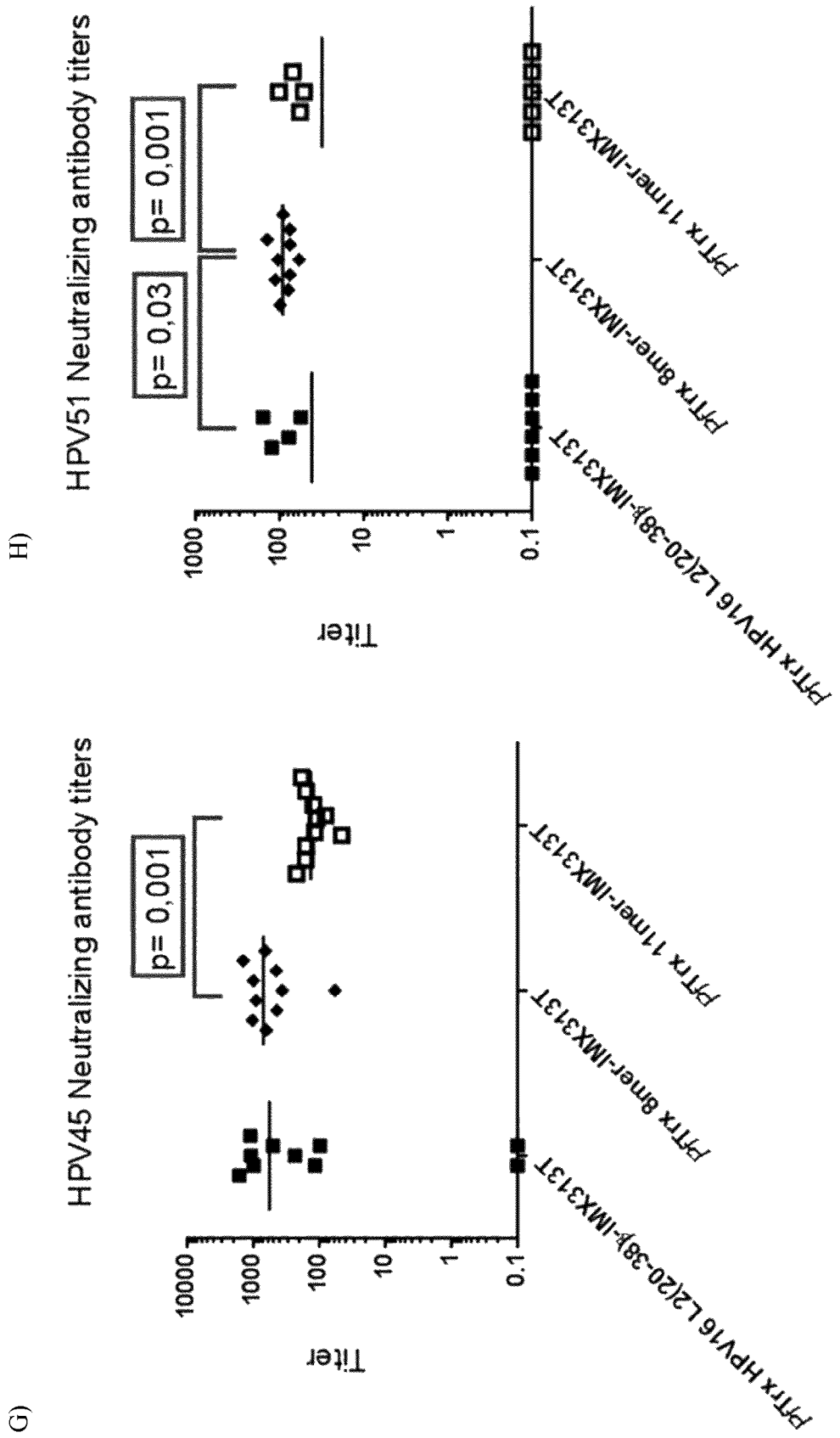

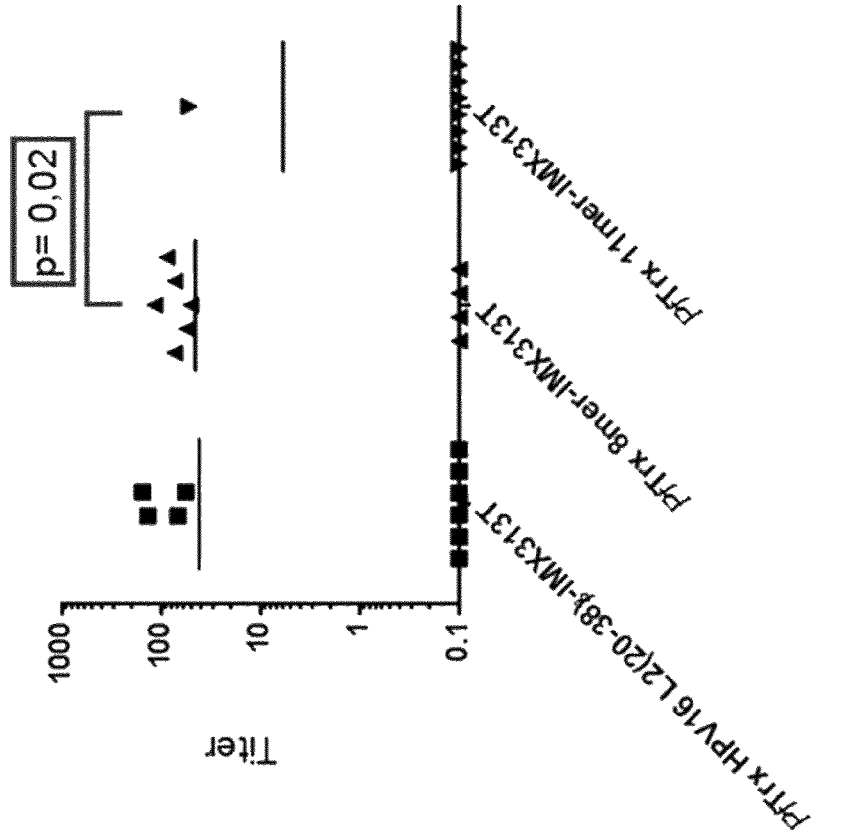
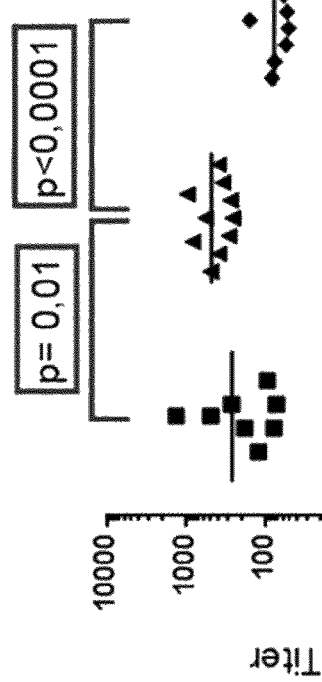
Fig. 4 (continued)

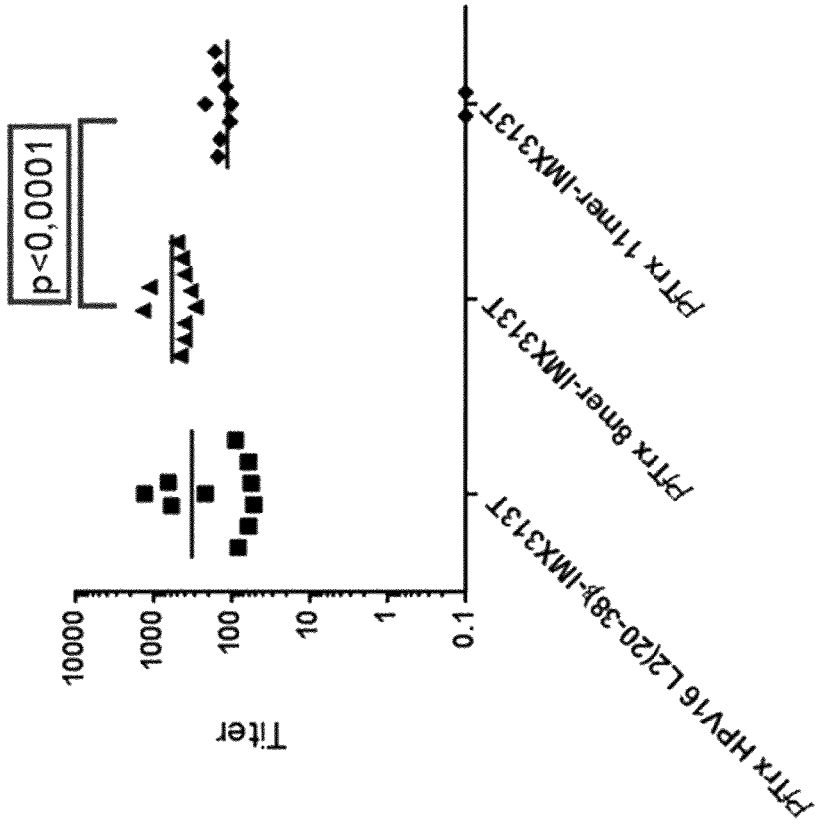
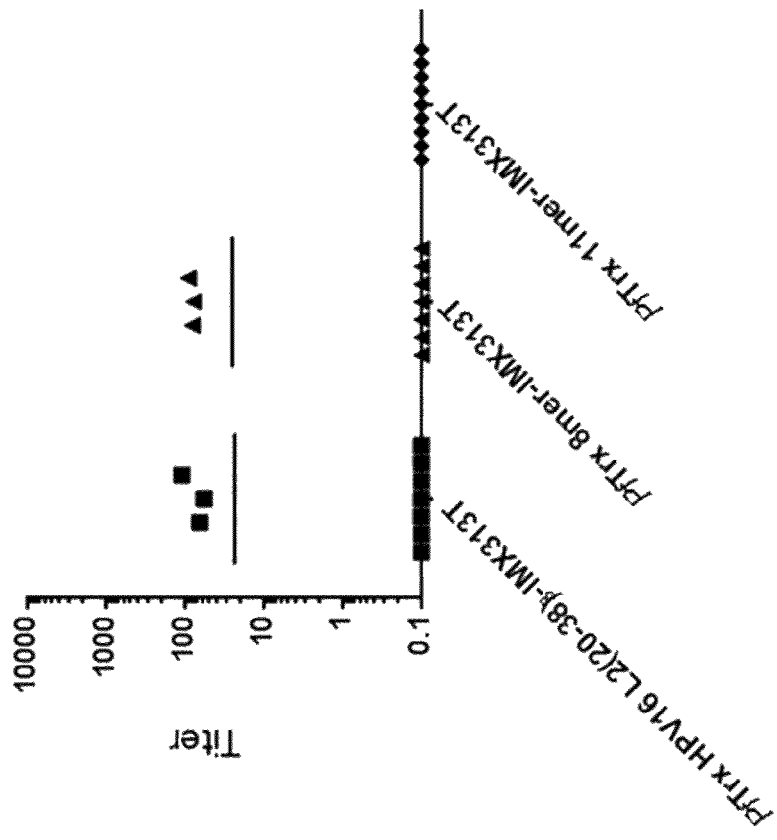
Fig. 4 (continued)

Figure 5:
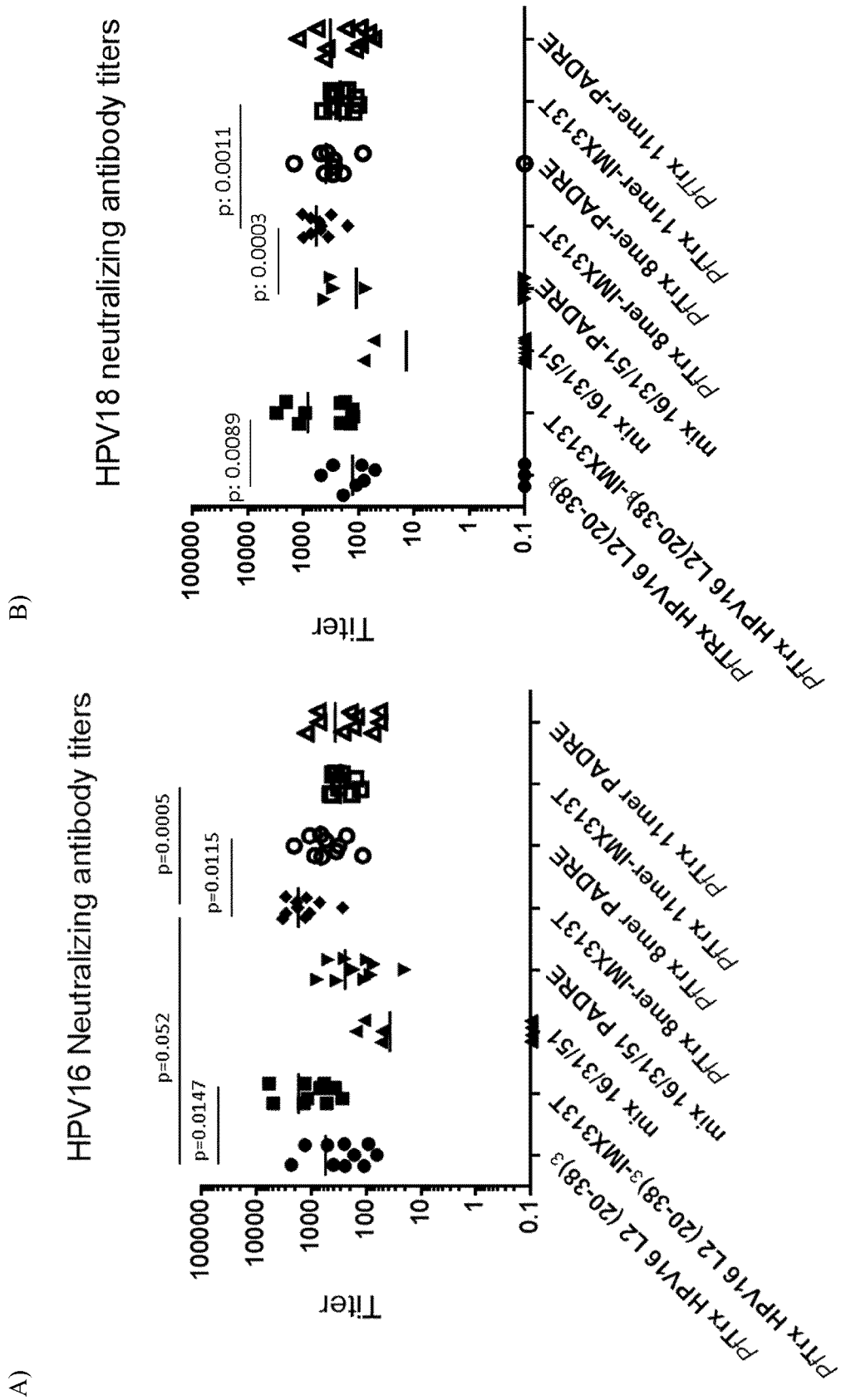
Figure 5:
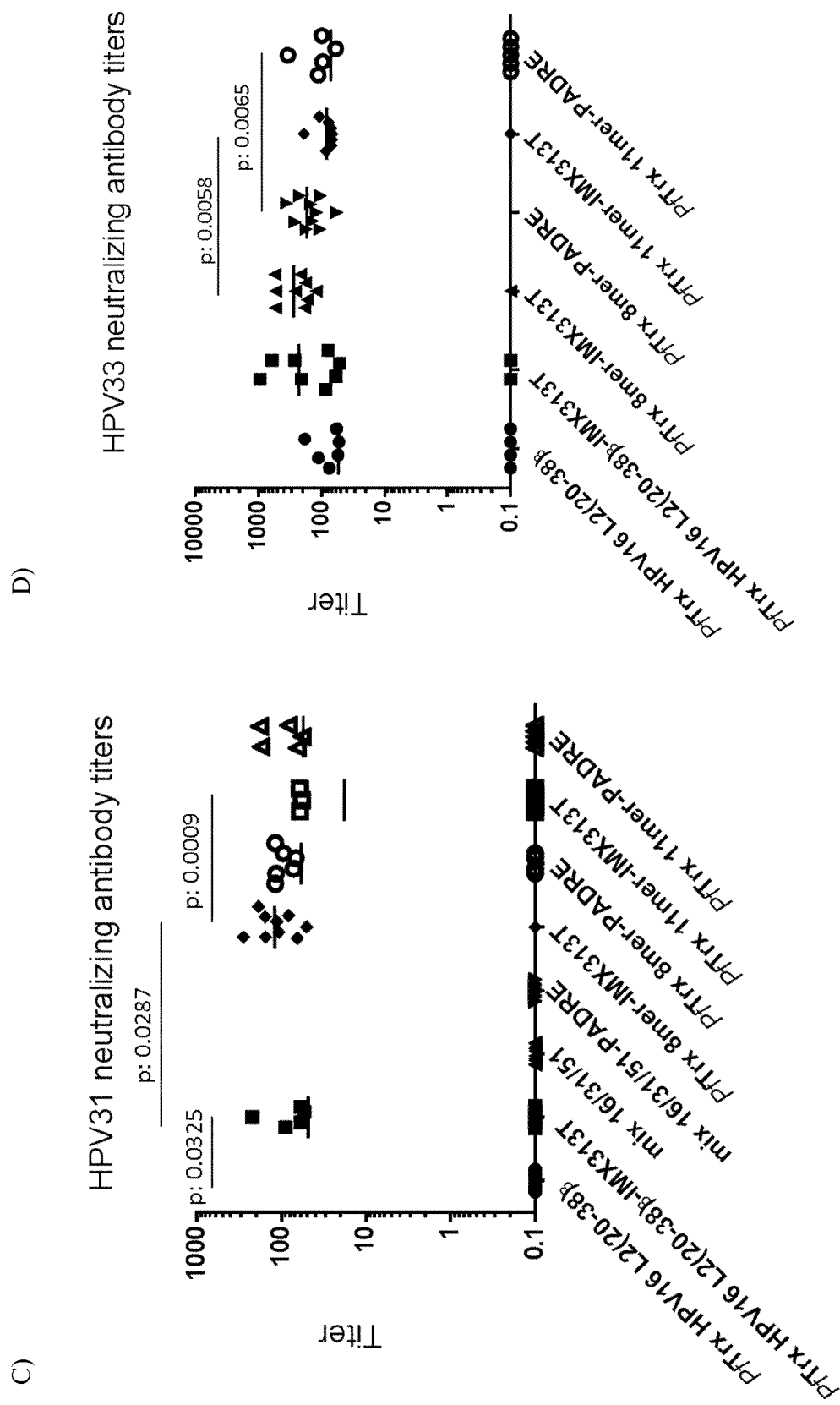
Figure 5:
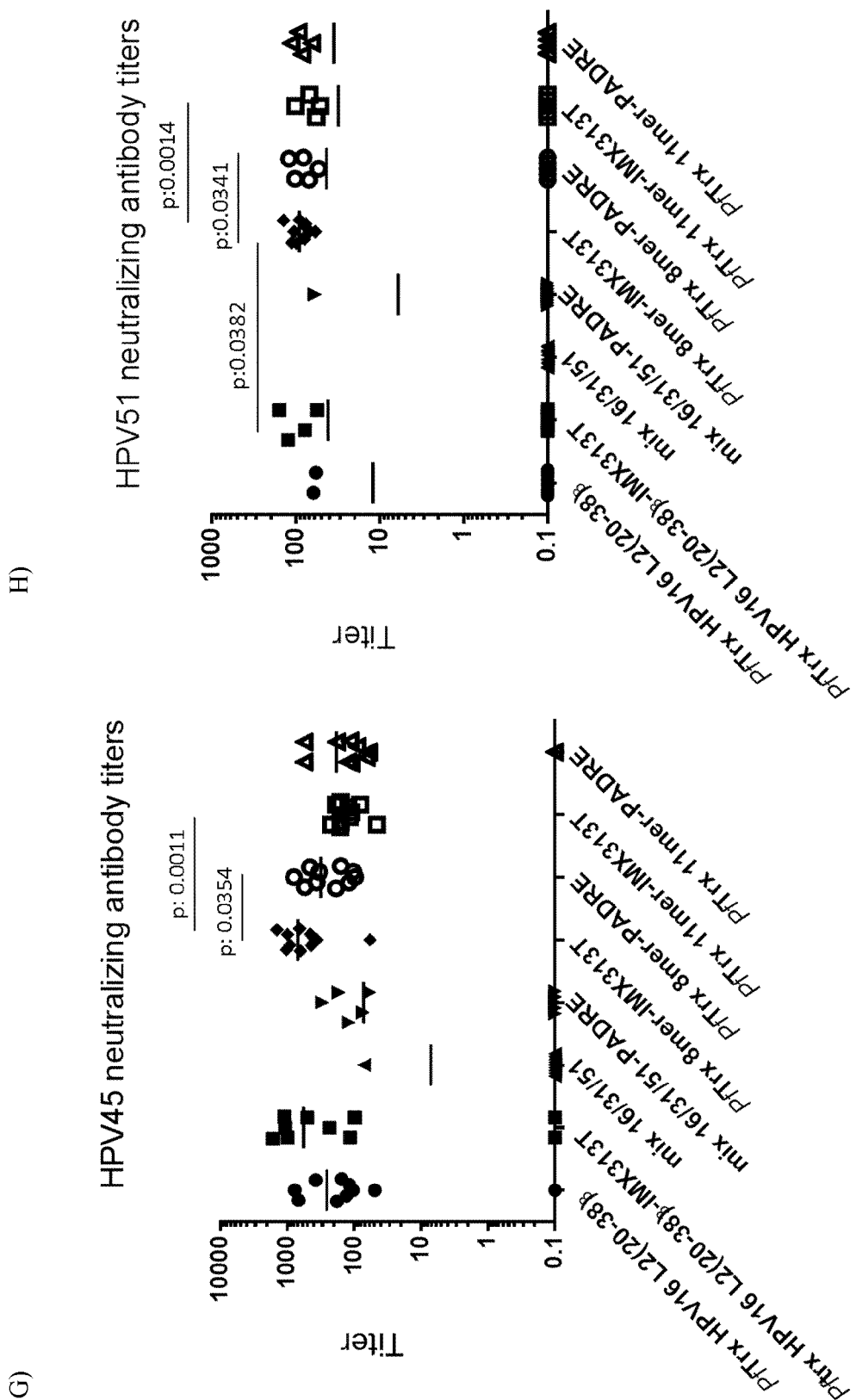
Figure 5:
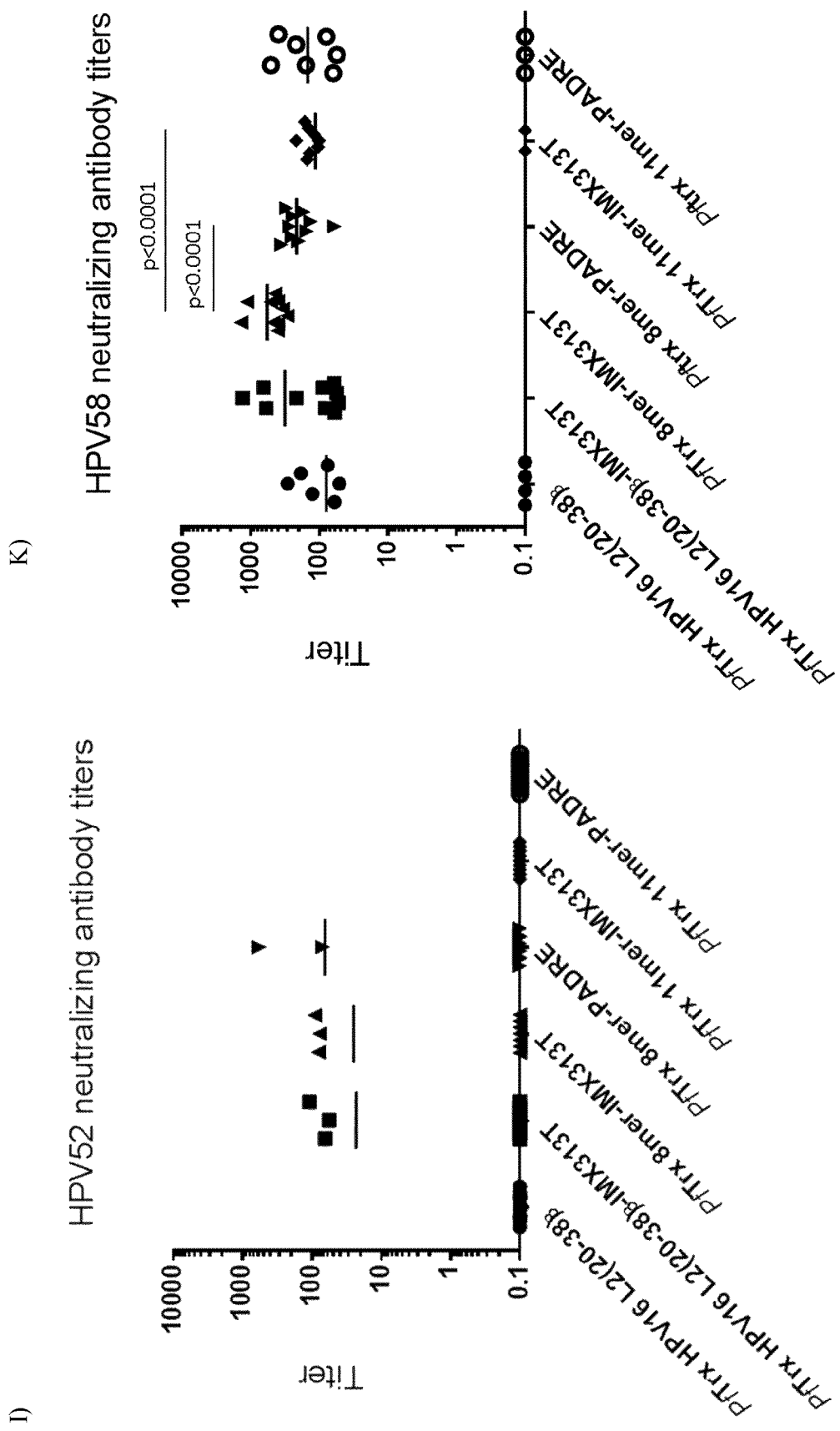

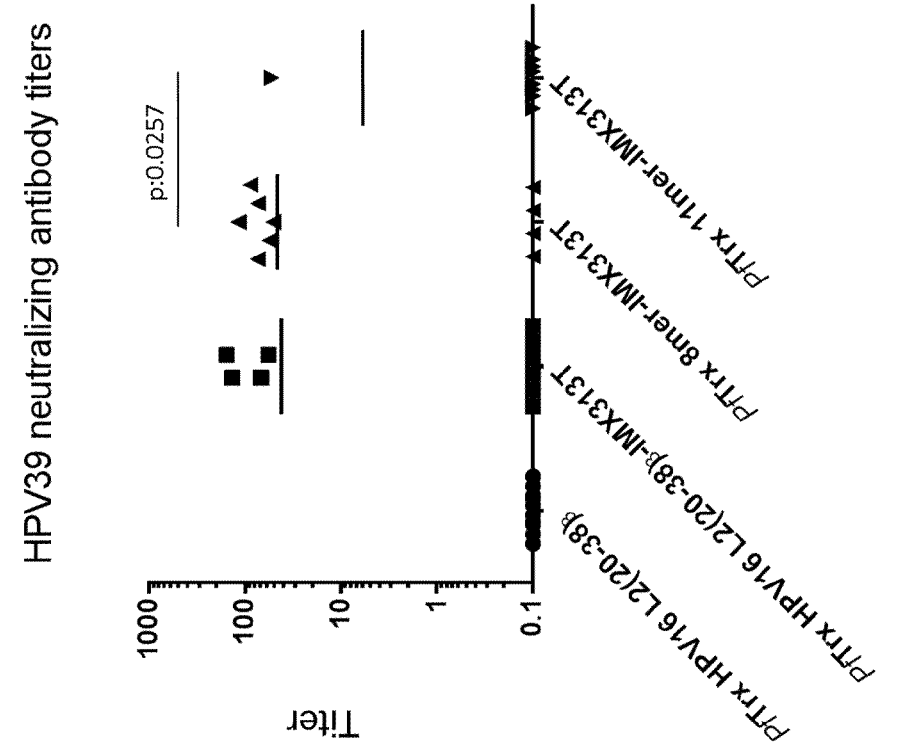
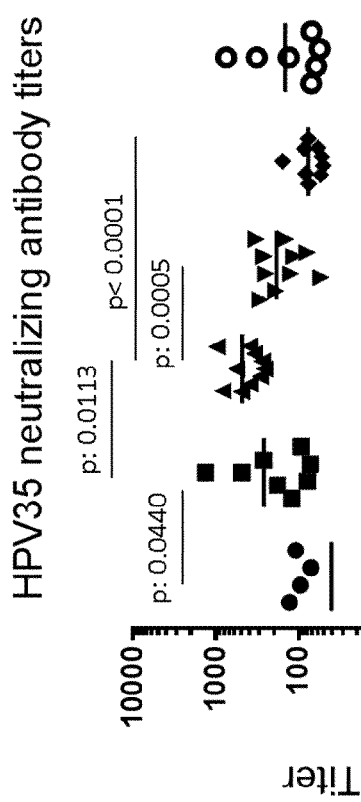
Fig. 5 (continued)

A)
```
KTCKQAGTCP PDIIPKVEGG GPKTCKQSGT CPPDVVPKVE GGGPQTCKAA GTCPSDVIPK   60
IEHGGPQTCK ATGTCPPDVI PKVEGGGPRT CKAAGTCPPD VIPKVEGGGP RTCKQSGTCP  120
PDVVDKVEGG GPRTCKQSGT CPPDVINKVE GGGPSTCKAA GTCPPDVVNK VEGGPKTCK   180
LSGTCPEDVV NKIEQGGPKT CKQAGTCPSD VINKVEGGGP STCKAAGTCP PDVIPKVKGG  240
```

B)
```
KTCKQAGTCP PDIIPKVEGG GPKTCKQSGT CPPDVVPKVE GGGPQTCKAA GTCPSDVIPK   60
IEHGGPQTCK ATGTCPPDVI PKVEGGGPRT CKAAGTCPPD VIPKVEGGGP QTCKLTGTCP  120
PDVIPKVEHG GPSTCKAAGT GGGPKTCKQA GTCPSDVINK VEGG                  174
```

C)
```
MIIEYDGEID FTKGRVVLWF SIPGCGPKTC KQAGTCPPDI IPKVEGGGPK TCKQSGTCPP   60
DVVPKVEGGG PQTCKAAGTC PSDVIPKIEH GGPQTCKATG TCPPDVIPKV EGGGPRTCKA  120
AGTCPPDVIP KVEGGPRTC KQSGTCPPDV VDKVEGGGPR TCKQSGTCPP DVINKVEGGG  180
PSTCKAAGTC PPDVVNKVEG GGPKTCKLSG TCPEDVVNKI EQGGPKTCKQ AGTCPSDVIN  240
KVEGGGPSTC KAAGTCPPDV IPKVKGGGPC RLVERFMTEL SEYFEDIQIV HINAGKWKNI  300
VDKFNILNVP TLVYLKDGRE VGRQNLIRSK EEILKKLKEL QE                    342
```

D)
```
MIIEYDGEID FTKGRVVLWF SIPGCGPKTC KQAGTCPPDI IPKVEGGGPK TCKQSGTCPP   60
DVVPKVEGGG PQTCKAAGTC PSDVIPKIEH GGPQTCKATG TCPPDVIPKV EGGGPRTCKA  120
AGTCPPDVIP KVEGGGPQTC KLTGTCPPDV IPKVEHGGPS TCKAAGTCPP DVVNKVEGGG  180
PKTCKQAGTC PSDVINKVEG GGPCRLVERF MTELSEYFED IQIVHINAGK WKNIVDKFNI  240
LNVPTLVYLK DGREVGRQNL IRSKEEILKK LKELQE                           276
```

Fig. 6

A)
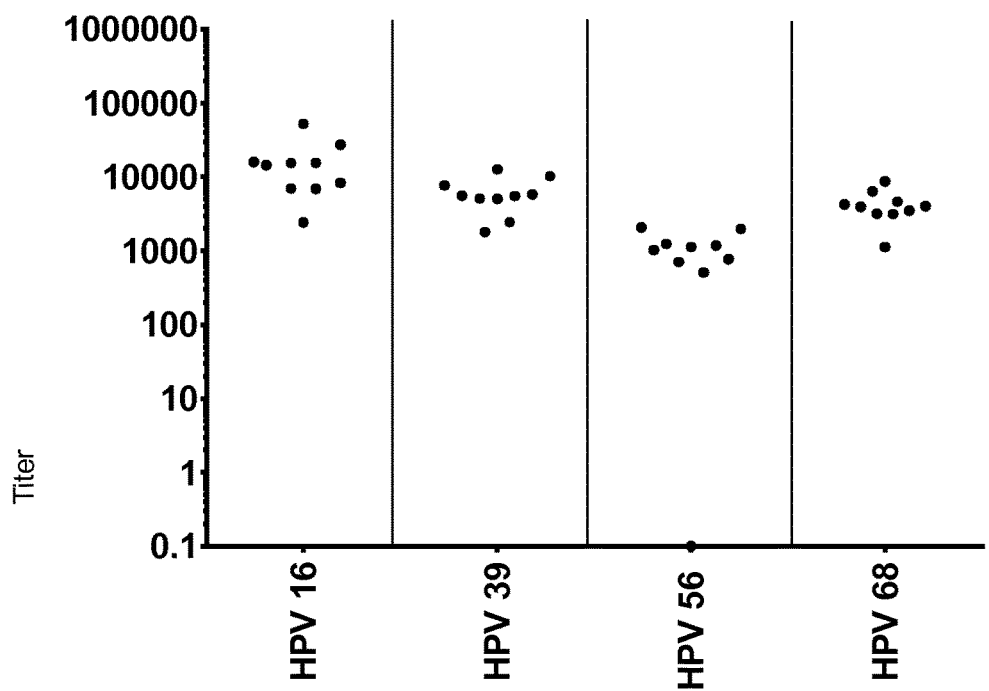
B)
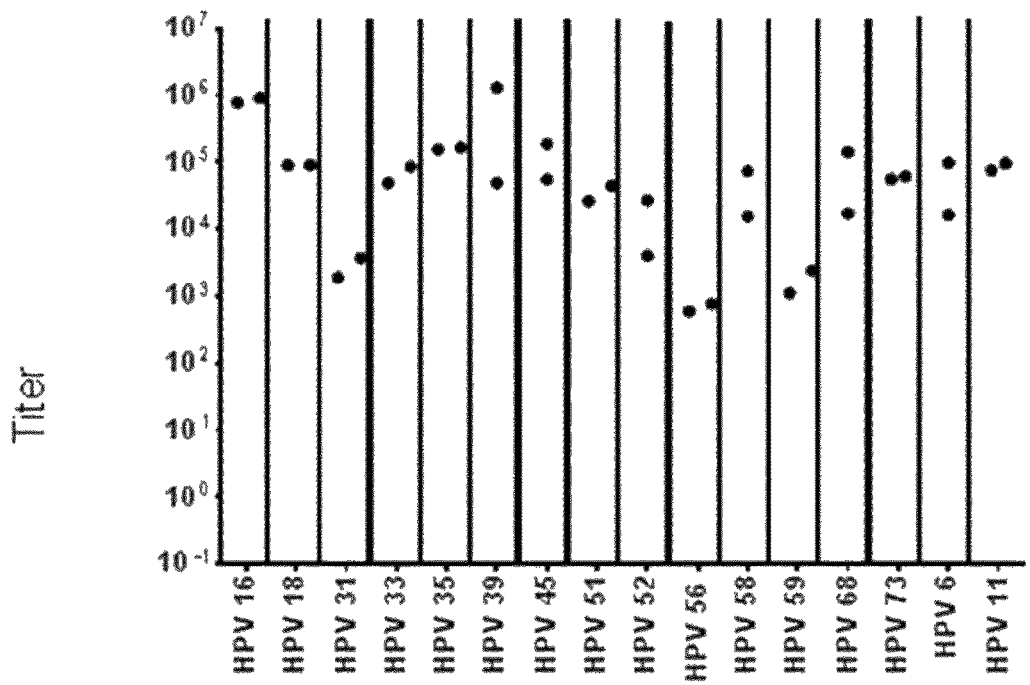
Fig. 8

SEQUENCE LISTING

<160> NUMBER OF SEQ ID NOS: 82

<210> SEQ ID NO 1
<211> LENGTH: 30
<212> TYPE: PRT
<213> ORGANISM: Human papillomavirus

<400> SEQUENCE: 1

Thr Cys Lys Gln Ala Gly Thr Cys Pro Pro Asp Ile Ile Pro Lys Val
1               5                   10                  15

Glu Gly Lys Thr Ile Ala Asp Gln Ile Leu Gln Tyr Gly Ser
            20                  25                  30

<210> SEQ ID NO 2
<211> LENGTH: 30
<212> TYPE: PRT
<213> ORGANISM: Human papillomavirus

<400> SEQUENCE: 2

Thr Cys Lys Gln Ser Gly Thr Cys Pro Pro Asp Val Val Pro Lys Val
1               5                   10                  15

Glu Gly Thr Thr Leu Ala Asp Lys Ile Leu Gln Trp Ser Ser
            20                  25                  30

<210> SEQ ID NO 3
<211> LENGTH: 30
<212> TYPE: PRT
<213> ORGANISM: Human papillomavirus

<400> SEQUENCE: 3

Thr Cys Lys Gln Ser Gly Thr Cys Pro Pro Asp Val Ile Asn Lys Val
1               5                   10                  15

Glu Gly Thr Thr Leu Ala Asp Lys Ile Leu Gln Trp Ser Ser
            20                  25                  30

<210> SEQ ID NO 4
<211> LENGTH: 30
<212> TYPE: PRT
<213> ORGANISM: Human papillomavirus

<400> SEQUENCE: 4

Thr Cys Lys Ala Ala Gly Thr Cys Pro Ser Asp Val Ile Pro Lys Ile
1               5                   10                  15

Glu His Thr Thr Ile Ala Asp Gln Ile Leu Arg Tyr Gly Ser
            20                  25                  30

<210> SEQ ID NO 5
<211> LENGTH: 30
<212> TYPE: PRT
<213> ORGANISM: Human papillomavirus

<400> SEQUENCE: 5

Thr Cys Lys Ala Thr Gly Thr Cys Pro Pro Asp Val Ile Pro Lys Val
1               5                   10                  15

Glu Gly Ser Thr Ile Ala Asp Gln Ile Leu Lys Tyr Gly Ser
            20                  25                  30

<210> SEQ ID NO 6
<211> LENGTH: 30
<212> TYPE: PRT
<213> ORGANISM: Human papillomavirus -continued

```
<400> SEQUENCE: 6

Thr Cys Lys Ala Ala Gly Thr Cys Pro Pro Asp Val Ile Pro Lys Val
1               5                   10                  15

Glu Gly Asn Thr Val Ala Asp Gln Ile Leu Lys Tyr Gly Ser
            20                  25                  30

<210> SEQ ID NO 7
<211> LENGTH: 30
<212> TYPE: PRT
<213> ORGANISM: Human papillomavirus

<400> SEQUENCE: 7

Thr Cys Lys Gln Ala Gly Thr Cys Pro Ser Asp Val Ile Asn Lys Val
1               5                   10                  15

Glu Gly Thr Thr Leu Ala Gly Lys Ile Leu Gln Trp Thr Ser
            20                  25                  30

<210> SEQ ID NO 8
<211> LENGTH: 30
<212> TYPE: PRT
<213> ORGANISM: Human papillomavirus

<400> SEQUENCE: 8

Thr Cys Lys Leu Ser Gly Thr Cys Pro Glu Asp Val Val Asn Lys Ile
1               5                   10                  15

Glu Gln Lys Thr Trp Ala Asp Lys Ile Leu Gln Trp Gly Ser
            20                  25                  30

<210> SEQ ID NO 9
<211> LENGTH: 30
<212> TYPE: PRT
<213> ORGANISM: Human papillomavirus

<400> SEQUENCE: 9

Thr Cys Lys Ala Ala Gly Thr Cys Pro Pro Asp Val Val Asn Lys Val
1               5                   10                  15

Glu Gly Thr Thr Leu Ala Asp Lys Ile Leu Gln Trp Ser Gly
            20                  25                  30

<210> SEQ ID NO 10
<211> LENGTH: 30
<212> TYPE: PRT
<213> ORGANISM: Human papillomavirus

<400> SEQUENCE: 10

Thr Cys Lys Gln Ser Gly Thr Cys Pro Pro Asp Val Val Asp Lys Val
1               5                   10                  15

Glu Gly Thr Thr Leu Ala Asp Lys Ile Leu Gln Trp Thr Ser
            20                  25                  30

<210> SEQ ID NO 11
<211> LENGTH: 30
<212> TYPE: PRT
<213> ORGANISM: Human papillomavirus

<400> SEQUENCE: 11

Thr Cys Lys Ala Ala Gly Thr Cys Pro Pro Asp Val Ile Pro Lys Val
1               5                   10                  15

Lys Gly Thr Thr Leu Ala Asp Lys Ile Leu Gln Trp Ser Gly
            20                  25                  30
```

```
<210> SEQ ID NO 12
<211> LENGTH: 30
<212> TYPE: PRT
<213> ORGANISM: Human papillomavirus

<400> SEQUENCE: 12

Thr Cys Lys Leu Thr Gly Thr Cys Pro Pro Asp Val Ile Pro Lys Val
1               5                   10                  15

Glu His Asn Thr Ile Ala Asp Gln Ile Leu Lys Trp Gly Ser
            20                  25                  30

<210> SEQ ID NO 13
<211> LENGTH: 19
<212> TYPE: PRT
<213> ORGANISM: Human papillomavirus

<400> SEQUENCE: 13

Lys Thr Cys Lys Gln Ala Gly Thr Cys Pro Pro Asp Ile Ile Pro Lys
1               5                   10                  15

Val Glu Gly

<210> SEQ ID NO 14
<211> LENGTH: 19
<212> TYPE: PRT
<213> ORGANISM: Human papillomavirus

<400> SEQUENCE: 14

Lys Thr Cys Lys Gln Ser Gly Thr Cys Pro Pro Asp Val Val Pro Lys
1               5                   10                  15

Val Glu Gly

<210> SEQ ID NO 15
<211> LENGTH: 19
<212> TYPE: PRT
<213> ORGANISM: Human papillomavirus

<400> SEQUENCE: 15

Arg Thr Cys Lys Gln Ser Gly Thr Cys Pro Pro Asp Val Ile Asn Lys
1               5                   10                  15

Val Glu Gly

<210> SEQ ID NO 16
<211> LENGTH: 19
<212> TYPE: PRT
<213> ORGANISM: Human papillomavirus

<400> SEQUENCE: 16

Gln Thr Cys Lys Ala Ala Gly Thr Cys Pro Ser Asp Val Ile Pro Lys
1               5                   10                  15

Ile Glu His

<210> SEQ ID NO 17
<211> LENGTH: 19
<212> TYPE: PRT
<213> ORGANISM: Human papillomavirus

<400> SEQUENCE: 17

Gln Thr Cys Lys Ala Thr Gly Thr Cys Pro Pro Asp Val Ile Pro Lys
1               5                   10                  15

Val Glu Gly
```

```
<210> SEQ ID NO 18
<211> LENGTH: 19
<212> TYPE: PRT
<213> ORGANISM: Human papillomavirus

<400> SEQUENCE: 18

Arg Thr Cys Lys Ala Ala Gly Thr Cys Pro Pro Asp Val Ile Pro Lys
1               5                   10                  15

Val Glu Gly

<210> SEQ ID NO 19
<211> LENGTH: 19
<212> TYPE: PRT
<213> ORGANISM: Human papillomavirus

<400> SEQUENCE: 19

Lys Thr Cys Lys Gln Ala Gly Thr Cys Pro Ser Asp Val Ile Asn Lys
1               5                   10                  15

Val Glu Gly

<210> SEQ ID NO 20
<211> LENGTH: 19
<212> TYPE: PRT
<213> ORGANISM: Human papillomavirus

<400> SEQUENCE: 20

Lys Thr Cys Lys Leu Ser Gly Thr Cys Pro Glu Asp Val Val Asn Lys
1               5                   10                  15

Ile Glu Gln

<210> SEQ ID NO 21
<211> LENGTH: 19
<212> TYPE: PRT
<213> ORGANISM: Human papillomavirus

<400> SEQUENCE: 21

Ser Thr Cys Lys Ala Ala Gly Thr Cys Pro Pro Asp Val Val Asn Lys
1               5                   10                  15

Val Glu Gly

<210> SEQ ID NO 22
<211> LENGTH: 19
<212> TYPE: PRT
<213> ORGANISM: Human papillomavirus

<400> SEQUENCE: 22

Arg Thr Cys Lys Gln Ser Gly Thr Cys Pro Pro Asp Val Val Asp Lys
1               5                   10                  15

Val Glu Gly

<210> SEQ ID NO 23
<211> LENGTH: 19
<212> TYPE: PRT
<213> ORGANISM: Human papillomavirus

<400> SEQUENCE: 23

Ser Thr Cys Lys Ala Ala Gly Thr Cys Pro Pro Asp Val Ile Pro Lys
1               5                   10                  15

Val Lys Gly

<210> SEQ ID NO 24
```

<211> LENGTH: 19
<212> TYPE: PRT
<213> ORGANISM: Human papillomavirus

<400> SEQUENCE: 24

Gln Thr Cys Lys Leu Thr Gly Thr Cys Pro Pro Asp Val Ile Pro Lys
1               5                   10                  15

Val Glu His

<210> SEQ ID NO 25
<211> LENGTH: 240
<212> TYPE: PRT
<213> ORGANISM: Artificial
<220> FEATURE:
<223> OTHER INFORMATION: 11 mer of peptides from various HPV

<400> SEQUENCE: 25

Lys Thr Cys Lys Gln Ala Gly Thr Cys Pro Pro Asp Ile Ile Pro Lys
1               5                   10                  15

Val Glu Gly Gly Gly Pro Lys Thr Cys Lys Gln Ser Gly Thr Cys Pro
            20                  25                  30

Pro Asp Val Val Pro Lys Val Glu Gly Gly Gly Pro Gln Thr Cys Lys
        35                  40                  45

Ala Ala Gly Thr Cys Pro Ser Asp Val Ile Pro Lys Ile Glu His Gly
    50                  55                  60

Gly Pro Gln Thr Cys Lys Ala Thr Gly Thr Cys Pro Pro Asp Val Ile
65                  70                  75                  80

Pro Lys Val Glu Gly Gly Gly Pro Arg Thr Cys Lys Ala Ala Gly Thr
                85                  90                  95

Cys Pro Pro Asp Val Ile Pro Lys Val Glu Gly Gly Gly Pro Arg Thr
            100                 105                 110

Cys Lys Gln Ser Gly Thr Cys Pro Pro Asp Val Val Asp Lys Val Glu
        115                 120                 125

Gly Gly Gly Pro Arg Thr Cys Lys Gln Ser Gly Thr Cys Pro Pro Asp
    130                 135                 140

Val Ile Asn Lys Val Glu Gly Gly Gly Pro Ser Thr Cys Lys Ala Ala
145                 150                 155                 160

Gly Thr Cys Pro Pro Asp Val Val Asn Lys Val Glu Gly Gly Gly Pro
                165                 170                 175

Lys Thr Cys Lys Leu Ser Gly Thr Cys Pro Glu Asp Val Val Asn Lys
            180                 185                 190

Ile Glu Gln Gly Gly Pro Lys Thr Cys Lys Gln Ala Gly Thr Cys Pro
        195                 200                 205

Ser Asp Val Ile Asn Lys Val Glu Gly Gly Pro Ser Thr Cys Lys
    210                 215                 220

Ala Ala Gly Thr Cys Pro Pro Asp Val Ile Pro Lys Val Lys Gly Gly
225                 230                 235                 240

<210> SEQ ID NO 26
<211> LENGTH: 174
<212> TYPE: PRT
<213> ORGANISM: Artificial
<220> FEATURE:
<223> OTHER INFORMATION: 8mer of peptides from various HPV

<400> SEQUENCE: 26

Lys Thr Cys Lys Gln Ala Gly Thr Cys Pro Pro Asp Ile Ile Pro Lys
1               5                   10                  15

```
Val Glu Gly Gly Gly Pro Lys Thr Cys Lys Gln Ser Gly Thr Cys Pro
            20                  25                  30

Pro Asp Val Val Pro Lys Val Glu Gly Gly Pro Gln Thr Cys Lys
        35                  40                  45

Ala Ala Gly Thr Cys Pro Ser Asp Val Ile Pro Lys Ile Glu His Gly
50                  55                  60

Gly Pro Gln Thr Cys Lys Ala Thr Gly Thr Cys Pro Pro Asp Val Ile
65                  70                  75                  80

Pro Lys Val Glu Gly Gly Pro Arg Thr Cys Lys Ala Ala Gly Thr
            85                  90                  95

Cys Pro Pro Asp Val Ile Pro Lys Val Glu Gly Gly Pro Gln Thr
            100                 105                 110

Cys Lys Leu Thr Gly Thr Cys Pro Pro Asp Val Ile Pro Lys Val Glu
        115                 120                 125

His Gly Gly Pro Ser Thr Cys Lys Ala Ala Gly Thr Cys Pro Pro Asp
        130                 135                 140

Val Val Asn Lys Val Glu Gly Gly Gly Pro Lys Thr Cys Lys Gln Ala
145                 150                 155                 160

Gly Thr Cys Pro Ser Asp Val Ile Asn Lys Val Glu Gly Gly
            165                 170
```

<210> SEQ ID NO 27
<211> LENGTH: 342
<212> TYPE: PRT
<213> ORGANISM: Artificial
<220> FEATURE:
<223> OTHER INFORMATION: PfTrx 11mer

<400> SEQUENCE: 27

```
Met Ile Ile Glu Tyr Asp Gly Glu Ile Asp Phe Thr Lys Gly Arg Val
1               5                   10                  15

Val Leu Trp Phe Ser Ile Pro Gly Cys Gly Pro Lys Thr Cys Lys Gln
            20                  25                  30

Ala Gly Thr Cys Pro Pro Asp Ile Ile Pro Lys Val Glu Gly Gly Gly
        35                  40                  45

Pro Lys Thr Cys Lys Gln Ser Gly Thr Cys Pro Asp Val Val Pro
    50                  55                  60

Lys Val Glu Gly Gly Gly Pro Gln Thr Cys Lys Ala Ala Gly Thr Cys
65                  70                  75                  80

Pro Ser Asp Val Ile Pro Lys Ile Glu His Gly Gly Pro Gln Thr Cys
            85                  90                  95

Lys Ala Thr Gly Thr Cys Pro Pro Asp Val Ile Pro Lys Val Glu Gly
            100                 105                 110

Gly Gly Pro Arg Thr Cys Lys Ala Ala Gly Thr Cys Pro Pro Asp Val
        115                 120                 125

Ile Pro Lys Val Glu Gly Gly Gly Pro Arg Thr Cys Lys Gln Ser Gly
    130                 135                 140

Thr Cys Pro Pro Asp Val Val Asp Lys Val Glu Gly Gly Gly Pro Arg
145                 150                 155                 160

Thr Cys Lys Gln Ser Gly Thr Cys Pro Pro Asp Val Ile Asn Lys Val
            165                 170                 175

Glu Gly Gly Gly Pro Ser Thr Cys Lys Ala Ala Gly Thr Cys Pro Pro
        180                 185                 190

Asp Val Val Asn Lys Val Glu Gly Gly Gly Pro Lys Thr Cys Lys Leu
    195                 200                 205
```

Ser Gly Thr Cys Pro Glu Asp Val Val Asn Lys Ile Glu Gln Gly Gly
    210                 215                 220

Pro Lys Thr Cys Lys Gln Ala Gly Thr Cys Pro Ser Asp Val Ile Asn
225                 230                 235                 240

Lys Val Glu Gly Gly Pro Ser Thr Cys Lys Ala Ala Gly Thr Cys
                245                 250                 255

Pro Pro Asp Val Ile Pro Lys Val Lys Gly Gly Pro Cys Arg Leu
                260                 265                 270

Val Glu Arg Phe Met Thr Glu Leu Ser Glu Tyr Phe Glu Asp Ile Gln
            275                 280                 285

Ile Val His Ile Asn Ala Gly Lys Trp Lys Asn Ile Val Asp Lys Phe
    290                 295                 300

Asn Ile Leu Asn Val Pro Thr Leu Val Tyr Leu Lys Asp Gly Arg Glu
305                 310                 315                 320

Val Gly Arg Gln Asn Leu Ile Arg Ser Lys Glu Ile Leu Lys Lys
                325                 330                 335

Leu Lys Glu Leu Gln Glu
            340

<210> SEQ ID NO 28
<211> LENGTH: 1029
<212> TYPE: DNA
<213> ORGANISM: Artificial
<220> FEATURE:
<223> OTHER INFORMATION: PfTrx 11mer coding

<400> SEQUENCE: 28

```
atgattatcg agtatgacgg cgaaatcgac ttcaccaaag gtcgtgttgt actgtggttt      60
agcattccgg gatgcggtcc gaagacgtgc aaacaagcgg gcacctgtcc gcccgatatt     120
atcccgaaag tcgagggtgg tgggccgaaa acgtgcaaac agtctggaac atgcccgccg     180
gatgtggtgc cgaaagtgga aggaggaggt ccgcaaacgt gcaaagcagc agggacctgt     240
ccgtcagatg tgattccgaa gattgaacat ggtgggccac agacctgtaa agccaccggc     300
acgtgtccgc cagacgtaat ccctaaagtc aaggtggtg ccctcgtac gtgcaaagct      360 gcgggcacat gccctccgga tgttattccg aaagtagaag cggcggccc acgcacttgc      420 aaacagagtg gtacctgccc gccggacgtc gtggataaag ttgaaggcgg tggtcctcgc     480
acgtgcaagc aaagcggcac atgcccaccc gacgtaatca ataaggtcga aggcggtggg     540
ccatcgactt gtaaggcggc cgggacttgt ccgccagatg tggttaacaa agtggaaggc     600 ggcgaccta aaacttgcaa actgagtgga acctgtccgg aggatgtagt caacaaaatc     660
gaacagggcg gcccgaaaac ctgtaaacaa gcaggcacct gtccatcgga tgtgattaac     720
aaagttgaag gtgtggtcc gagcacgtgt aaagccgctg gtacatgccc tcccgatgtt     780
atccccaaag ttaaaggcgg cggtccgtgt cgtctggttg aacgcttcat gaccgaactg     840
agcgagtatt ttgaggatat ccaaattgtc catatcaatg ccggcaaatg gaaaaacatc     900
gtagacaaat tcaatattct gaacgtgccg accctggtat atctgaaaga tggccgtgag     960
gttggacgcc aaaacctgat tcgttctaaa gaagagattc tgaaaaaact gaaagagctg    1020
caggagtaa                                                            1029
```

<210> SEQ ID NO 29
<211> LENGTH: 276
<212> TYPE: PRT
<213> ORGANISM: Artificial
<220> FEATURE:

<223> OTHER INFORMATION: PfTrx 8mer

<400> SEQUENCE: 29

```
Met Ile Ile Glu Tyr Asp Gly Glu Ile Asp Phe Thr Lys Gly Arg Val
1               5                   10                  15
Val Leu Trp Phe Ser Ile Pro Gly Cys Gly Pro Lys Thr Cys Lys Gln
            20                  25                  30
Ala Gly Thr Cys Pro Pro Asp Ile Ile Pro Lys Val Glu Gly Gly Gly
        35                  40                  45
Pro Lys Thr Cys Lys Gln Ser Gly Thr Cys Pro Pro Asp Val Val Pro
    50                  55                  60
Lys Val Glu Gly Gly Pro Gln Thr Cys Lys Ala Ala Gly Thr Cys
65                  70                  75                  80
Pro Ser Asp Val Ile Pro Lys Ile Glu His Gly Gly Pro Gln Thr Cys
                85                  90                  95
Lys Ala Thr Gly Thr Cys Pro Pro Asp Val Ile Pro Lys Val Glu Gly
            100                 105                 110
Gly Gly Pro Arg Thr Cys Lys Ala Ala Gly Thr Cys Pro Pro Asp Val
        115                 120                 125
Ile Pro Lys Val Glu Gly Gly Pro Gln Thr Cys Lys Leu Thr Gly
    130                 135                 140
Thr Cys Pro Pro Asp Val Ile Pro Lys Val Glu His Gly Gly Pro Ser
145                 150                 155                 160
Thr Cys Lys Ala Ala Gly Thr Cys Pro Pro Asp Val Val Asn Lys Val
                165                 170                 175
Glu Gly Gly Gly Pro Lys Thr Cys Lys Gln Ala Gly Thr Cys Pro Ser
            180                 185                 190
Asp Val Ile Asn Lys Val Glu Gly Gly Gly Pro Cys Arg Leu Val Glu
        195                 200                 205
Arg Phe Met Thr Glu Leu Ser Glu Tyr Phe Glu Asp Ile Gln Ile Val
    210                 215                 220
His Ile Asn Ala Gly Lys Trp Lys Asn Ile Val Asp Lys Phe Asn Ile
225                 230                 235                 240
Leu Asn Val Pro Thr Leu Val Tyr Leu Lys Asp Gly Arg Glu Val Gly
                245                 250                 255
Arg Gln Asn Leu Ile Arg Ser Lys Glu Glu Ile Leu Lys Lys Leu Lys
            260                 265                 270
Glu Leu Gln Glu
    275
```

<210> SEQ ID NO 30
<211> LENGTH: 831
<212> TYPE: DNA
<213> ORGANISM: Artificial
<220> FEATURE:
<223> OTHER INFORMATION: PfTrx 8mer coding

<400> SEQUENCE: 30

| | | |
|---|---|---|
| atgattatcg agtatgacgg cgaaatcgac ttcaccaaag gtcgtgttgt actgtggttt | 60 |
| agcattccgg gatgcggtcc gaagacctgt aaacaggccg ggacttgccc accgatatt | 120 |
| attccaaagg tagaaggtgg tggacccaaa acgtgcaaac aaagcgggac gtgcccacca | 180 |
| gacgtggtgc ccaaagttga aggcggcggg ccgcaaacgt gtaaggccgc tggtacgtgc | 240 |
| ccgagtgatg ttattccgaa aattgaacat ggtggtccac agacctgtaa agcgaccggc | 300 |
| acatgcccgc cggatgtgat tcctaaagtg gaaggtggag ccctcgtac atgcaaggcg | 360 |

```
gctggtacat gcccgcctga tgtcatcccg aaagtcgaag gtggcgggcc gcagacgtgc    420
aagttgaccg gcacctgtcc gccggatgtt atcccgaaag ttgagcatgg cggcccgtct    480
acgtgcaaag cagcagggac ctgtccgcct gatgtcgtaa acaaagtcga gggtggcggt    540
cccaaaacct gtaaacaagc gggaacttgt ccgtcagacg tcatcaacaa agtagaaggc    600
ggcggtccgt gtcgtctggt tgaacgcttc atgaccgaac tgagcgagta ttttgaggat    660
atccaaattg tccatatcaa tgccggcaaa tggaaaaaca tcgtagacaa attcaatatt    720
ctgaacgtgc cgaccctggt atatctgaaa gatggccgtg aggttggacg ccaaaacctg    780
attcgttcta agaagagat tctgaaaaaa ctgaaagagc tgcaggagta a              831
```

<210> SEQ ID NO 31
<211> LENGTH: 387
<212> TYPE: PRT
<213> ORGANISM: Artificial
<220> FEATURE:
<223> OTHER INFORMATION: PADRE2x PfTrx 11mer

<400> SEQUENCE: 31

```
Met Arg Gly Asp Gly Ala Lys Phe Val Ala Ala Trp Thr Leu Lys Ala
1               5                   10                  15

Ala Ala Gly Pro Gly Pro Gly Met Ile Ile Glu Tyr Asp Gly Glu Ile
                20                  25                  30

Asp Phe Thr Lys Gly Arg Val Val Leu Trp Phe Ser Ile Pro Gly Cys
            35                  40                  45

Gly Pro Lys Thr Cys Lys Gln Ala Gly Thr Cys Pro Pro Asp Ile Ile
        50                  55                  60

Pro Lys Val Glu Gly Gly Pro Lys Thr Cys Lys Gln Ser Gly Thr
65                  70                  75                  80

Cys Pro Pro Asp Val Val Pro Lys Val Glu Gly Gly Pro Gln Thr
                85                  90                  95

Cys Lys Ala Ala Gly Thr Cys Pro Ser Asp Val Ile Pro Lys Ile Glu
            100                 105                 110

His Gly Gly Pro Gln Thr Cys Lys Ala Thr Gly Thr Cys Pro Pro Asp
        115                 120                 125

Val Ile Pro Lys Val Glu Gly Gly Pro Arg Thr Cys Lys Ala Ala
    130                 135                 140

Gly Thr Cys Pro Pro Asp Val Ile Pro Lys Val Glu Gly Gly Gly Pro
145                 150                 155                 160

Arg Thr Cys Lys Gln Ser Gly Thr Cys Pro Pro Asp Val Val Asp Lys
                165                 170                 175

Val Glu Gly Gly Gly Pro Arg Thr Cys Lys Gln Ser Gly Thr Cys Pro
            180                 185                 190

Pro Asp Val Ile Asn Lys Val Glu Gly Gly Gly Pro Ser Thr Cys Lys
        195                 200                 205

Ala Ala Gly Thr Cys Pro Pro Asp Val Val Asn Lys Val Glu Gly Gly
    210                 215                 220

Gly Pro Lys Thr Cys Lys Leu Ser Gly Thr Cys Pro Glu Asp Val Val
225                 230                 235                 240

Asn Lys Ile Glu Gln Gly Gly Pro Lys Thr Cys Lys Gln Ala Gly Thr
                245                 250                 255

Cys Pro Ser Asp Val Ile Asn Lys Val Glu Gly Gly Gly Pro Ser Thr
            260                 265                 270

Cys Lys Ala Ala Gly Thr Cys Pro Pro Asp Val Ile Pro Lys Val Lys
```

```
            275                 280                 285
Gly Gly Gly Pro Cys Arg Leu Val Glu Arg Phe Met Thr Glu Leu Ser
        290                 295                 300
Glu Tyr Phe Glu Asp Ile Gln Ile Val His Ile Asn Ala Gly Lys Trp
305                 310                 315                 320
Lys Asn Ile Val Asp Lys Phe Asn Ile Leu Asn Val Pro Thr Leu Val
                325                 330                 335
Tyr Leu Lys Asp Gly Arg Glu Val Gly Arg Gln Asn Leu Ile Arg Ser
            340                 345                 350
Lys Glu Glu Ile Leu Lys Lys Leu Lys Glu Leu Gln Glu Gly Pro Gly
        355                 360                 365
Pro Gly Ala Lys Phe Val Ala Ala Trp Thr Leu Lys Ala Ala Ala Gly
    370                 375                 380
Arg Gly Asp
385

<210> SEQ ID NO 32
<211> LENGTH: 1164
<212> TYPE: DNA
<213> ORGANISM: Artificial
<220> FEATURE:
<223> OTHER INFORMATION: PADRE2x PfTrx 11mer coding

<400> SEQUENCE: 32
atgcgcggcg atggcgccaa attcgttgcg gcatggaccc tgaaagcggc agcaggccct      60
ggaccgggta tgattatcga gtatgacggc gaaatcgact tcaccaaagg tcgtgttgta     120
ctgtggttta gcattccggg atgcggtccg aagacgtgca acaagcggg cacctgtccg      180 cccgatatta tcccgaaagt cgagggtggt gggccgaaaa cgtgcaaaca gtctggaaca     240
tgcccgccgg atgtggtgcc gaaagtggaa ggaggaggtc cgcaaacgtg caaagcagca     300
gggacctgtc cgtcagatgt gattccgaag attgaacatg gtgggccaca gacctgtaaa     360
gccaccggca cgtgtccgcc agacgtaatc cctaaagtcg aaggtggtgg ccctcgtacg     420
tgcaaagctg cgggcacatg ccctccggat gttattccga agtagaaggg cggcggccca     480
cgcacttgca aacagagtgg tacctgcccg ccggacgtcg tggataaagt tgaaggcggt     540
ggtcctcgca cgtgcaagca aagcggcaca tgcccacccg acgtaatcaa taaggtcgaa     600
ggcggtgggc atcgacttg taaggcggcc gggacttgtc cgccagatgt ggttaacaaa     660
gtggaaggcg gcggacctaa aacttgcaaa ctgagtggaa cctgtccgga ggatgtagtc     720
aacaaaatcg aacagggcgg cccgaaaacc tgtaaacaag caggcacctg tccatcggat     780
gtgattaaca agttgaaggt ggtggtccg agcacgtgta agccgctgg tacatgccct      840 cccgatgtta tccccaaagt taaaggcggc ggtccgtgtc gtctggttga acgcttcatg     900
accgaactga gcgagtattt tgaggatatc caaattgtcc atatcaatgc cggcaaatgg     960
aaaaacatcg tagacaaatt caatattctg aacgtgccga ccctggtata tctgaaagat    1020
ggccgtgagg ttggacgcca aaacctgatt cgttctaaag aagagattct gaaaaaactg    1080
aaagagctgc aggagggtcc gggtccaggg gcgaagtttg tggccgcttg acgttaaaa     1140 gccgctgcgg ggcgtgggga ctaa                                            1164

<210> SEQ ID NO 33
<211> LENGTH: 387
<212> TYPE: PRT
<213> ORGANISM: Artificial
<220> FEATURE:
```

<223> OTHER INFORMATION: (RGD_PADRE)2x_PfTrx 11mer

<400> SEQUENCE: 33

Met Arg Gly Asp Gly Ala Lys Phe Val Ala Ala Trp Thr Leu Lys Ala
1               5                   10                  15

Ala Ala Gly Pro Gly Pro Gly Met Ile Ile Glu Tyr Asp Gly Glu Ile
            20                  25                  30

Asp Phe Thr Lys Gly Arg Val Val Leu Trp Phe Ser Ile Pro Gly Cys
        35                  40                  45

Gly Pro Lys Thr Cys Lys Gln Ala Gly Thr Cys Pro Pro Asp Ile Ile
    50                  55                  60

Pro Lys Val Glu Gly Gly Pro Lys Thr Cys Lys Gln Ser Gly Thr
65                  70                  75                  80

Cys Pro Pro Asp Val Val Pro Lys Val Glu Gly Gly Pro Gln Thr
                85                  90                  95

Cys Lys Ala Ala Gly Thr Cys Pro Ser Asp Val Ile Pro Lys Ile Glu
            100                 105                 110

His Gly Gly Pro Gln Thr Cys Lys Ala Thr Gly Thr Cys Pro Pro Asp
        115                 120                 125

Val Ile Pro Lys Val Glu Gly Gly Pro Arg Thr Cys Lys Ala Ala
        130                 135                 140

Gly Thr Cys Pro Pro Asp Val Ile Pro Lys Val Glu Gly Gly Pro
145                 150                 155                 160

Arg Thr Cys Lys Gln Ser Gly Thr Cys Pro Pro Asp Val Val Asp Lys
            165                 170                 175

Val Glu Gly Gly Gly Pro Arg Thr Cys Lys Gln Ser Gly Thr Cys Pro
        180                 185                 190

Pro Asp Val Ile Asn Lys Val Glu Gly Gly Pro Ser Thr Cys Lys
        195                 200                 205

Ala Ala Gly Thr Cys Pro Pro Asp Val Val Asn Lys Val Glu Gly Gly
    210                 215                 220

Gly Pro Lys Thr Cys Lys Leu Ser Gly Thr Cys Pro Glu Asp Val Val
225                 230                 235                 240

Asn Lys Ile Glu Gln Gly Gly Pro Lys Thr Cys Lys Gln Ala Gly Thr
            245                 250                 255

Cys Pro Ser Asp Val Ile Asn Lys Val Glu Gly Gly Pro Ser Thr
        260                 265                 270

Cys Lys Ala Ala Gly Thr Cys Pro Pro Asp Val Ile Pro Lys Val Lys
        275                 280                 285

Gly Gly Gly Pro Cys Arg Leu Val Glu Arg Phe Met Thr Glu Leu Ser
        290                 295                 300

Glu Tyr Phe Glu Asp Ile Gln Ile Val His Ile Asn Ala Gly Lys Trp
305                 310                 315                 320

Lys Asn Ile Val Asp Lys Phe Asn Ile Leu Asn Val Pro Thr Leu Val
            325                 330                 335

Tyr Leu Lys Asp Gly Arg Glu Val Gly Arg Gln Asn Leu Ile Arg Ser
        340                 345                 350

Lys Glu Glu Ile Leu Lys Lys Leu Lys Glu Leu Gln Glu Gly Pro Gly
        355                 360                 365

Pro Gly Ala Lys Phe Val Ala Ala Trp Thr Leu Lys Ala Ala Ala Gly
    370                 375                 380

Arg Gly Asp
385

<210> SEQ ID NO 34
<211> LENGTH: 321
<212> TYPE: PRT
<213> ORGANISM: Artificial
<220> FEATURE:
<223> OTHER INFORMATION: PADRE2x PfTrx 8mer

<400> SEQUENCE: 34

```
Met Arg Gly Asp Gly Ala Lys Phe Val Ala Ala Trp Thr Leu Lys Ala
1               5                   10                  15

Ala Ala Gly Pro Gly Pro Gly Met Ile Ile Glu Tyr Asp Gly Glu Ile
            20                  25                  30

Asp Phe Thr Lys Gly Arg Val Val Leu Trp Phe Ser Ile Pro Gly Cys
        35                  40                  45

Gly Pro Lys Thr Cys Lys Gln Ala Gly Thr Cys Pro Pro Asp Ile Ile
    50                  55                  60

Pro Lys Val Glu Gly Gly Pro Lys Thr Cys Lys Gln Ser Gly Thr
65                  70                  75                  80

Cys Pro Pro Asp Val Val Pro Lys Val Glu Gly Gly Pro Gln Thr
                85                  90                  95

Cys Lys Ala Ala Gly Thr Cys Pro Ser Asp Val Ile Pro Lys Ile Glu
            100                 105                 110

His Gly Gly Pro Gln Thr Cys Lys Ala Thr Gly Thr Cys Pro Pro Asp
        115                 120                 125

Val Ile Pro Lys Val Glu Gly Gly Pro Arg Thr Cys Lys Ala Ala
130                 135                 140

Gly Thr Cys Pro Pro Asp Val Ile Pro Lys Val Glu Gly Gly Pro
145                 150                 155                 160

Gln Thr Cys Lys Leu Thr Gly Thr Cys Pro Pro Asp Val Ile Pro Lys
                165                 170                 175

Val Glu His Gly Gly Pro Ser Thr Cys Lys Ala Ala Gly Thr Cys Pro
            180                 185                 190

Pro Asp Val Val Asn Lys Val Glu Gly Gly Pro Lys Thr Cys Lys
        195                 200                 205

Gln Ala Gly Thr Cys Pro Ser Asp Val Ile Asn Lys Val Glu Gly Gly
    210                 215                 220

Gly Pro Cys Arg Leu Val Glu Arg Phe Met Thr Glu Leu Ser Glu Tyr
225                 230                 235                 240

Phe Glu Asp Ile Gln Ile Val His Ile Asn Ala Gly Lys Trp Lys Asn
                245                 250                 255

Ile Val Asp Lys Phe Asn Ile Leu Asn Val Pro Thr Leu Val Tyr Leu
            260                 265                 270

Lys Asp Gly Arg Glu Val Gly Arg Gln Asn Leu Ile Arg Ser Lys Glu
        275                 280                 285

Glu Ile Leu Lys Lys Leu Lys Glu Leu Gln Glu Gly Pro Gly Pro Gly
    290                 295                 300

Ala Lys Phe Val Ala Ala Trp Thr Leu Lys Ala Ala Gly Arg Gly
305                 310                 315                 320

Asp
```

<210> SEQ ID NO 35
<211> LENGTH: 966
<212> TYPE: DNA
<213> ORGANISM: Artificial
<220> FEATURE:
<223> OTHER INFORMATION: PADRE2x PfTrx 8mer coding

<400> SEQUENCE: 35

```
atgcgcggcg atggcgccaa attcgttgcg gcatggaccc tgaaagcggc agcaggccct    60
ggaccgggta tgattatcga gtatgacggc gaaatcgact tcaccaaagg tcgtgttgta   120
ctgtggttta gcattccggg atgcggtccg aagacctgta acaggccgg acttgccca   180
ccggatatta ttccaaaggt agaaggtggt ggacccaaaa cgtgcaaaca agcgggacg   240
tgcccaccag acgtggtgcc caaagttgaa ggcggcggc cgcaaacgtg taaggccgct   300
ggtacgtgcc cgagtgatgt tattccgaaa attgaacatg gtggtccaca gacctgtaaa   360
gcgaccggca catgcccgcc ggatgtgatt cctaaagtgg aaggtggagg ccctcgtaca   420
tgcaaggcgg ctggtacatg cccgcctgat gtcatcccga agtcgaagg tggcgggccg   480
cagacgtgca agttgaccgg cacctgtccg ccggatgtta tcccgaaagt tgagcatggc   540
ggcccgtcta cgtgcaaagc agcagggacc tgtccgcctg atgtcgtaaa caaagtcgag   600
ggtggcggtc ccaaaaacctg taaacaagcg ggaacttgtc cgtcagacgt catcaacaaa   660
gtagaaggcg gcggtccgtg tcgtctggtt gaacgcttca tgaccgaact gagcgagtat   720
tttgaggata tccaaattgt ccatatcaat gccggcaaat ggaaaaacat cgtagacaaa   780
ttcaatattc tgaacgtgcc gaccctggta tatctgaaag atggccgtga ggttggacgc   840
caaaacctga ttcgttctaa agaagagatt ctgaaaaaac tgaaagagct gcaggagggt   900
ccgggtccag gggcgaagtt tgtggccgct tggacgttaa aagccgctgc ggggcgtggg   960
gactaa                                                               966
```

<210> SEQ ID NO 36
<211> LENGTH: 356
<212> TYPE: PRT
<213> ORGANISM: Artificial
<220> FEATURE:
<223> OTHER INFORMATION: RGD-PADRE-PfTrx(8mer)-IMX

<400> SEQUENCE: 36

```
Met Arg Gly Asp Gly Ala Lys Phe Val Ala Ala Trp Thr Leu Lys Ala
1               5                   10                  15

Ala Ala Gly Pro Gly Pro Gly Met Ile Ile Glu Tyr Asp Gly Glu Ile
                20                  25                  30

Asp Phe Thr Lys Gly Arg Val Val Leu Trp Phe Ser Ile Pro Gly Cys
            35                  40                  45

Gly Pro Lys Thr Cys Lys Gln Ala Gly Thr Cys Pro Pro Asp Ile Ile
        50                  55                  60

Pro Lys Val Glu Gly Gly Pro Lys Thr Cys Lys Gln Ser Gly Thr
65                  70                  75                  80

Cys Pro Pro Asp Val Val Pro Lys Val Glu Gly Gly Pro Gln Thr
                85                  90                  95

Cys Lys Ala Ala Gly Thr Cys Pro Ser Asp Val Ile Pro Lys Ile Glu
                100                 105                 110

His Gly Gly Pro Gln Thr Cys Lys Ala Thr Gly Thr Cys Pro Pro Asp
            115                 120                 125

Val Ile Pro Lys Val Glu Gly Gly Pro Arg Thr Cys Lys Ala Ala
        130                 135                 140

Gly Thr Cys Pro Pro Asp Val Ile Pro Lys Val Glu Gly Gly Pro
145                 150                 155                 160

Gln Thr Cys Lys Leu Thr Gly Thr Cys Pro Pro Asp Val Ile Pro Lys
                165                 170                 175
```

```
Val Glu His Gly Gly Pro Ser Thr Cys Lys Ala Ala Gly Thr Cys Pro
            180                 185                 190

Pro Asp Val Val Asn Lys Val Glu Gly Gly Pro Lys Thr Cys Lys
        195                 200                 205

Gln Ala Gly Thr Cys Pro Ser Asp Val Ile Asn Lys Val Glu Gly Gly
    210                 215                 220

Gly Pro Cys Arg Leu Val Glu Arg Phe Met Thr Glu Leu Ser Glu Tyr
225                 230                 235                 240

Phe Glu Asp Ile Gln Ile Val His Ile Asn Ala Gly Lys Trp Lys Asn
                245                 250                 255

Ile Val Asp Lys Phe Asn Ile Leu Asn Val Pro Thr Leu Val Tyr Leu
            260                 265                 270

Lys Asp Gly Arg Glu Val Gly Arg Gln Asn Leu Ile Arg Ser Lys Glu
        275                 280                 285

Glu Ile Leu Lys Lys Leu Lys Glu Leu Gln Asp Gly Ser Lys Lys Gln
    290                 295                 300

Gly Asp Ala Asp Val Cys Gly Glu Val Ala Tyr Ile Gln Ser Val Val
305                 310                 315                 320

Ser Asp Cys His Val Pro Thr Ala Glu Leu Arg Thr Leu Leu Glu Ile
                325                 330                 335

Arg Lys Leu Phe Leu Glu Ile Gln Lys Leu Lys Val Glu Gly Arg Arg
            340                 345                 350

Arg Arg Arg Ser
        355

<210> SEQ ID NO 37
<211> LENGTH: 1074
<212> TYPE: DNA
<213> ORGANISM: Artificial
<220> FEATURE:
<223> OTHER INFORMATION: RGD-PADRE-PfTrx(8mer)-IMX coding

<400> SEQUENCE: 37
atgcgcggcg atggcgccaa attcgttgcg catggacccc tgaaagcggc agcaggccct     60
ggaccgggta tgattatcga gtatgacggc gaaatcgact tcaccaaagg tcgtgttgta    120
ctgtggttta gcattccggg atgcggtccg aagacctgta acaggccgg gacttgccca    180
ccggatatta ttccaaaggt agaaggtggt ggacccaaaa cgtgcaaaca agcgggacg    240
tgcccaccag acgtggtgcc caaagttgaa ggcggcgggc cgcaaacgtg taaggccgct    300
ggtacgtgcc cgagtgatgt tattccgaaa attgaacatg gtggtccaca gacctgtaaa    360
gcgaccggca catgcccgcc ggatgtgatt cctaaagtgg aaggtggagg ccctcgtaca    420
tgcaaggcgc tggtacatg cccgcctgat gtcatcccga agtcgaagg tggcgggccg    480
cagacgtgca agttgaccgg cacctgtccg ccggatgtta cccgaaagt tgagcatggc    540
ggcccgtcta cgtgcaaagc agcagggacc tgtccgcctg atgtcgtaaa caaagtcgag    600
ggtggcggtc ccaaaacctg taaacaagcg ggaacttgtc cgtcagacgt catcaacaaa    660
gtagaaggcg gcggtccgtg tcgtctggtt gaacgcttca tgaccgaact gagcgagtat    720
tttgaggata tccaaattgt ccatatcaat gccggcaaat ggaaaaacat cgtagacaaa    780
ttcaatattc tgaacgtgcc gaccctggta tatctgaaag atggccgtga ggttggacgc    840
caaaacctga tcgttctaa gaagagatt ctgaaaaaac tgaaagagct gcaggacgga    900
tccaagaaac agggcgatgc cgatgtatgc ggagaagtgg cgtatatcca gtctgtggtc    960
```

```
agtgattgcc atgtgccgac agcggaatta cgcactcttc tggaaattcg caaactgttt    1020
ctggaaattc agaaactgaa ggtagagggt cgtcgtcgtc gccgttcata ataa          1074
```

<210> SEQ ID NO 38
<211> LENGTH: 320
<212> TYPE: PRT
<213> ORGANISM: Artificial
<220> FEATURE:
<223> OTHER INFORMATION: (RGD_PADRE)2x_PfTrx 8mer

<400> SEQUENCE: 38

```
Arg Gly Asp Gly Ala Lys Phe Val Ala Ala Trp Thr Leu Lys Ala Ala
1               5                   10                  15

Ala Gly Pro Gly Pro Gly Met Ile Ile Glu Tyr Asp Gly Glu Ile Asp
            20                  25                  30

Phe Thr Lys Gly Arg Val Val Leu Trp Phe Ser Ile Pro Gly Cys Gly
        35                  40                  45

Pro Lys Thr Cys Lys Gln Ala Gly Thr Cys Pro Pro Asp Ile Ile Pro
    50                  55                  60

Lys Val Glu Gly Gly Gly Pro Lys Thr Cys Lys Gln Ser Gly Thr Cys
65                  70                  75                  80

Pro Pro Asp Val Val Pro Lys Val Glu Gly Gly Pro Gln Thr Cys
                85                  90                  95

Lys Ala Ala Gly Thr Cys Pro Ser Asp Val Ile Pro Lys Ile Glu His
                100                 105                 110

Gly Gly Pro Gln Thr Cys Lys Ala Thr Gly Thr Cys Pro Pro Asp Val
            115                 120                 125

Ile Pro Lys Val Glu Gly Gly Pro Arg Thr Cys Lys Ala Ala Gly
        130                 135                 140

Thr Cys Pro Pro Asp Val Ile Pro Lys Val Glu Gly Gly Pro Gln
145                 150                 155                 160

Thr Cys Lys Leu Thr Gly Thr Cys Pro Pro Asp Val Ile Pro Lys Val
                165                 170                 175

Glu His Gly Gly Pro Ser Thr Cys Lys Ala Ala Gly Thr Cys Pro Pro
            180                 185                 190

Asp Val Val Asn Lys Val Glu Gly Gly Gly Pro Lys Thr Cys Lys Gln
        195                 200                 205

Ala Gly Thr Cys Pro Ser Asp Val Ile Asn Lys Val Glu Gly Gly Gly
    210                 215                 220

Pro Cys Arg Leu Val Glu Arg Phe Met Thr Glu Leu Ser Glu Tyr Phe
225                 230                 235                 240

Glu Asp Ile Gln Ile Val His Ile Asn Ala Gly Lys Trp Lys Asn Ile
                245                 250                 255

Val Asp Lys Phe Asn Ile Leu Asn Val Pro Thr Leu Val Tyr Leu Lys
            260                 265                 270

Asp Gly Arg Glu Val Gly Arg Gln Asn Leu Ile Arg Ser Lys Glu Glu
        275                 280                 285

Ile Leu Lys Lys Leu Lys Glu Leu Gln Glu Gly Pro Gly Pro Gly Ala
    290                 295                 300

Lys Phe Val Ala Ala Trp Thr Leu Lys Ala Ala Ala Gly Arg Gly Asp
305                 310                 315                 320
```

<210> SEQ ID NO 39
<211> LENGTH: 374
<212> TYPE: PRT
<213> ORGANISM: Artificial

<220> FEATURE:
<223> OTHER INFORMATION: RGD-PADRE-PfTrx(8mer)-PADRE-IMX

<400> SEQUENCE: 39

```
Met Arg Gly Asp Gly Ala Lys Phe Val Ala Ala Trp Thr Leu Lys Ala
1               5                   10                  15
Ala Ala Gly Pro Gly Pro Gly Met Ile Ile Glu Tyr Asp Gly Glu Ile
                20                  25                  30
Asp Phe Thr Lys Gly Arg Val Val Leu Trp Phe Ser Ile Pro Gly Cys
            35                  40                  45
Gly Pro Lys Thr Cys Lys Gln Ala Gly Thr Cys Pro Pro Asp Ile Ile
        50                  55                  60
Pro Lys Val Glu Gly Gly Pro Lys Thr Cys Lys Gln Ser Gly Thr
65                  70                  75                  80
Cys Pro Pro Asp Val Pro Lys Val Glu Gly Gly Pro Gln Thr
                85                  90                  95
Cys Lys Ala Ala Gly Thr Cys Pro Ser Asp Val Ile Pro Lys Ile Glu
                100                 105                 110
His Gly Gly Pro Gln Thr Cys Lys Ala Thr Gly Thr Cys Pro Pro Asp
            115                 120                 125
Val Ile Pro Lys Val Glu Gly Gly Pro Arg Thr Cys Lys Ala Ala
130                 135                 140
Gly Thr Cys Pro Pro Asp Val Ile Pro Lys Val Glu Gly Gly Pro
145                 150                 155                 160
Gln Thr Cys Lys Leu Thr Gly Thr Cys Pro Pro Asp Val Ile Pro Lys
                165                 170                 175
Val Glu His Gly Gly Pro Ser Thr Cys Lys Ala Ala Gly Thr Cys Pro
                180                 185                 190
Pro Asp Val Val Asn Lys Val Glu Gly Gly Pro Lys Thr Cys Lys
            195                 200                 205
Gln Ala Gly Thr Cys Pro Ser Asp Val Ile Asn Lys Val Glu Gly Gly
210                 215                 220
Gly Pro Cys Arg Leu Val Glu Arg Phe Met Thr Glu Leu Ser Glu Tyr
225                 230                 235                 240
Phe Glu Asp Ile Gln Ile Val His Ile Asn Ala Gly Lys Trp Lys Asn
                245                 250                 255
Ile Val Asp Lys Phe Asn Ile Leu Asn Val Pro Thr Leu Val Tyr Leu
            260                 265                 270
Lys Asp Gly Arg Glu Val Gly Arg Gln Asn Leu Ile Arg Ser Lys Glu
        275                 280                 285
Glu Ile Leu Lys Lys Leu Lys Glu Leu Gln Asp Gly Ser Gly Pro Gly
    290                 295                 300
Ala Lys Phe Val Ala Ala Trp Thr Leu Lys Ala Ala Gly Ser Lys
305                 310                 315                 320
Lys Gln Gly Asp Ala Asp Val Cys Gly Glu Val Ala Tyr Ile Gln Ser
                325                 330                 335
Val Val Ser Asp Cys His Val Pro Thr Ala Glu Leu Arg Thr Leu Leu
                340                 345                 350
Glu Ile Arg Lys Leu Phe Leu Glu Ile Gln Lys Leu Lys Val Glu Gly
            355                 360                 365
Arg Arg Arg Arg Arg Ser
    370
```

<210> SEQ ID NO 40

<211> LENGTH: 1128
<212> TYPE: DNA
<213> ORGANISM: Artificial
<220> FEATURE:
<223> OTHER INFORMATION: RGD-PADRE-PfTrx(8mer)-PADRE-IMX coding

<400> SEQUENCE: 40

```
atgcgcggcg atggcgccaa attcgttgcg gcatggaccc tgaaagcggc agcaggccct      60
ggaccgggta tgattatcga gtatgacggc gaaatcgact tcaccaaagg tcgtgttgta     120
ctgtggttta gcattccggg atgcggtccg aagacctgta acaggccgg gacttgccca     180
ccggatatta ttccaaaggt agaaggtggt ggacccaaaa cgtgcaaaca agcgggacg     240
tgcccaccag acgtggtgcc caaagttgaa ggcggcgggc cgcaaacgtg taaggccgct     300
ggtacgtgcc cgagtgatgt tattccgaaa attgaacatg gtggtccaca gacctgtaaa     360
gcgaccggca catgcccgcc ggatgtgatt cctaaagtgg aaggtggagg ccctcgtaca     420
tgcaaggcgg ctggtacatg cccgcctgat gtcatcccga agtcgaagg tggcgggccg     480
cagacgtgca agttgaccgg cacctgtccg ccggatgtta tcccgaaagt tgagcatggc     540
ggcccgtcta cgtgcaaagc agcagggacc tgtccgcctg atgtcgtaaa caaagtcgag     600
ggtggcggtc ccaaaacctg taaacaagcg ggaacttgtc cgtcagacgt catcaacaaa     660
gtagaaggcg gcggtccgtg tcgtctggtt gaacgcttca tgaccgaact gagcgagtat     720
tttgaggata tccaaattgt ccatatcaat gccggcaaat ggaaaaacat cgtagacaaa     780
ttcaatattc tgaacgtgcc gaccctggta tatctgaaag atggccgtga ggttggacgc     840
caaaaacctga ttcgttctaa agaagagatt ctgaaaaaac tgaaagagct gcaggacgga     900
tccggtccag gggcgaagtt tgtggccgct tggacgttaa aagccgctgc cggatccaag     960
aaacagggcg atgccgatgt atgcggagaa gtggcgtata tccagtctgt ggtcagtgat    1020
tgccatgtgc cgacagcgga attacgcact cttctggaaa ttcgcaaact gtttctggaa    1080
attcagaaac tgaaggtaga gggtcgtcgt cgtcgccgtt cataataa                 1128
```

<210> SEQ ID NO 41
<211> LENGTH: 399
<212> TYPE: PRT
<213> ORGANISM: Artificial
<220> FEATURE:
<223> OTHER INFORMATION: PfTrx 11mer-IMX313T

<400> SEQUENCE: 41

```
Met Ile Ile Glu Tyr Asp Gly Glu Ile Asp Phe Thr Lys Gly Arg Val
1               5                  10                  15

Val Leu Trp Phe Ser Ile Pro Gly Cys Gly Pro Lys Thr Cys Lys Gln
            20                  25                  30

Ala Gly Thr Cys Pro Pro Asp Ile Pro Lys Val Glu Gly Gly Gly
        35                  40                  45

Pro Lys Thr Cys Lys Gln Ser Gly Thr Cys Pro Pro Asp Val Val Pro
    50                  55                  60

Lys Val Glu Gly Gly Gly Pro Gln Thr Cys Lys Ala Ala Gly Thr Cys
65                  70                  75                  80

Pro Ser Asp Val Ile Pro Lys Ile Glu His Gly Gly Pro Gln Thr Cys
                85                  90                  95

Lys Ala Thr Gly Thr Cys Pro Pro Asp Val Ile Pro Lys Val Glu Gly
            100                 105                 110

Gly Gly Pro Arg Thr Cys Lys Ala Ala Gly Thr Cys Pro Pro Asp Val
        115                 120                 125
```

```
Ile Pro Lys Val Glu Gly Gly Pro Arg Thr Cys Lys Gln Ser Gly
            130                 135                 140

Thr Cys Pro Pro Asp Val Val Asp Lys Val Glu Gly Gly Pro Arg
145                 150                 155                 160

Thr Cys Lys Gln Ser Gly Thr Cys Pro Pro Asp Val Ile Asn Lys Val
                165                 170                 175

Glu Gly Gly Pro Ser Thr Cys Lys Ala Ala Gly Thr Cys Pro Pro
            180                 185                 190

Asp Val Asn Lys Val Glu Gly Gly Pro Lys Thr Cys Lys Leu
                195                 200                 205

Ser Gly Thr Cys Pro Glu Asp Val Val Asn Lys Ile Glu Gln Gly Gly
            210                 215                 220

Pro Lys Thr Cys Lys Gln Ala Gly Thr Cys Pro Ser Asp Val Ile Asn
225                 230                 235                 240

Lys Val Glu Gly Gly Pro Ser Thr Cys Lys Ala Ala Gly Thr Cys
                245                 250                 255

Pro Pro Asp Val Ile Pro Lys Val Lys Gly Gly Pro Cys Arg Leu
                260                 265                 270

Val Glu Arg Phe Met Thr Glu Leu Ser Glu Tyr Phe Glu Asp Ile Gln
                275                 280                 285

Ile Val His Ile Asn Ala Gly Lys Trp Lys Asn Ile Val Asp Lys Phe
            290                 295                 300

Asn Ile Leu Asn Val Pro Thr Leu Val Tyr Leu Lys Asp Gly Arg Glu
305                 310                 315                 320

Val Gly Arg Gln Asn Leu Ile Arg Ser Lys Glu Ile Leu Lys Lys
                325                 330                 335

Leu Lys Glu Leu Gln Glu Gly Ser Lys Lys Gln Gly Asp Ala Asp Val
            340                 345                 350

Cys Gly Glu Val Ala Tyr Ile Gln Ser Val Val Ser Asp Cys His Val
            355                 360                 365

Pro Thr Ala Glu Leu Arg Thr Leu Leu Glu Ile Arg Lys Leu Phe Leu
370                 375                 380

Glu Ile Gln Lys Leu Lys Val Glu Gly Arg Arg Arg Arg Ser
385                 390                 395
```

<210> SEQ ID NO 42
<211> LENGTH: 1203
<212> TYPE: DNA
<213> ORGANISM: Artificial
<220> FEATURE:
<223> OTHER INFORMATION: PfTrx 11mer-IMX313T coding

<400> SEQUENCE: 42

```
atgattatcg agtatgatgg cgagattgac ttcaccaaag gtcgcgtcgt actgtggttt      60
agcattcccg ttgcggtcc  gaagacgtgc aaacaagcgg gcacctgtcc gcccgatatt     120
atcccgaaag tcgagggtgg tgggccgaaa acgtgcaaac agtctggaac atgcccgccg     180
gatgtggtgc cgaaagtgga aggaggaggt ccgcaaacgt gcaaagcagc agggacctgt     240
ccgtcagatg tgattccgaa gattgaacat ggtgggccac agacctgtaa agccaccggc     300
acgtgtccgc cagacgtaat ccctaaagtc gaaggtggtg ccctcgtac  gtgcaaagct     360 gcgggcacat gcctccgga  tgttattccg aaagtagaag gcggcggccc acgcacttgc     420
aaacagagtg gtacctgccc gccggacgtc gtggataaag ttgaaggcgg tggtcctcgc     480
acgtgcaagc aaagcggcac atgcccaccc gacgtaatca ataaggtcga aggcggtggg     540
```

```
ccatcgactt gtaaggcggc cgggacttgt ccgccagatg tggttaacaa agtggaaggc    600
ggcggaccta aaacttgcaa actgagtgga acctgtccgg aggatgtagt caacaaaatc    660
gaacagggcg gcccgaaaac ctgtaaacaa gcaggcacct gtccatcgga tgtgattaac    720
aaagttgaag tggtggtcc gagcacgtgt aaagccgctg gtacatgccc tcccgatgtt    780
atccccaaag ttaaaggcgg cggtccgtgc cgtcttgtgg aacggtttat gaccgagtta    840
tccgaatact tcgaggacat tcagatcgtg cacattaatg cgggcaaatg gaagaacatc    900
gttgacaaat tcaacatcct caatgtccct accctggttt acctcaaaga tggtcgcgaa    960
gttgggcgcc agaacttgat tcgcagcaaa gaagagattc tgaagaaact gaaagaattg    1020
caagaaggct cgaagaaaca gggcgatgcc gatgtatgcg agaagtggc gtatatccag    1080 tctgtggtca gtgattgcca tgtgccgaca gcggaattac gcactcttct ggaaattcgc    1140
aaactgtttc tggaaattca gaaactgaag gtagagggtc gtcgtcgtcg ccgttcataa    1200
taa                                                                  1203
```

<210> SEQ ID NO 43
<211> LENGTH: 333
<212> TYPE: PRT
<213> ORGANISM: Artificial
<220> FEATURE:
<223> OTHER INFORMATION: PfTrx 8mer-IMX313T

<400> SEQUENCE: 43

```
Met Ile Ile Glu Tyr Asp Gly Glu Ile Asp Phe Thr Lys Gly Arg Val
1               5                   10                  15

Val Leu Trp Phe Ser Ile Pro Gly Cys Gly Pro Lys Thr Cys Lys Gln
            20                  25                  30

Ala Gly Thr Cys Pro Pro Asp Ile Ile Pro Lys Val Glu Gly Gly Gly
        35                  40                  45

Pro Lys Thr Cys Lys Gln Ser Gly Thr Cys Pro Pro Asp Val Val Pro
    50                  55                  60

Lys Val Glu Gly Gly Gly Pro Gln Thr Cys Lys Ala Ala Gly Thr Cys
65                  70                  75                  80

Pro Ser Asp Val Ile Pro Lys Ile Glu His Gly Gly Pro Gln Thr Cys
                85                  90                  95

Lys Ala Thr Gly Thr Cys Pro Pro Asp Val Ile Pro Lys Val Glu Gly
            100                 105                 110

Gly Gly Pro Arg Thr Cys Lys Ala Ala Gly Thr Cys Pro Pro Asp Val
        115                 120                 125

Ile Pro Lys Val Glu Gly Gly Pro Gln Thr Cys Lys Leu Thr Gly
    130                 135                 140

Thr Cys Pro Pro Asp Val Ile Pro Lys Val Glu His Gly Gly Pro Ser
145                 150                 155                 160

Thr Cys Lys Ala Ala Gly Thr Cys Pro Pro Asp Val Val Asn Lys Val
                165                 170                 175

Glu Gly Gly Gly Pro Lys Thr Cys Lys Gln Ala Gly Thr Cys Pro Ser
            180                 185                 190

Asp Val Ile Asn Lys Val Glu Gly Gly Pro Cys Arg Leu Val Glu
        195                 200                 205

Arg Phe Met Thr Glu Leu Ser Glu Tyr Phe Glu Asp Ile Gln Ile Val
    210                 215                 220

His Ile Asn Ala Gly Lys Trp Lys Asn Ile Val Asp Lys Phe Asn Ile
225                 230                 235                 240
```

Leu Asn Val Pro Thr Leu Val Tyr Leu Lys Asp Gly Arg Glu Val Gly
            245                 250                 255

Arg Gln Asn Leu Ile Arg Ser Lys Glu Ile Leu Lys Lys Leu Lys
        260                 265                 270

Glu Leu Gln Glu Gly Ser Lys Lys Gln Gly Asp Ala Asp Val Cys Gly
        275                 280                 285

Glu Val Ala Tyr Ile Gln Ser Val Val Ser Asp Cys His Val Pro Thr
        290                 295                 300

Ala Glu Leu Arg Thr Leu Leu Glu Ile Arg Lys Leu Phe Leu Glu Ile
305                 310                 315                 320

Gln Lys Leu Lys Val Glu Gly Arg Arg Arg Arg Ser
            325                 330

<210> SEQ ID NO 44
<211> LENGTH: 1005
<212> TYPE: DNA
<213> ORGANISM: Artificial
<220> FEATURE:
<223> OTHER INFORMATION: PfTrx 8mer-IMX313T coding

<400> SEQUENCE: 44
atgattatcg agtatgatgg cgagattgac ttcaccaaag gtcgcgtcgt actgtggttt    60
agcattcccg gttgcggtcc gaagacctgt aaacaggccg ggacttgccc accggatatt   120
attccaaagg tagaaggtgg tggacccaaa acgtgcaaac aaagcgggac gtgcccacca   180
gacgtggtgc ccaaagttga aggcggcggg ccgcaaacgt gtaaggccgc tggtacgtgc   240
ccgagtgatg ttattccgaa aattgaacat ggtggtccac agacctgtaa agcgaccggc   300
acatgcccgc cggatgtgat tcctaaagtg aaggtggagc ccctcgtac atgcaaggcg   360
gctggtacat gcccgcctga tgtcatcccg aaagtcgaag gtggcgggcc gcagacgtgc   420
aagttgaccg gcacctgtcc gccggatgtt atcccgaaag ttgagcatgg cggcccgtct   480
acgtgcaaag cagcagggac ctgtccgcct gatgtcgtaa acaaagtcga gggtggcggt   540
cccaaaacct gtaaacaagc gggaacttgt ccgtcagacg tcatcaacaa gtagaaggc   600
ggcggtccgt gccgtcttgt ggaacggttt atgaccgagt tatccgaata cttcgaggac   660
attcagatcg tgcacattaa tgcgggcaaa tggaagaaca tcgttgacaa attcaacatc   720
ctcaatgtcc ctaccctggt ttacctcaaa gatggtcgcg aagttgggcg ccagaacttg   780
attcgcagca agaagagat tctgaagaaa ctgaagaat tgcaagaagg ctcgaagaaa    840
cagggcgatg ccgatgtatg cggagaagtg gcgtatatcc agtctgtggt cagtgattgc   900
catgtgccga cagcggaatt acgcactctt ctggaaattc gcaaactgtt tctggaaatt   960
cagaaactga aggtagaggg tcgtcgtcgt cgccgttcat aataa               1005

<210> SEQ ID NO 45
<211> LENGTH: 109
<212> TYPE: PRT
<213> ORGANISM: Escherichia coli

<400> SEQUENCE: 45

Met Gly Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

```
Glu Tyr Gln Gly Lys Leu Thr Val Ala Lys Leu Asn Ile Asp Gln Asn
         50                  55                  60

Pro Gly Thr Ala Pro Lys Tyr Gly Ile Arg Gly Ile Pro Thr Leu Leu
 65                  70                  75                  80

Leu Phe Lys Asn Gly Glu Val Ala Thr Lys Val Gly Ala Leu Ser
                 85                  90                  95

Lys Gly Gln Leu Lys Glu Phe Leu Asp Ala Asn Leu Ala
            100                 105

<210> SEQ ID NO 46
<211> LENGTH: 330
<212> TYPE: DNA
<213> ORGANISM: Escherichia coli

<400> SEQUENCE: 46
atgggcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
ctgttcaaaa acggtgaagt ggcggcaacc aaagtgggtg cactgtctaa aggtcagttg   300
aaagagttcc tcgacgctaa cctggcgtga                                    330

<210> SEQ ID NO 47
<211> LENGTH: 105
<212> TYPE: PRT
<213> ORGANISM: Mus musculus

<400> SEQUENCE: 47

Met Val Lys Leu Ile Glu Ser Lys Glu Ala Phe Gln Glu Ala Leu Ala
 1               5                  10                  15

Ala Ala Gly Asp Lys Leu Val Val Val Asp Phe Ser Ala Thr Trp Cys
            20                  25                  30

Gly Pro Cys Lys Met Ile Lys Pro Phe Phe His Ser Leu Cys Asp Lys
         35                  40                  45

Tyr Ser Asn Val Val Phe Leu Glu Val Asp Val Asp Asp Cys Gln Asp
     50                  55                  60

Val Ala Ala Asp Cys Glu Val Lys Cys Met Pro Thr Phe Gln Phe Tyr
 65                  70                  75                  80

Lys Lys Gly Gln Lys Val Gly Glu Phe Ser Gly Ala Asn Lys Glu Lys
                 85                  90                  95

Leu Glu Ala Ser Ile Thr Glu Tyr Ala
            100                 105

<210> SEQ ID NO 48
<211> LENGTH: 318
<212> TYPE: DNA
<213> ORGANISM: Mus musculus

<400> SEQUENCE: 48
atggtgaagc tgatcgagag caaggaagct tttcaggagg ccctggccgc cgcgggagac    60
aagcttgtcg tggtggactt ctctgctacg tggtgcggtc cgtgcaaaat gatcaagccc   120
ttcttccatt ccctctgtga caagtattcc aatgtggtgt tccttgaagt ggatgtggat   180
gactgccagg atgttgctgc agactgtgaa gtcaaatgca tgccgacctt ccagttttat   240
aaaaagggtc aaaaggtggg ggagttctcc ggtgctaaca ggaaaaagct tgaagcctct   300
```
attactgaat atgcctaa                                              318

<210> SEQ ID NO 49
<211> LENGTH: 105
<212> TYPE: PRT
<213> ORGANISM: Homo sapiens

<400> SEQUENCE: 49

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
            20                  25                  30

Gly Pro Cys Lys Met Ile Lys Pro Phe Phe His Ser Leu Ser Glu Lys
        35                  40                  45

Tyr Ser Asn Val Ile Phe Leu Glu Val Asp Val Asp Cys Gln Asp
    50                  55                  60

Val Ala Ser Glu Cys Glu Val Lys Cys Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val
            100                 105

<210> SEQ ID NO 50
<211> LENGTH: 318
<212> TYPE: DNA
<213> ORGANISM: Homo sapiens

<400> SEQUENCE: 50
atggtgaagc agatcgagag caagactgct tttcaggaag ccttggacgc tgcaggtgat    60
aaacttgtag tagttgactt ctcagccacg tggtgtgggc cttgcaaaat gatcaagcct   120
ttctttcatt ccctctctga aaagtattcc aacgtgatat tccttgaagt agatgtggat   180
gactgtcagg atgttgcttc agagtgtgaa gtcaaatgca tgccaacatt ccagtttttt   240
aagaagggac aaaaggtggg tgaattttct ggagccaata ggaaaagct tgaagccacc   300 attaatgaat tagtctaa                                              318

<210> SEQ ID NO 51
<211> LENGTH: 138
<212> TYPE: PRT
<213> ORGANISM: Methanosaeta thermophila

<400> SEQUENCE: 51

Met Asp Glu Leu Asp Glu Ile Arg Arg Lys Lys Leu Glu Glu Leu Lys
1               5                   10                  15

Arg Glu Leu Ala Ala Arg Ser Gln Gly Thr Pro Thr Ile Glu Tyr Pro
            20                  25                  30

Asp Arg Pro Val Leu Val Thr Asp Ser Ser Ile Asp Ala Gly Ile Arg
        35                  40                  45

Gln Tyr Pro Val Phe Val Val Asp Cys Trp Ala Glu Trp Cys Gly Pro
    50                  55                  60

Cys Arg Ala Ile Ala Pro Val Ile Asp Glu Met Ala Arg Glu Leu Lys
65                  70                  75                  80

Gly Arg Val Val Phe Gly Lys Leu Asn Val Asp Gln Asn Pro Leu Thr
                85                  90                  95

Ser Arg Lys Tyr Gly Ile Thr Ala Ile Pro Thr Leu Leu Val Phe Arg

```
                100             105             110
Asn Gly Arg Leu Val Asp Arg Leu Val Gly Ala Tyr Pro Lys Gln Ile
        115             120             125

Leu Met Ser Arg Val Arg Lys Tyr Leu Asp
    130             135

<210> SEQ ID NO 52
<211> LENGTH: 417
<212> TYPE: DNA
<213> ORGANISM: Methanosaeta thermophila

<400> SEQUENCE: 52
atggacgagc tggacgaaat ccgccgtaaa aaactggaag aactgaaacg tgaactggct      60
gcccgtagtc aaggaacacc gacgatcgag tatcctgacc gccctgtact ggttactgat     120
tctagcattg atgccgggat cgccaatat cctgtctttg tggtggactg ttgggctgaa      180
tggtgcggtc cgtgtcgtgc tattgctccg gtgatcgatg aaatggcccg tgagctgaaa     240
ggacgtgtgg tattcgggaa actgaacgtg gaccaaaatc cgctgacgag tcgtaaatat     300
ggcattaccg ccatccctac actgctggtt ttccgtaacg tcgtctggt tgatcgcctg      360 gttggtgctt atccgaaaca aattctgatg tctcgtgtcc gtaaatatct ggactag        417

<210> SEQ ID NO 53
<211> LENGTH: 100
<212> TYPE: PRT
<213> ORGANISM: Pyrococcus furiosus

<400> SEQUENCE: 53

Met Ile Ile Glu Tyr Asp Gly Glu Ile Asp Phe Thr Lys Gly Arg Val
1               5                   10                  15

Val Leu Trp Phe Ser Ile Pro Gly Cys Gly Pro Cys Arg Leu Val Glu
            20                  25                  30

Arg Phe Met Thr Glu Leu Ser Glu Tyr Phe Glu Asp Ile Gln Ile Val
        35                  40                  45

His Ile Asn Ala Gly Lys Trp Lys Asn Ile Val Asp Lys Phe Asn Ile
    50                  55                  60

Leu Asn Val Pro Thr Leu Val Tyr Leu Lys Asp Gly Arg Glu Val Gly
65                  70                  75                  80

Arg Gln Asn Leu Ile Arg Ser Lys Glu Glu Ile Leu Lys Lys Leu Lys
                85                  90                  95

Glu Leu Gln Glu
            100

<210> SEQ ID NO 54
<211> LENGTH: 303
<212> TYPE: DNA
<213> ORGANISM: Pyrococcus furiosus

<400> SEQUENCE: 54
atgattatcg agtatgacgg cgaaatcgac ttcaccaaag gtcgtgttgt actgtggttt      60
agcattccgg gatgcggtcc gtgtcgtctg gttgaacgct tcatgaccga actgagcgag     120
tattttgagg atatccaaat tgtccatatc aatgccggca atggaaaaaa catcgtagac     180
aaattcaata ttctgaacgt gccgaccctg gtatatctga agatggccg tgaggttgga      240 cgccaaaacc tgattcgttc taaagaagag attctgaaaa aactgaaaga gctgcaggag     300
taa                                                                   303
```

```
<210> SEQ ID NO 55
<211> LENGTH: 259
<212> TYPE: PRT
<213> ORGANISM: Pyrococcus furiosus

<400> SEQUENCE: 55

Met Arg Lys Ser Lys Glu Leu Thr Gly Ile Glu Ala His Ile Asn Asp
1               5                   10                  15

Asn Lys Lys Glu Glu Ser Asn Val Glu Tyr Phe Glu Lys Leu Arg Ser
                20                  25                  30

Ala Leu Leu Asp Gly Val Asn Lys Gly Arg Ser Leu Leu Lys His Leu
            35                  40                  45

Pro Val Thr Arg Ile Glu Gly Gln Ser Phe Arg Val Asp Ile Ile Lys
        50                  55                  60

Phe Glu Asp Gly Val Arg Val Lys Gln Tyr Lys Pro Ile Pro
65                  70                  75                  80

Leu Leu Lys Lys Lys Phe Tyr Val Gly Ile Arg Glu Leu Asn Asp Gly
                85                  90                  95

Thr Tyr Asp Val Ser Ile Ala Thr Lys Ala Gly Glu Leu Leu Val Lys
            100                 105                 110

Asp Glu Glu Ser Leu Val Ile Arg Glu Ile Leu Ser Thr Glu Gly Ile
        115                 120                 125

Lys Lys Met Lys Leu Ser Ser Trp Asp Asn Pro Glu Ala Leu Asn
130                 135                 140

Asp Leu Met Asn Ala Leu Gln Glu Ala Ser Asn Ala Ser Ala Gly Pro
145                 150                 155                 160

Phe Gly Leu Ile Ile Asn Pro Lys Arg Tyr Ala Lys Leu Leu Lys Ile
                165                 170                 175

Tyr Glu Lys Ser Gly Lys Met Leu Val Glu Val Leu Lys Glu Ile Phe
            180                 185                 190

Arg Gly Gly Ile Ile Val Thr Leu Asn Ile Asp Glu Asn Lys Val Ile
        195                 200                 205

Ile Phe Ala Asn Thr Pro Ala Val Leu Asp Val Val Gly Gln Asp
210                 215                 220

Val Thr Leu Gln Glu Leu Gly Pro Glu Gly Asp Asp Val Ala Phe Leu
225                 230                 235                 240

Val Ser Glu Ala Ile Gly Ile Arg Ile Lys Asn Pro Glu Ala Ile Val
                245                 250                 255

Val Leu Glu

<210> SEQ ID NO 56
<211> LENGTH: 174
<212> TYPE: PRT
<213> ORGANISM: Pyrococcus furiosus

<400> SEQUENCE: 56

Met Leu Ser Glu Arg Met Leu Lys Ala Leu Asn Asp Gln Leu Asn Arg
1               5                   10                  15

Glu Leu Tyr Ser Ala Tyr Leu Tyr Phe Ala Met Ala Ala Tyr Phe Glu
                20                  25                  30

Asp Leu Gly Leu Glu Gly Phe Ala Asn Trp Met Lys Ala Gln Ala Glu
            35                  40                  45

Glu Glu Ile Gly His Ala Leu Arg Phe Tyr Asn Tyr Ile Tyr Asp Arg
        50                  55                  60

Asn Gly Arg Val Glu Leu Asp Glu Ile Pro Lys Pro Pro Lys Glu Trp
```

```
              65                  70                  75                  80
Glu Ser Pro Leu Lys Ala Phe Glu Ala Ala Tyr Glu His Lys Phe
                85                  90                  95

Ile Ser Lys Ser Ile Tyr Glu Leu Ala Ala Leu Ala Glu Glu Lys
                100                 105                 110

Asp Tyr Ser Thr Arg Ala Phe Leu Glu Trp Phe Ile Asn Glu Gln Val
                115                 120                 125

Glu Glu Glu Ala Ser Val Lys Lys Ile Leu Asp Lys Leu Lys Phe Ala
    130                 135                 140

Lys Asp Ser Pro Gln Ile Leu Phe Met Leu Asp Lys Glu Leu Ser Ala
145                 150                 155                 160

Arg Ala Pro Lys Leu Pro Gly Leu Leu Met Gln Gly Gly Glu
                165                 170

<210> SEQ ID NO 57
<211> LENGTH: 13
<212> TYPE: PRT
<213> ORGANISM: Artificial
<220> FEATURE:
<223> OTHER INFORMATION: Pan HLA-DR reactive epitope (PADRE)

<400> SEQUENCE: 57

Ala Lys Phe Val Ala Ala Trp Thr Leu Lys Ala Ala Ala
1               5                   10

<210> SEQ ID NO 58
<211> LENGTH: 15
<212> TYPE: PRT
<213> ORGANISM: Artificial
<220> FEATURE:
<223> OTHER INFORMATION: p2p30

<400> SEQUENCE: 58

Gln Tyr Ile Lys Ala Asn Ser Lys Phe Ile Gly Ile Thr Glu Leu
1               5                   10                  15

<210> SEQ ID NO 59
<211> LENGTH: 17
<212> TYPE: PRT
<213> ORGANISM: Artificial
<220> FEATURE:
<223> OTHER INFORMATION: p25

<400> SEQUENCE: 59

Lys Leu Ile Pro Asn Ala Ser Leu Ile Glu Asn Cys Thr Lys Ala Glu
1               5                   10                  15

Leu

<210> SEQ ID NO 60
<211> LENGTH: 55
<212> TYPE: PRT
<213> ORGANISM: Artificial
<220> FEATURE:
<223> OTHER INFORMATION: oligomerization sequence

<400> SEQUENCE: 60

Lys Lys Gln Gly Asp Ala Asp Val Cys Gly Glu Val Ala Tyr Ile Gln
1               5                   10                  15

Ser Val Val Ser Asp Cys His Val Pro Thr Ala Glu Leu Arg Thr Leu
                20                  25                  30

Leu Glu Ile Arg Lys Leu Phe Leu Glu Ile Gln Lys Leu Lys Val Glu
                35                  40                  45
```

```
<210> SEQ ID NO 61
<211> LENGTH: 165
<212> TYPE: DNA
<213> ORGANISM: Artificial
<220> FEATURE:
<223> OTHER INFORMATION: Sequence encoding oligomerization polypeptide
      IMX313T

<400> SEQUENCE: 61
aagaaacagg gcgatgccga tgtatgcgga gaagtggcgt atatccagtc tgtggtcagt    60
gattgccatg tgccgacagc ggaattacgc actcttctgg aaattcgcaa actgtttctg   120
gaaattcaga aactgaaggt agagggtcgt cgtcgtcgcc gttca                   165

<210> SEQ ID NO 62
<211> LENGTH: 189
<212> TYPE: PRT
<213> ORGANISM: Artificial
<220> FEATURE:
<223> OTHER INFORMATION: (RGD_PADRE)1x_PfTrx_HPV16_L2(20-38)3

<400> SEQUENCE: 62
```

Met Arg Gly Asp Gly Ala Lys Phe Val Ala Ala Trp Thr Leu Lys Ala
1               5                   10                  15

Ala Ala Gly Pro Gly Pro Gly Met Ile Ile Glu Tyr Asp Gly Glu Ile
                20                  25                  30

Asp Phe Thr Lys Gly Arg Val Val Leu Trp Phe Ser Ile Pro Gly Cys
            35                  40                  45

Gly Pro Lys Thr Cys Lys Gln Ala Gly Thr Cys Pro Pro Asp Ile Ile
        50                  55                  60

Pro Lys Val Glu Gly Gly Pro Lys Thr Cys Lys Gln Ala Gly Thr
65                  70                  75                  80

Cys Pro Pro Asp Ile Ile Pro Lys Val Glu Gly Gly Pro Lys Thr
                85                  90                  95

Cys Lys Gln Ala Gly Thr Cys Pro Pro Asp Ile Ile Pro Lys Val Glu
            100                 105                 110

Gly Gly Gly Pro Cys Arg Leu Val Glu Arg Phe Met Thr Glu Leu Ser
        115                 120                 125

Glu Tyr Phe Glu Asp Ile Gln Ile Val His Ile Asn Ala Gly Lys Trp
    130                 135                 140

Lys Asn Ile Val Asp Lys Phe Asn Ile Leu Asn Val Pro Thr Leu Val
145                 150                 155                 160

Tyr Leu Lys Asp Gly Arg Glu Val Gly Arg Gln Asn Leu Ile Arg Ser
                165                 170                 175

Lys Glu Glu Ile Leu Lys Lys Leu Lys Glu Leu Gln Glu
            180                 185

```
<210> SEQ ID NO 63
<211> LENGTH: 211
<212> TYPE: PRT
<213> ORGANISM: Artificial
<220> FEATURE:
<223> OTHER INFORMATION: (RGD_PADRE)2x_PfTrx_HPV16_L2(20-38)3

<400> SEQUENCE: 63
```

Met Arg Gly Asp Gly Ala Lys Phe Val Ala Ala Trp Thr Leu Lys Ala
1               5                   10                  15

-continued

Ala Ala Gly Pro Gly Pro Gly Met Ile Ile Glu Tyr Asp Gly Glu Ile
            20                  25                  30

Asp Phe Thr Lys Gly Arg Val Val Leu Trp Phe Ser Ile Pro Gly Cys
        35                  40                  45

Gly Pro Lys Thr Cys Lys Gln Ala Gly Thr Cys Pro Pro Asp Ile Ile
    50                  55                  60

Pro Lys Val Glu Gly Gly Pro Lys Thr Cys Lys Gln Ala Gly Thr
65                  70                  75                  80

Cys Pro Pro Asp Ile Ile Pro Lys Val Glu Gly Gly Pro Lys Thr
                85                  90                  95

Cys Lys Gln Ala Gly Thr Cys Pro Pro Asp Ile Ile Pro Lys Val Glu
            100                 105                 110

Gly Gly Gly Pro Cys Arg Leu Val Glu Arg Phe Met Thr Glu Leu Ser
        115                 120                 125

Glu Tyr Phe Glu Asp Ile Gln Ile Val His Ile Asn Ala Gly Lys Trp
    130                 135                 140

Lys Asn Ile Val Asp Lys Phe Asn Ile Leu Asn Val Pro Thr Leu Val
145                 150                 155                 160

Tyr Leu Lys Asp Gly Arg Glu Val Gly Arg Gln Asn Leu Ile Arg Ser
                165                 170                 175

Lys Glu Glu Ile Leu Lys Lys Leu Lys Glu Leu Gln Glu Gly Pro Gly
            180                 185                 190

Pro Gly Ala Lys Phe Val Ala Ala Trp Thr Leu Lys Ala Ala Ala Gly
        195                 200                 205

Arg Gly Asp
    210

<210> SEQ ID NO 64
<211> LENGTH: 215
<212> TYPE: PRT
<213> ORGANISM: Artificial
<220> FEATURE:
<223> OTHER INFORMATION: (RGD_p2p30)1x_PfTrx_HPV16_L2(20-38)3

<400> SEQUENCE: 64

Met Arg Gly Asp Gly Gln Tyr Ile Lys Ala Asn Ser Lys Phe Ile Gly
1               5                   10                  15

Ile Thr Glu Leu Gly Pro Gly Phe Asn Asn Phe Thr Val Ser Phe Trp
            20                  25                  30

Leu Arg Val Pro Lys Val Ser Ala Ser His Leu Glu Gly Pro Gly Pro
        35                  40                  45

Gly Met Ile Ile Glu Tyr Asp Gly Glu Ile Asp Phe Thr Lys Gly Arg
    50                  55                  60

Val Val Leu Trp Phe Ser Ile Pro Gly Cys Gly Pro Lys Thr Cys Lys
65                  70                  75                  80

Gln Ala Gly Thr Cys Pro Pro Asp Ile Ile Pro Lys Val Glu Gly Gly
                85                  90                  95

Gly Pro Lys Thr Cys Lys Gln Ala Gly Thr Cys Pro Pro Asp Ile Ile
            100                 105                 110

Pro Lys Val Glu Gly Gly Gly Pro Lys Thr Cys Lys Gln Ala Gly Thr
        115                 120                 125

Cys Pro Pro Asp Ile Ile Pro Lys Val Glu Gly Gly Gly Pro Cys Arg
    130                 135                 140

Leu Val Glu Arg Phe Met Thr Glu Leu Ser Glu Tyr Phe Glu Asp Ile
145                 150                 155                 160

```
Gln Ile Val His Ile Asn Ala Gly Lys Trp Lys Asn Ile Val Asp Lys
            165                 170                 175

Phe Asn Ile Leu Asn Val Pro Thr Leu Val Tyr Leu Lys Asp Gly Arg
            180                 185                 190

Glu Val Gly Arg Gln Asn Leu Ile Arg Ser Lys Glu Glu Ile Leu Lys
            195                 200                 205

Lys Leu Lys Glu Leu Gln Glu
            210                 215

<210> SEQ ID NO 65
<211> LENGTH: 263
<212> TYPE: PRT
<213> ORGANISM: Artificial
<220> FEATURE:
<223> OTHER INFORMATION: (RGD_p2p30)2x_PfTrx_HPV16_L2(20-38)3

<400> SEQUENCE: 65

Met Arg Gly Asp Gly Gln Tyr Ile Lys Ala Asn Ser Lys Phe Ile Gly
1               5                   10                  15

Ile Thr Glu Leu Gly Pro Gly Phe Asn Asn Phe Thr Val Ser Phe Trp
            20                  25                  30

Leu Arg Val Pro Lys Val Ser Ala Ser His Leu Glu Gly Pro Gly Pro
            35                  40                  45

Gly Met Ile Ile Glu Tyr Asp Gly Glu Ile Asp Phe Thr Lys Gly Arg
    50                  55                  60

Val Val Leu Trp Phe Ser Ile Pro Gly Cys Gly Pro Lys Thr Cys Lys
65                  70                  75                  80

Gln Ala Gly Thr Cys Pro Pro Asp Ile Ile Pro Lys Val Glu Gly Gly
            85                  90                  95

Gly Pro Lys Thr Cys Lys Gln Ala Gly Thr Cys Pro Pro Asp Ile Ile
            100                 105                 110

Pro Lys Val Glu Gly Gly Gly Pro Lys Thr Cys Lys Gln Ala Gly Thr
            115                 120                 125

Cys Pro Pro Asp Ile Ile Pro Lys Val Glu Gly Gly Gly Pro Cys Arg
    130                 135                 140

Leu Val Glu Arg Phe Met Thr Glu Leu Ser Glu Tyr Phe Glu Asp Ile
145                 150                 155                 160

Gln Ile Val His Ile Asn Ala Gly Lys Trp Lys Asn Ile Val Asp Lys
            165                 170                 175

Phe Asn Ile Leu Asn Val Pro Thr Leu Val Tyr Leu Lys Asp Gly Arg
            180                 185                 190

Glu Val Gly Arg Gln Asn Leu Ile Arg Ser Lys Glu Glu Ile Leu Lys
            195                 200                 205

Lys Leu Lys Glu Leu Gln Glu Gly Pro Gly Pro Gly Gln Tyr Ile Lys
            210                 215                 220

Ala Asn Ser Lys Phe Ile Gly Ile Thr Glu Leu Gly Pro Gly Phe Asn
225                 230                 235                 240

Asn Phe Thr Val Ser Phe Trp Leu Arg Val Pro Lys Val Ser Ala Ser
            245                 250                 255

His Leu Glu Gly Arg Gly Asp
            260

<210> SEQ ID NO 66
<211> LENGTH: 193
<212> TYPE: PRT
<213> ORGANISM: Artificial
```

```
<220> FEATURE:
<223> OTHER INFORMATION: (RGD_p25)1x_PfTrx_HPV16_L2(20-38)3

<400> SEQUENCE: 66

Met Arg Gly Asp Gly Lys Leu Ile Pro Asn Ala Ser Leu Ile Glu Asn
1               5                   10                  15

Cys Thr Lys Ala Glu Leu Gly Pro Gly Pro Gly Met Ile Ile Glu Tyr
                20                  25                  30

Asp Gly Glu Ile Asp Phe Thr Lys Gly Arg Val Val Leu Trp Phe Ser
            35                  40                  45

Ile Pro Gly Cys Gly Pro Lys Thr Cys Lys Gln Ala Gly Thr Cys Pro
    50                  55                  60

Pro Asp Ile Ile Pro Lys Val Glu Gly Gly Pro Lys Thr Cys Lys
65                  70                  75                  80

Gln Ala Gly Thr Cys Pro Pro Asp Ile Ile Pro Lys Val Glu Gly Gly
                85                  90                  95

Gly Pro Lys Thr Cys Lys Gln Ala Gly Thr Cys Pro Pro Asp Ile Ile
            100                 105                 110

Pro Lys Val Glu Gly Gly Gly Pro Cys Arg Leu Val Glu Arg Phe Met
    115                 120                 125

Thr Glu Leu Ser Glu Tyr Phe Glu Asp Ile Gln Ile Val His Ile Asn
130                 135                 140

Ala Gly Lys Trp Lys Asn Ile Val Asp Lys Phe Asn Ile Leu Asn Val
145                 150                 155                 160

Pro Thr Leu Val Tyr Leu Lys Asp Gly Arg Glu Val Gly Arg Gln Asn
                165                 170                 175

Leu Ile Arg Ser Lys Glu Glu Ile Leu Lys Lys Leu Lys Glu Leu Gln
            180                 185                 190

Glu

<210> SEQ ID NO 67
<211> LENGTH: 218
<212> TYPE: PRT
<213> ORGANISM: Artificial
<220> FEATURE:
<223> OTHER INFORMATION: (RGD_p25)2x_PfTrx_HPV16_L2(20-38)3

<400> SEQUENCE: 67

Arg Gly Asp Gly Lys Leu Ile Pro Asn Ala Ser Leu Ile Glu Asn Cys
1               5                   10                  15

Thr Lys Ala Glu Leu Gly Pro Gly Pro Gly Met Ile Ile Glu Tyr Asp
                20                  25                  30

Gly Glu Ile Asp Phe Thr Lys Gly Arg Val Val Leu Trp Phe Ser Ile
            35                  40                  45

Pro Gly Cys Gly Pro Lys Thr Cys Lys Gln Ala Gly Thr Cys Pro Pro
    50                  55                  60

Asp Ile Ile Pro Lys Val Glu Gly Gly Pro Lys Thr Cys Lys Gln
65                  70                  75                  80

Ala Gly Thr Cys Pro Pro Asp Ile Ile Pro Lys Val Glu Gly Gly Gly
                85                  90                  95

Pro Lys Thr Cys Lys Gln Ala Gly Thr Cys Pro Pro Asp Ile Ile Pro
            100                 105                 110

Lys Val Glu Gly Gly Gly Pro Cys Arg Leu Val Glu Arg Phe Met Thr
    115                 120                 125

Glu Leu Ser Glu Tyr Phe Glu Asp Ile Gln Ile Val His Ile Asn Ala
130                 135                 140
```

Gly Lys Trp Lys Asn Ile Val Asp Lys Phe Asn Ile Leu Asn Val Pro
145                 150                 155                 160

Thr Leu Val Tyr Leu Lys Asp Gly Arg Glu Val Gly Arg Gln Asn Leu
            165                 170                 175

Ile Arg Ser Lys Glu Glu Ile Leu Lys Leu Lys Glu Leu Gln Glu
            180                 185                 190

Gly Pro Gly Pro Gly Lys Leu Ile Pro Asn Ala Ser Leu Ile Glu Asn
        195                 200                 205

Cys Thr Lys Ala Glu Leu Gly Arg Gly Asp
        210                 215

<210> SEQ ID NO 68
<211> LENGTH: 211
<212> TYPE: PRT
<213> ORGANISM: Artificial
<220> FEATURE:
<223> OTHER INFORMATION: (RGD_PADRE)2x_PfTrx_HPV51_L2(20-38)3

<400> SEQUENCE: 68

Met Arg Gly Asp Gly Ala Lys Phe Val Ala Ala Trp Thr Leu Lys Ala
1               5                   10                  15

Ala Ala Gly Pro Gly Pro Gly Met Ile Ile Glu Tyr Asp Gly Glu Ile
            20                  25                  30

Asp Phe Thr Lys Gly Arg Val Val Leu Trp Phe Ser Ile Pro Gly Cys
            35                  40                  45

Gly Pro Ser Thr Cys Lys Ala Ala Gly Thr Cys Pro Pro Asp Val Val
        50                  55                  60

Asn Lys Val Glu Gly Gly Pro Ser Thr Cys Lys Ala Ala Gly Thr
65                  70                  75                  80

Cys Pro Pro Asp Val Val Asn Lys Val Glu Gly Gly Pro Ser Thr
                85                  90                  95

Cys Lys Ala Ala Gly Thr Cys Pro Pro Asp Val Val Asn Lys Val Glu
            100                 105                 110

Gly Gly Gly Pro Cys Arg Leu Val Glu Arg Phe Met Thr Glu Leu Ser
        115                 120                 125

Glu Tyr Phe Glu Asp Ile Gln Ile Val His Ile Asn Ala Gly Lys Trp
    130                 135                 140

Lys Asn Ile Val Asp Lys Phe Asn Ile Leu Asn Val Pro Thr Leu Val
145                 150                 155                 160

Tyr Leu Lys Asp Gly Arg Glu Val Gly Arg Gln Asn Leu Ile Arg Ser
            165                 170                 175

Lys Glu Glu Ile Leu Lys Leu Lys Glu Leu Gln Glu Gly Pro Gly
            180                 185                 190

Pro Gly Ala Lys Phe Val Ala Ala Trp Thr Leu Lys Ala Ala Ala Gly
        195                 200                 205

Arg Gly Asp
    210

<210> SEQ ID NO 69
<211> LENGTH: 211
<212> TYPE: PRT
<213> ORGANISM: Artificial
<220> FEATURE:
<223> OTHER INFORMATION: (RGD_PADRE)2x_PfTrx_HPV31_L2(20-38)3

<400> SEQUENCE: 69

Met Arg Gly Asp Gly Ala Lys Phe Val Ala Ala Trp Thr Leu Lys Ala

```
            1               5                  10                 15
Ala Ala Gly Pro Gly Pro Gly Met Ile Ile Glu Tyr Asp Gly Glu Ile
                    20                  25                 30

Asp Phe Thr Lys Gly Arg Val Val Leu Trp Phe Ser Ile Pro Gly Cys
                35                  40                 45

Gly Pro Gln Thr Cys Lys Ala Ala Gly Thr Cys Pro Ser Asp Val Ile
            50                  55                 60

Pro Lys Ile Glu His Gly Gly Pro Gln Thr Cys Lys Ala Ala Gly Thr
65                  70                  75                 80

Cys Pro Ser Asp Val Ile Pro Lys Ile Glu His Gly Gly Pro Gln Thr
                    85                  90                 95

Cys Lys Ala Ala Gly Thr Cys Pro Ser Asp Val Ile Pro Lys Ile Glu
                100                 105                110

His Gly Gly Pro Cys Arg Leu Val Glu Arg Phe Met Thr Glu Leu Ser
            115                 120                125

Glu Tyr Phe Glu Asp Ile Gln Ile Val His Ile Asn Ala Gly Lys Trp
        130                 135                 140

Lys Asn Ile Val Asp Lys Phe Asn Ile Leu Asn Val Pro Thr Leu Val
145                 150                 155                160

Tyr Leu Lys Asp Gly Arg Glu Val Gly Arg Gln Asn Leu Ile Arg Ser
                165                 170                175

Lys Glu Glu Ile Leu Lys Leu Lys Glu Leu Gln Glu Gly Pro Gly
            180                 185                 190

Pro Gly Ala Lys Phe Val Ala Ala Trp Thr Leu Lys Ala Ala Ala Gly
            195                 200                 205

Arg Gly Asp
        210

<210> SEQ ID NO 70
<211> LENGTH: 175
<212> TYPE: PRT
<213> ORGANISM: Artificial
<220> FEATURE:
<223> OTHER INFORMATION: EcTrx HPV16 L2(20-38)3

<400> SEQUENCE: 70

Met Gly Asp Lys Ile Ile His Leu Thr Asp Asp Ser Phe Asp Thr Asp
1               5                  10                 15

Val Leu Lys Ala Asp Gly Ala Ile Leu Val Asp Phe Trp Ala Glu Trp
                20                  25                 30

Cys Gly Pro Lys Thr Cys Lys Gln Ala Gly Thr Cys Pro Pro Asp Ile
                35                  40                 45

Ile Pro Lys Val Glu Gly Gly Pro Lys Thr Cys Lys Gln Ala Gly
            50                  55                 60

Thr Cys Pro Pro Asp Ile Ile Pro Lys Val Glu Gly Gly Pro Lys
65                  70                  75                 80

Thr Cys Lys Gln Ala Gly Thr Cys Pro Pro Asp Ile Ile Pro Lys Val
                    85                  90                 95

Glu Gly Gly Gly Pro Cys Lys Met Ile Ala Pro Ile Leu Asp Glu Ile
                100                 105                110

Ala Asp Glu Tyr Gln Gly Lys Leu Thr Val Ala Lys Leu Asn Ile Asp
            115                 120                 125

Gln Asn Pro Gly Thr Ala Pro Lys Tyr Gly Ile Arg Gly Ile Pro Thr
        130                 135                 140

Leu Leu Leu Phe Lys Asn Gly Glu Val Ala Ala Thr Lys Val Gly Ala
```

-continued

```
            145                 150                 155                 160
Leu Ser Lys Gly Gln Leu Lys Glu Phe Leu Asp Ala Asn Leu Ala
                165                 170                 175

<210> SEQ ID NO 71
<211> LENGTH: 189
<212> TYPE: PRT
<213> ORGANISM: Artificial
<220> FEATURE:
<223> OTHER INFORMATION: PADRE1x PfTrx HPV16 L2(20-38)3

<400> SEQUENCE: 71

Met Arg Gly Asp Gly Ala Lys Phe Val Ala Ala Trp Thr Leu Lys Ala
1               5                   10                  15

Ala Ala Gly Pro Gly Pro Gly Met Ile Ile Glu Tyr Asp Gly Glu Ile
                20                  25                  30

Asp Phe Thr Lys Gly Arg Val Val Leu Trp Phe Ser Ile Pro Gly Cys
            35                  40                  45

Gly Pro Lys Thr Cys Lys Gln Ala Gly Thr Cys Pro Pro Asp Ile Ile
50                  55                  60

Pro Lys Val Glu Gly Gly Gly Pro Lys Thr Cys Lys Gln Ala Gly Thr
65                  70                  75                  80

Cys Pro Pro Asp Ile Ile Pro Lys Val Glu Gly Gly Gly Pro Lys Thr
                85                  90                  95

Cys Lys Gln Ala Gly Thr Cys Pro Pro Asp Ile Ile Pro Lys Val Glu
            100                 105                 110

Gly Gly Gly Pro Cys Arg Leu Val Glu Arg Phe Met Thr Glu Leu Ser
        115                 120                 125

Glu Tyr Phe Glu Asp Ile Gln Ile Val His Ile Asn Ala Gly Lys Trp
130                 135                 140

Lys Asn Ile Val Asp Lys Phe Asn Ile Leu Asn Val Pro Thr Leu Val
145                 150                 155                 160

Tyr Leu Lys Asp Gly Arg Glu Val Gly Arg Gln Asn Leu Ile Arg Ser
                165                 170                 175

Lys Glu Glu Ile Leu Lys Lys Leu Lys Glu Leu Gln Glu
            180                 185

<210> SEQ ID NO 72
<211> LENGTH: 211
<212> TYPE: PRT
<213> ORGANISM: Artificial
<220> FEATURE:
<223> OTHER INFORMATION: PADRE2x PfTrx HPV16 L2(20-38)3

<400> SEQUENCE: 72

Met Arg Gly Asp Gly Ala Lys Phe Val Ala Ala Trp Thr Leu Lys Ala
1               5                   10                  15

Ala Ala Gly Pro Gly Pro Gly Met Ile Ile Glu Tyr Asp Gly Glu Ile
                20                  25                  30

Asp Phe Thr Lys Gly Arg Val Val Leu Trp Phe Ser Ile Pro Gly Cys
            35                  40                  45

Gly Pro Lys Thr Cys Lys Gln Ala Gly Thr Cys Pro Pro Asp Ile Ile
50                  55                  60

Pro Lys Val Glu Gly Gly Gly Pro Lys Thr Cys Lys Gln Ala Gly Thr
65                  70                  75                  80

Cys Pro Pro Asp Ile Ile Pro Lys Val Glu Gly Gly Gly Pro Lys Thr
                85                  90                  95
```

-continued

```
Cys Lys Gln Ala Gly Thr Cys Pro Pro Asp Ile Ile Pro Lys Val Glu
                100                 105                 110
Gly Gly Gly Pro Cys Arg Leu Val Glu Arg Phe Met Thr Glu Leu Ser
            115                 120                 125
Glu Tyr Phe Glu Asp Ile Gln Ile Val His Ile Asn Ala Gly Lys Trp
        130                 135                 140
Lys Asn Ile Val Asp Lys Phe Asn Ile Leu Asn Val Pro Thr Leu Val
145                 150                 155                 160
Tyr Leu Lys Asp Gly Arg Glu Val Gly Arg Gln Asn Leu Ile Arg Ser
                165                 170                 175
Lys Glu Glu Ile Leu Lys Lys Leu Lys Glu Leu Gln Glu Gly Pro Gly
            180                 185                 190
Pro Gly Ala Lys Phe Val Ala Ala Trp Thr Leu Lys Ala Ala Ala Gly
        195                 200                 205
Arg Gly Asp
    210
```

<210> SEQ ID NO 73
<211> LENGTH: 215
<212> TYPE: PRT
<213> ORGANISM: Artificial
<220> FEATURE:
<223> OTHER INFORMATION: p2p301x PfTrx HPV16 L2(20-38)3

<400> SEQUENCE: 73

```
Met Arg Gly Asp Gly Gln Tyr Ile Lys Ala Asn Ser Lys Phe Ile Gly
1               5                   10                  15
Ile Thr Glu Leu Gly Pro Gly Phe Asn Asn Phe Thr Val Ser Phe Trp
            20                  25                  30
Leu Arg Val Pro Lys Val Ser Ala Ser His Leu Glu Gly Pro Gly Pro
        35                  40                  45
Gly Met Ile Ile Glu Tyr Asp Gly Glu Ile Asp Phe Thr Lys Gly Arg
    50                  55                  60
Val Val Leu Trp Phe Ser Ile Pro Gly Cys Gly Pro Lys Thr Cys Lys
65                  70                  75                  80
Gln Ala Gly Thr Cys Pro Pro Asp Ile Ile Pro Lys Val Glu Gly Gly
                85                  90                  95
Gly Pro Lys Thr Cys Lys Gln Ala Gly Thr Cys Pro Pro Asp Ile Ile
            100                 105                 110
Pro Lys Val Glu Gly Gly Gly Pro Lys Thr Cys Lys Gln Ala Gly Thr
        115                 120                 125
Cys Pro Pro Asp Ile Ile Pro Lys Val Glu Gly Gly Pro Cys Arg
    130                 135                 140
Leu Val Glu Arg Phe Met Thr Glu Leu Ser Glu Tyr Phe Glu Asp Ile
145                 150                 155                 160
Gln Ile Val His Ile Asn Ala Gly Lys Trp Lys Asn Ile Val Asp Lys
                165                 170                 175
Phe Asn Ile Leu Asn Val Pro Thr Leu Val Tyr Leu Lys Asp Gly Arg
            180                 185                 190
Glu Val Gly Arg Gln Asn Leu Ile Arg Ser Lys Glu Glu Ile Leu Lys
        195                 200                 205
Lys Leu Lys Glu Leu Gln Glu
    210                 215
```

<210> SEQ ID NO 74
<211> LENGTH: 263

<212> TYPE: PRT
<213> ORGANISM: Artificial
<220> FEATURE:
<223> OTHER INFORMATION: p2p302x PfTrx HPV16 L2(20-38)3

<400> SEQUENCE: 74

Met Arg Gly Asp Gly Gln Tyr Ile Lys Ala Asn Ser Lys Phe Ile Gly
1               5                   10                  15

Ile Thr Glu Leu Gly Pro Gly Phe Asn Asn Phe Thr Val Ser Phe Trp
            20                  25                  30

Leu Arg Val Pro Lys Val Ser Ala Ser His Leu Glu Gly Pro Gly Pro
        35                  40                  45

Gly Met Ile Ile Glu Tyr Asp Gly Glu Ile Asp Phe Thr Lys Gly Arg
    50                  55                  60

Val Val Leu Trp Phe Ser Ile Pro Gly Cys Gly Pro Lys Thr Cys Lys
65                  70                  75                  80

Gln Ala Gly Thr Cys Pro Pro Asp Ile Ile Pro Lys Val Glu Gly Gly
                85                  90                  95

Gly Pro Lys Thr Cys Lys Gln Ala Gly Thr Cys Pro Pro Asp Ile Ile
            100                 105                 110

Pro Lys Val Glu Gly Gly Gly Pro Lys Thr Cys Lys Gln Ala Gly Thr
        115                 120                 125

Cys Pro Pro Asp Ile Ile Pro Lys Val Glu Gly Gly Gly Pro Cys Arg
    130                 135                 140

Leu Val Glu Arg Phe Met Thr Glu Leu Ser Glu Tyr Phe Glu Asp Ile
145                 150                 155                 160

Gln Ile Val His Ile Asn Ala Gly Lys Trp Lys Asn Ile Val Asp Lys
                165                 170                 175

Phe Asn Ile Leu Asn Val Pro Thr Leu Val Tyr Leu Lys Asp Gly Arg
            180                 185                 190

Glu Val Gly Arg Gln Asn Leu Ile Arg Ser Lys Glu Glu Ile Leu Lys
        195                 200                 205

Lys Leu Lys Glu Leu Gln Glu Gly Pro Gly Pro Gly Gln Tyr Ile Lys
    210                 215                 220

Ala Asn Ser Lys Phe Ile Gly Ile Thr Glu Leu Gly Pro Gly Phe Asn
225                 230                 235                 240

Asn Phe Thr Val Ser Phe Trp Leu Arg Val Pro Lys Val Ser Ala Ser
                245                 250                 255

His Leu Glu Gly Arg Gly Asp
                260

<210> SEQ ID NO 75
<211> LENGTH: 193
<212> TYPE: PRT
<213> ORGANISM: Artificial
<220> FEATURE:
<223> OTHER INFORMATION: p251x PfTrx HPV16 L2(20-38)3

<400> SEQUENCE: 75

Met Arg Gly Asp Gly Lys Leu Ile Pro Asn Ala Ser Leu Ile Glu Asn
1               5                   10                  15

Cys Thr Lys Ala Glu Leu Gly Pro Gly Pro Met Ile Ile Glu Tyr
            20                  25                  30

Asp Gly Glu Ile Asp Phe Thr Lys Gly Arg Val Val Leu Trp Phe Ser
        35                  40                  45

Ile Pro Gly Cys Gly Pro Lys Thr Cys Lys Gln Ala Gly Thr Cys Pro
    50                  55                  60

```
Pro Asp Ile Ile Pro Lys Val Glu Gly Gly Pro Lys Thr Cys Lys
 65                  70                  75                  80

Gln Ala Gly Thr Cys Pro Pro Asp Ile Ile Pro Lys Val Glu Gly Gly
                 85                  90                  95

Gly Pro Lys Thr Cys Lys Gln Ala Gly Thr Cys Pro Asp Ile Ile
            100                 105                 110

Pro Lys Val Glu Gly Gly Gly Pro Cys Arg Leu Val Glu Arg Phe Met
            115                 120                 125

Thr Glu Leu Ser Glu Tyr Phe Glu Asp Ile Gln Ile Val His Ile Asn
            130                 135                 140

Ala Gly Lys Trp Lys Asn Ile Val Asp Lys Phe Asn Ile Leu Asn Val
145                 150                 155                 160

Pro Thr Leu Val Tyr Leu Lys Asp Gly Arg Glu Val Gly Arg Gln Asn
                165                 170                 175

Leu Ile Arg Ser Lys Glu Glu Ile Leu Lys Lys Leu Lys Glu Leu Gln
            180                 185                 190

Glu

<210> SEQ ID NO 76
<211> LENGTH: 219
<212> TYPE: PRT
<213> ORGANISM: Artificial
<220> FEATURE:
<223> OTHER INFORMATION: p252x PfTrx HPV16 L2(20-38)3

<400> SEQUENCE: 76

Met Arg Gly Asp Gly Lys Leu Ile Pro Asn Ala Ser Leu Ile Glu Asn
 1                5                  10                  15

Cys Thr Lys Ala Glu Leu Gly Pro Gly Pro Gly Met Ile Ile Glu Tyr
                 20                  25                  30

Asp Gly Glu Ile Asp Phe Thr Lys Gly Arg Val Val Leu Trp Phe Ser
             35                  40                  45

Ile Pro Gly Cys Gly Pro Lys Thr Cys Lys Gln Ala Gly Thr Cys Pro
 50                  55                  60

Pro Asp Ile Ile Pro Lys Val Glu Gly Gly Pro Lys Thr Cys Lys
 65                  70                  75                  80

Gln Ala Gly Thr Cys Pro Pro Asp Ile Ile Pro Lys Val Glu Gly Gly
                 85                  90                  95

Gly Pro Lys Thr Cys Lys Gln Ala Gly Thr Cys Pro Asp Ile Ile
            100                 105                 110

Pro Lys Val Glu Gly Gly Gly Pro Cys Arg Leu Val Glu Arg Phe Met
            115                 120                 125

Thr Glu Leu Ser Glu Tyr Phe Glu Asp Ile Gln Ile Val His Ile Asn
            130                 135                 140

Ala Gly Lys Trp Lys Asn Ile Val Asp Lys Phe Asn Ile Leu Asn Val
145                 150                 155                 160

Pro Thr Leu Val Tyr Leu Lys Asp Gly Arg Glu Val Gly Arg Gln Asn
                165                 170                 175

Leu Ile Arg Ser Lys Glu Glu Ile Leu Lys Lys Leu Lys Glu Leu Gln
            180                 185                 190

Glu Gly Pro Gly Pro Gly Lys Leu Ile Pro Asn Ala Ser Leu Ile Glu
            195                 200                 205

Asn Cys Thr Lys Ala Glu Leu Gly Arg Gly Asp
    210                 215
```

```
<210> SEQ ID NO 77
<211> LENGTH: 211
<212> TYPE: PRT
<213> ORGANISM: Artificial
<220> FEATURE:
<223> OTHER INFORMATION: PADRE2x PfTrx HPV31 L2(20-38)3

<400> SEQUENCE: 77

Met Arg Gly Asp Gly Ala Lys Phe Val Ala Ala Trp Thr Leu Lys Ala
1               5                   10                  15

Ala Ala Gly Pro Gly Pro Gly Met Ile Ile Glu Tyr Asp Gly Glu Ile
                20                  25                  30

Asp Phe Thr Lys Gly Arg Val Val Leu Trp Phe Ser Ile Pro Gly Cys
            35                  40                  45

Gly Pro Gln Thr Cys Lys Ala Ala Gly Thr Cys Pro Ser Asp Val Ile
    50                  55                  60

Pro Lys Ile Glu His Gly Gly Pro Gln Thr Cys Lys Ala Ala Gly Thr
65                  70                  75                  80

Cys Pro Ser Asp Val Ile Pro Lys Ile Glu His Gly Gly Pro Gln Thr
                85                  90                  95

Cys Lys Ala Ala Gly Thr Cys Pro Ser Asp Val Ile Pro Lys Ile Glu
                100                 105                 110

His Gly Gly Pro Cys Arg Leu Val Glu Arg Phe Met Thr Glu Leu Ser
            115                 120                 125

Glu Tyr Phe Glu Asp Ile Gln Ile Val His Ile Asn Ala Gly Lys Trp
    130                 135                 140

Lys Asn Ile Val Asp Lys Phe Asn Ile Leu Asn Val Pro Thr Leu Val
145                 150                 155                 160

Tyr Leu Lys Asp Gly Arg Glu Val Gly Arg Gln Asn Leu Ile Arg Ser
                165                 170                 175

Lys Glu Glu Ile Leu Lys Lys Leu Lys Glu Leu Gln Glu Gly Pro Gly
                180                 185                 190

Pro Gly Ala Lys Phe Val Ala Ala Trp Thr Leu Lys Ala Ala Ala Gly
            195                 200                 205

Arg Gly Asp
    210

<210> SEQ ID NO 78
<211> LENGTH: 211
<212> TYPE: PRT
<213> ORGANISM: Artificial
<220> FEATURE:
<223> OTHER INFORMATION: PADRE2x PfTrx HPV51 L2(20-38)3

<400> SEQUENCE: 78

Met Arg Gly Asp Gly Ala Lys Phe Val Ala Ala Trp Thr Leu Lys Ala
1               5                   10                  15

Ala Ala Gly Pro Gly Pro Gly Met Ile Ile Glu Tyr Asp Gly Glu Ile
                20                  25                  30

Asp Phe Thr Lys Gly Arg Val Val Leu Trp Phe Ser Ile Pro Gly Cys
            35                  40                  45

Gly Pro Ser Thr Cys Lys Ala Ala Gly Thr Cys Pro Pro Asp Val Val
    50                  55                  60

Asn Lys Val Glu Gly Gly Gly Pro Ser Thr Cys Lys Ala Ala Gly Thr
65                  70                  75                  80

Cys Pro Pro Asp Val Val Asn Lys Val Glu Gly Gly Gly Pro Ser Thr
                85                  90                  95
```

```
Cys Lys Ala Ala Gly Thr Cys Pro Pro Asp Val Val Asn Lys Val Glu
                100                 105                 110

Gly Gly Gly Pro Cys Arg Leu Val Glu Arg Phe Met Thr Glu Leu Ser
            115                 120                 125

Glu Tyr Phe Glu Asp Ile Gln Ile Val His Ile Asn Ala Gly Lys Trp
    130                 135                 140

Lys Asn Ile Val Asp Lys Phe Asn Ile Leu Asn Val Pro Thr Leu Val
145                 150                 155                 160

Tyr Leu Lys Asp Gly Arg Glu Val Gly Arg Gln Asn Leu Ile Arg Ser
                165                 170                 175

Lys Glu Glu Ile Leu Lys Lys Leu Lys Glu Leu Gln Glu Gly Pro Gly
            180                 185                 190

Pro Gly Ala Lys Phe Val Ala Ala Trp Thr Leu Lys Ala Ala Ala Gly
        195                 200                 205

Arg Gly Asp
    210

<210> SEQ ID NO 79
<211> LENGTH: 223
<212> TYPE: PRT
<213> ORGANISM: Artificial
<220> FEATURE:
<223> OTHER INFORMATION: PfTrx HPV16 L2(20-38)3-IMX313T

<400> SEQUENCE: 79

Met Ile Ile Glu Tyr Asp Gly Glu Ile Asp Phe Thr Lys Gly Arg Val
1               5                   10                  15

Val Leu Trp Phe Ser Ile Pro Gly Cys Gly Pro Lys Thr Cys Lys Gln
            20                  25                  30

Ala Gly Thr Cys Pro Pro Asp Ile Ile Pro Lys Val Glu Gly Gly Gly
        35                  40                  45

Pro Lys Thr Cys Lys Gln Ala Gly Thr Cys Pro Pro Asp Ile Ile Pro
    50                  55                  60

Lys Val Glu Gly Gly Gly Pro Lys Thr Cys Lys Gln Ala Gly Thr Cys
65                  70                  75                  80

Pro Pro Asp Ile Ile Pro Lys Val Glu Gly Gly Pro Cys Arg Leu
                85                  90                  95

Val Glu Arg Phe Met Thr Glu Leu Ser Glu Tyr Phe Glu Asp Ile Gln
            100                 105                 110

Ile Val His Ile Asn Ala Gly Lys Trp Lys Asn Ile Val Asp Lys Phe
        115                 120                 125

Asn Ile Leu Asn Val Pro Thr Leu Val Tyr Leu Lys Asp Gly Arg Glu
    130                 135                 140

Val Gly Arg Gln Asn Leu Ile Arg Ser Lys Glu Ile Leu Lys Lys
145                 150                 155                 160

Leu Lys Glu Leu Gln Glu Gly Ser Lys Lys Gln Gly Asp Ala Asp Val
                165                 170                 175

Cys Gly Glu Val Ala Tyr Ile Gln Ser Val Val Ser Asp Cys His Val
            180                 185                 190

Pro Thr Ala Glu Leu Arg Thr Leu Leu Glu Ile Arg Lys Leu Phe Leu
        195                 200                 205

Glu Ile Gln Lys Leu Lys Val Glu Gly Arg Arg Arg Arg Ser
    210                 215                 220

<210> SEQ ID NO 80
```

<211> LENGTH: 179
<212> TYPE: PRT
<213> ORGANISM: Artificial
<220> FEATURE:
<223> OTHER INFORMATION: PfTrx HPV16 L2(20-38)1-IMX313T

<400> SEQUENCE: 80

Met Ile Ile Glu Tyr Asp Gly Glu Ile Asp Phe Thr Lys Gly Arg Val
1               5                   10                  15

Val Leu Trp Phe Ser Ile Pro Gly Cys Gly Pro Lys Thr Cys Lys Gln
            20                  25                  30

Ala Gly Thr Cys Pro Pro Asp Ile Ile Pro Lys Val Glu Gly Gly Gly
        35                  40                  45

Pro Cys Arg Leu Val Glu Arg Phe Met Thr Glu Leu Ser Glu Tyr Phe
    50                  55                  60

Glu Asp Ile Gln Ile Val His Ile Asn Ala Gly Lys Trp Lys Asn Ile
65                  70                  75                  80

Val Asp Lys Phe Asn Ile Leu Asn Val Pro Thr Leu Val Tyr Leu Lys
                85                  90                  95

Asp Gly Arg Glu Val Gly Arg Gln Asn Leu Ile Arg Ser Lys Glu Glu
            100                 105                 110

Ile Leu Lys Lys Leu Lys Glu Leu Gln Glu Gly Ser Lys Lys Gln Gly
        115                 120                 125

Asp Ala Asp Val Cys Gly Glu Val Ala Tyr Ile Gln Ser Val Val Ser
    130                 135                 140

Asp Cys His Val Pro Thr Ala Glu Leu Arg Thr Leu Leu Glu Ile Arg
145                 150                 155                 160

Lys Leu Phe Leu Glu Ile Gln Lys Leu Lys Val Glu Gly Arg Arg Arg
                165                 170                 175

Arg Arg Ser

<210> SEQ ID NO 81
<211> LENGTH: 127
<212> TYPE: PRT
<213> ORGANISM: Artificial
<220> FEATURE:
<223> OTHER INFORMATION: HPV16 L2(20-38)3-IMX313T

<400> SEQUENCE: 81

Met Gly Gly Pro Lys Thr Cys Lys Gln Ala Gly Thr Cys Pro Pro Asp
1               5                   10                  15

Ile Ile Pro Lys Val Glu Gly Gly Gly Pro Lys Thr Cys Lys Gln Ala
            20                  25                  30

Gly Thr Cys Pro Pro Asp Ile Ile Pro Lys Val Glu Gly Gly Gly Pro
        35                  40                  45

Lys Thr Cys Lys Gln Ala Gly Thr Cys Pro Pro Asp Ile Ile Pro Lys
    50                  55                  60

Val Glu Gly Gly Gly Pro Gly Ser Lys Lys Gln Gly Asp Ala Asp Val
65                  70                  75                  80

Cys Gly Glu Val Ala Tyr Ile Gln Ser Val Val Ser Asp Cys His Val
                85                  90                  95

Pro Thr Ala Glu Leu Arg Thr Leu Leu Glu Ile Arg Lys Leu Phe Leu
            100                 105                 110

Glu Ile Gln Lys Leu Lys Val Glu Gly Arg Arg Arg Arg Arg Ser
        115                 120                 125

<210> SEQ ID NO 82

<211> LENGTH: 5196
<212> TYPE: DNA
<213> ORGANISM: Artificial
<220> FEATURE:
<223> OTHER INFORMATION: expression vector for TfTrx8mer-IMX3T3

<400> SEQUENCE: 82

| | |
|---|---:|
| cgctgttttg gcggatgaga gaagattttc agcctgatac agattaaatc agaacgcaga | 60 |
| agcggtctga taaaacagaa tttgcctggc ggcagtagcg cggtggtccc acctgacccc | 120 |
| atgccgaact cagaagtgaa acgccgtagc gccgatggta gtgtggggtc tccccatgcg | 180 |
| agagtaggga actgccaggc atcaaataaa acgaaaggct cagtcgaaag actgggcctt | 240 |
| tcgttttatc tgttgtttgt cggtgaacgc tctcctgagt aggacaaatc cgccgggagc | 300 |
| ggatttgaac gttgcgaagc aacggcccgg agggtggcgg gcaggacgcc cgccataaac | 360 |
| tgccaggcat caaattaagc agaaggccat cctgacggat ggccttttg cgtttctaca | 420 |
| aactcttact agttacgtag atcgtaatct aactgtcaga ccaagtttac tcatatatac | 480 |
| tttagattga tttaaaactt cattttaat ttaaaaggat ctaggtgaag atcctttttg | 540 |
| ataatctcat gaccaaacga tcgccttaac gtgagttttc gttccactga gcgtcagacc | 600 |
| ccttaataag atgatcttct tgagatcgtt ttggtctgcg cgtaatctct gctctgaaa | 660 |
| acgaaaaaac cgccttgcag gcggttttt cgaaggttct ctgagctacc aactctttga | 720 |
| accgaggtaa ctggcttgga ggagcgcagt caccaaaact tgtcctttca gtttagcctt | 780 |
| aaccggcgca tgacttcaag actaactcct ctaaatcaat taccagtggc tgctgccagt | 840 |
| ggtgcttttg catgtctttc cgggttggac tcaagacgat agttaccgga taaggcgcag | 900 |
| cggtcggact gaacgggggg ttcgtgcata cagtccagct tggagcgaac tgcctacccg | 960 |
| gaactgagtg tcaggcgtgg aatgagacaa acgcggccat aacagcggaa tgacaccggt | 1020 |
| aaaccgaaag gcaggaacag gagagcgcac gagggagccg ccaggggaa acgcctggta | 1080 |
| tctttatagt cctgtcgggt ttcgccacca ctgatttgag cgtcagattt cgtgatgctt | 1140 |
| gtcaggggg cggagcctat ggaaaaacgg ctttgccgcg gccctctcac ttccctgtta | 1200 |
| agtatcttcc tggcatcttc caggaaatct ccgccccgtt cgtaagccat ttccgctcgc | 1260 |
| cgcagtcgaa cgaccgagcg tagcgagtca gtgagcgagg aagcggaata tatcctgtat | 1320 |
| cacatattct gctgacgcac cggtgcagcc ttttttctcc tgccacatga agcacttcac | 1380 |
| tgacaccctc atcagtgcca acatagtaag ccagtataca ctccgctagc gctgaggtct | 1440 |
| gcctcgtgaa gaaggtgttg ctgactcata ccaggcctga atcgccccgg catcatccag | 1500 |
| ccagaaagtg agggagccac ggttgatgag agctttgttg taggtggacc agttggtgat | 1560 |
| tttgaacttt tgctttgcca cggaacggtc tgcgttgtcg ggaagatgcc ggcgccatag | 1620 |
| tggcgcgtga tctgatcctt caactcagca aaagttcgat ttattcaaca aagccacgtt | 1680 |
| gtgtctcaaa atctctgatg ttacattgca caagataaaa atatatcatc atgaacaata | 1740 |
| aaactgtctg cttacataaa cagtaataca agggtgtta tgagccatat tcaacgggaa | 1800 |
| acgtcttgca gcaggccgcg attaaattcc aacatggatg ctgatttata tgggtataaa | 1860 |
| tgggctcgcg ataatgtcgg gcaatcaggt gcgacaatct atcgattgta tgggaagccc | 1920 |
| gatgcgccag agttgtttct gaaacatggc aaaggtagcg ttgccaatga tgttacagat | 1980 |
| gagatggtca gactaaactg gctgacggaa tttatgcctc ttccgaccat caagcatttt | 2040 |
| atccgtactc ctgatgatgc atggttactc accactgcga tccagggaa acagcattc | 2100 |
| caggtattag aagaatatcc ggattcaggt gaaaatattg ttgatgcgct ggcagtgttc | 2160 |

```
ctgcgccggt tgcattcgat tcctgtttgt aattgtcctt ttaactctga tcgcgtattt      2220
cgtctcgctc aggcgcaatc acgaatgaat aacggtttgg ttgatgcgag tgattttgat      2280
gacgagcgta atggctggcc tgttgaacaa gtctggaaag aaatgcataa acttttgcca      2340
ttctcaccgg attcagtcgt cactcatggt gatttctcac ttgataacct tattttgac      2400 gaggggaaat taataggttg tattgatgtt ggacgagtcg gaatcgcaga ccgataccag      2460
gatcttgcca tcctatggaa ctgcctcggt gagttttctc cttcattaca gaaacggctt      2520
tttcaaaaat atggtattga taatcctgat atgaataaat tgcagtttca tttgatgctc      2580
gatgagtttt tctaatcaga attggttaat tggttgtaac actggcagag cattacgctg      2640
acttgacggg acggccatag tggcctttgt tgaataaata aagcctgggg tgcctaatga      2700
gtgagctaac tcacattaat tgcgttgcgc tcactgcccg ctttccagtc gggaaacctg      2760
tcgtgccagc tgcattaatg aatcggccaa cgcgcgggga gaggcggttt gcgtattggg      2820
cgccagggtg ttttctttt tcaccagtga cgggcaac agctgattgc ccttcaccgc         2880
ctggccctga gagagttgca gcaagcggtc cacgctggtt tgccccagca ggcgaaaatc      2940
ctgtttgatg gtggttaacg gcgggatata acatgagctg tcttcggtat cgtcgtatcc      3000
cactaccgag atatccgcac caacgcgcag cccggactcg gtaatggcgc gcattgcgcc      3060
cagcgccatc tgatcgttgg caaccagcat cgcagtggga acgatgccct cattcagcat      3120
ttgcatggtt tgttgaaaac cggacatggc actccagtcg ccttcccgtt ccgctatcgg      3180
ctgaatttga ttgcgagtga gatatttatg ccagccagcc agacgcagac gcgccgagac      3240
agaacttaat gggcccgcta acagcgcgat ttgctggtga cccaatgcga ccagatgctc      3300
cacgcccagt cgcgtaccgt cttcatggga gaaataata ctgttgatgg gtgtctggtc       3360
agagacatca agaaataacg ccggaacatt agtgcaggca gcttccacag caatggcatc      3420
ctggtcatcc agcggatagt taatgatcag cccactgacg cgttgcgcga agagattgtg      3480
caccgccgct ttacaggctt cgacgccgct tcgttctacc atcgacacca ccacgctggc      3540
acccagttga tcggcgcgag atttaatcgc cgcgacaatt tgcgacgcg cgtgcagggc       3600 cagactggag gtggcaacgc caatcagcaa cgactgtttg cccgccagtt gttgtgccac      3660
gcggttggga atgtaattca gctccgccat cgccgcttcc actttttccc gcgttttcgc      3720
agaaacgtgg ctggcctggt tcaccacgcg ggaaacggtc tgataagaga caccggcata      3780
ctctgcgaca tcgtataacg ttactggttt cacattcacc accctgaatt gactctcttc      3840
cgggcgctat catgccatac cgcgaaaggt tttgcgccat tcgatggtgt caacgtaaat      3900
gcatgccgct tcgccttccg gccaccagaa tagcctgcga ttcaacccct tcttcgatct      3960
gttttgctac ccgttgtagc ggaattcggt acctgtacaa gggcctcgtg atacgcctcg      4020
agatttttat aggttaatgt catgataata atggtttctt agacgtctgc gccgacatca      4080
taacggttct ggcaaatatt ctgaaatgag ctgttgacaa ttaatcatcg gctcgtataa      4140
tgtgtggaat tgtgagcgga taacaatttc acacaggaga tatcatatga ttattgagta      4200
cgatggcgag attgacttta ccaagggccg tgtggtgctg tggtttagca ttccgggttg      4260
cggtccgaag acctgcaaac aggcgggtac ctgcccgccg acatcattc cgaaagtgga       4320 aggtggcggt ccgaagacct gcaaacaaag cggtacctgc ccgccggatg ttgttccgaa      4380
agtggagggc ggtggcccgc aaacctgcaa ggcggcgggt acctgcccga gcgacgttat      4440
cccgaagatt gaacatggtg gcccgcagac ctgcaaggcg accggcacct gcccgccgga      4500
```

```
cgtgatcccg aaggttgagg gtggcggtcc gcgtacctgc aaagcggcgg gcacctgccc    4560
gccggatgtg attccgaagg ttgaaggcgg tggccctcag acttgcaaac tgactggcac    4620
ttgcccgccg gacgttattc cgaaggttga gcatggtggc ccgagcacct gcaaagctgc    4680
tggaacttgc ccgccggatg tggttaacaa ggttgaaggt ggcggtccga aaacctgcaa    4740
gcaagcgggc acctgcccga gcgatgtgat taacaaagtt gaaggcggtg gcccgtgccg    4800
tctggttgag cgtttcatga ccgagctgag cgaatacttt gaggacatcc aaattgtgca    4860
catcaacgcg ggcaagtgga aaaacatcgt tgacaagttc aacattctga acgtgccgac    4920
cctggtttat ctgaaagatg gtcgtgaggt gggtcgtcag aacctgatcc gtagcaaaga    4980
ggagattctg aagaaactga aagaactgca ggaaggtagc aagaagcaag gcgacgcgga    5040
tgtgtgcggt gaagttgcgt acatccaaag cgtggttagc gattgccacg ttccgaccgc    5100
ggaactgcgt accctgctgg agattcgtaa gctgttcctg gaaatccaaa aactgaaggt    5160
tgaaggtcgt cgtcgtcgtc gtagctaata aggatc                              5196
```

L2 PEPTIDE IMMUNOGENICITY

CROSS-REFERENCE TO RELATED APPLICATIONS

The present application is a U.S. national stage patent application of, and claims the priority benefit of International Patent Application Serial No. PCT/EP2017/063833, filed Jun. 7, 2017, and also claims the priority benefit of European Patent Application Serial No. 16173313.4 filed Jun. 7, 2016, the text and drawings of which are hereby incorporated by reference in their entireties.

The present invention relates to an immunogenic polypeptide comprising a multitude of human papillomavirus (HPV) L2 N-terminal peptides corresponding to amino acids 20 to 50 of the L2 polypeptide of HPV16, wherein said HPV L2 N-terminal peptides are L2 N-terminal peptides from at least two different HPV genotypes. The present invention also relates to said immunogenic polypeptide for use in medicine and for use in vaccination against HPV infection. Moreover, the present invention relates to a polynucleotide encoding the immunogenic polypeptide and to a host cell comprising the same. Moreover, the present invention relates to kits, methods, and uses related to the immunogenic polypeptide of the invention.

Cervical cancer is women's second most frequent cancer worldwide. Clinical and molecular studies have shown that certain types of human papillomavirus (HPV), referred to as high-risk types, are the etiological agents of this disease. Two anti-HPV vaccines for the prophylaxis of cervical cancer have been licensed recently by Merck (Gardasil™) and GlaxoSmithKline (Cervarix™) (Schmiedeskamp et al, (2006), Ann Pharmacother, 40: 1344-1352). Both vaccines rely on the major capsid protein L1 in the form of virus-like particles (VLPs) as antigen (Roden et al., (2006), Nat Rev Cancer, 6: 753-763); they protect against the HPV types from which the L1-VLPs were derived, yet are largely ineffective against all but the most closely related HPV types. The two most prominent high-risk HPV types, 16 and 18, are the major targets of both vaccines, although there is evidence for partial cross-protection against HPV types 31 and 45 (reviewed by Muller and Gissmann, (2007), Dis Markers, 23: 331-336; Huh and Roden, (2008), Gynecol Oncol, 109: S48-56). The limited cross-protective capacity of L1-based vaccines, which is the main reason for the continuing effort toward the development of improved vaccination strategies, likely reflects the HPV type specificity of L1 neutralizing epitopes (Giroglou et al., (2001), Vaccine, 19: 1783-1793).

Antibodies against the minor capsid protein L2 also neutralize HPV infection and are often capable to cross-neutralize various non-cognate virions, although with varying efficiencies (Kondo et al. (2007), Virology, 358: 266-272; Gambhira, R., (2007), J Virol, 81: 13927-13931). The N-terminal region of L2 interacts with an as yet unidentified secondary receptor on the surface of target cells (Yang et al. (2003), J Virol, 77: 3531-3541) and this interaction can be blocked by anti-L2 antibodies. The precise identity of the L2 region involved in HPV-cell surface interaction is still a matter of debate. This was initially proposed as the region comprised of amino acids (aa) 108-120, and antibodies targeting this particular L2 region were indeed shown to block viral infection in vitro albeit at low titers (Kawana et al. (2001), Vaccine, 19: 1496-1502; Kawana et al. (2001b), J Virol, 75: 2331-2336). Subsequent experiments identified additional neutralizing epitopes in the aa 1-88 region (Pastrana et al. (2005), Virology, 337: 365-372) as well as in more extended N-terminal regions comprised of aa 11-200 and aa 18-144 (Kondo loc. cit). Perhaps the most prominent of these N-terminal epitopes is the one located between aa 17-36. This was identified as the target of an HPV16 neutralizing and protective monoclonal antibody (RG-1) as well as the major determinant of the neutralizing activity found in sera from rabbits and humans immunized with extended versions of L2 (aa 1-88, 11-200 or the full-length protein) (Gambhira, 2007, loc cit.). Since it had been found that mutation of L2 amino acids 18 and 19 or of amino acids 20 and 21 disrupted both L2 binding to the cell surface and viral infection (Yang, R., et al. (2003), J. Virol. 77: 3531-3541), it was concluded that the epitope recognized by the RG-1 antibody overlaps the surface-binding motif of HPV16 L2.

Besides the lack of precise knowledge on the most relevant (cross) neutralizing epitope(s), a major problem with the use of L2 as a tool for HPV prophylaxis is the poor immunogenicity of the L2 protein and peptides thereof, as compared to L1-VLPs. A substantial increase in immunogenicity has been reported lately via chemical coupling of the HPV16 L2 peptide (17-36) to a broadly recognized T helper epitope and to the Toll-like receptor ligand dipalmitoyl S-glyceryl cysteine (Alphs et al. (2008), Proc Natl Acad Sci USA, 105: 5850-5855). Alternatively, L2 peptides have been fused to Adenovirus surface proteins (WO 2008/140474) or to other HPV proteins to increase immunogenicity (WO 2002/070004, de Jong et al. (2002), Vaccine, 20(29-30): 3456-3464). Also, multimeric L2 vaccines, comprising peptides from various genotypes, were used (Jagu et al. (2013), PLOS One 8(1): e55538).

A recently developed alternative strategy for increasing peptide immunogenicity relies on the use of thioredoxin (Trx) as a scaffold protein with the ability to constrain the structure of single-copy as well as multimeric (tandemly repeated) peptide epitopes inserted within its surface-exposed active site loop (Moretto et al. (2007), J Biol Chem, 282, 11436-11445). This strategy has also been used to present HPV L2 peptides for immunization (WO 2010/070052). For thioredoxin as scaffold protein, it was found that by using Trx variants from Archaebacteria, induction of anti-host thioredoxin antibodies can be significantly reduced (Canali et al. (2014), Scientific Reports 4, Art. No 4729:1).

Thus, the L1 polypeptide is highly immunogenic and antibodies against it show only a limited cross-protective capacity, whereas antibodies against the L2 polypeptide are capable of cross-neutralizing various HPV genotypes. The L2 polypeptide, however has only limited immunogenicity.

Therefore, immunogenic polypeptides that are highly immunogenic and allow for a cross-neutralization of various HPV genotypes without the drawbacks as referred to above are highly required. The technical problem underlying the present invention can be seen as the provision of means and methods for complying with the aforementioned needs. The technical problem is solved by the embodiments characterized in the claims and herein below.

Accordingly, the present invention relates to an immunogenic polypeptide comprising a multitude of human papillomavirus (HPV) L2 N-terminal peptides corresponding to amino acids 20 to 50 of the L2 polypeptide of HPV16, wherein said HPV L2 N-terminal peptides are L2 N-terminal peptides from at least two different HPV genotypes.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms "preferably", "more preferably", "most preferably", "particularly", "more particularly", "specifically", "more specifically" or similar terms are used in conjunction with optional features, without restricting further possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding further embodiments of the invention, without any restrictions regarding the scope of the invention and without any restriction regarding the possibility of combining the features introduced in such way with other optional or non-optional features of the invention. Moreover, if not otherwise indicated, the term "about" relates to the indicated value with the commonly accepted technical precision in the relevant field, preferably relates to the indicated value±20%, more preferably ±10%, more preferably ±5%.

The term "immunogenic polypeptide", as used herein, relates to a, preferably non-naturally occurring, polypeptide comprising a multitude of L2 N-terminal sequences as specified herein. The immunogenic polypeptide referred to herein comprises at least a multitude of human papillomavirus (HPV) L2 N-terminal peptides as specified herein. As specified herein below, the immunogenic polypeptide may comprise further domains, like, preferably, scaffold polypeptides, e.g. thioredoxin, immune enhancers, oligomerization domains, and the like. Preferably, said domains are linked by non-covalent bonds and have a dissociation constant of at most $10^{-6}$ mol/l, more preferably of at most $10^{-7}$ mol/l, most preferably at most $10^{-8}$ mol/l. More preferably, at least two domains are covalently connected, preferably by a peptide bond. Most preferably, all domains of the immunogenic polypeptide are covalently connected, preferably by peptide bonds; i.e. preferably, the immunogenic polypeptide is a polypeptide having a contiguous chain of amino acids. Thus, preferably, the immunogenic polypeptide is encoded by a single open reading frame. Preferably, the immunogenic polypeptide has the biological function of being an immunogenic polypeptide, inducing a humoral and/or a cellular immune response in a subject, more preferably inducing a humoral immune response in a subject. Most preferably, the immunogenic polypeptide has the biological function of inducing immunity to at least one, more preferably at least three, still more preferably at least eight, most preferably at least ten HPV genotypes.

Preferably, the term immunogenic polypeptide includes variants of the specific immunogenic polypeptides described herein. As used herein, the term "polypeptide variant" relates to any chemical molecule comprising at least the polypeptides as specified herein, having the indicated activity, but differing in structure from said polypeptide indicated herein. Preferably, the polypeptide variant comprises a peptide having an amino acid sequence corresponding to an amino acid sequence of from 25 to 500, more preferably of from 30 to 300, most preferably, of from 35 to 150 consecutive amino acids comprised in a polypeptide as specified herein. Moreover, also encompassed are further polypeptide variants of the aforementioned polypeptides. Such polypeptide variants have at least the same essential biological activity as the specific polypeptides. Moreover, it is to be understood that a polypeptide variant as referred to in accordance with the present invention shall have an amino acid sequence which differs due to at least one amino acid substitution, deletion and/or addition, wherein the amino acid sequence of the variant is still, preferably, at least 50%, 60%, 70%, 80%, 85%, 90%, 92%, 95%, 97%, 98%, or 99% identical with the amino acid sequence of the specific polypeptide. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the sequence it is compared to for optimal alignment. The percentage is calculated by determining, preferably over the full length of the peptide, the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman (1981), by the homology alignment algorithm of Needleman and Wunsch (1970), by the search for similarity method of Pearson and Lipman (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Polypeptide variants referred to above may be derived from allelic variants or any other species specific homologs, paralogs, or orthologs. Moreover, the polypeptide variants referred to herein include fragments of the specific polypeptides or the aforementioned types of polypeptide variants as long as these fragments and/or variants have the biological activity as referred to above. Such fragments may be or be derived from, e.g., degradation products or splice variants of the polypeptides. Further included are variants which differ due to posttranslational modifications such as phosphorylation, glycosylation, ubiquitinylation, sumoylation, or myristylation, by including non-natural amino acids, and/or by being peptidomimetics. Moreover, variants of the immunogenic polypeptide of the present invention, preferably, include variants wherein at least one domain is a variant of a domain described herein.

As used herein, the term "papillomavirus" (PV) relates to a DNA virus from the papillomaviridae family of viruses that infects the skin and mucous membranes of mammals, preferably livestock, more preferably cattle and horses, most preferably humans. For human PV (HPV), more than 110 HPV genotypes have been described (de Villiers, E. M., C. Fauquet, T. R. Broker, H. U. Bernard, and H. zur Hausen. 2004. Classification of papillomaviruses. Virology 324:17-27). Approximately 50 HPV genotypes are known to infect the mucosa. These mucosal genotypes are classified into three different groups based on their epidemiological association with cancer: "low-risk" human papillomaviruses (LR-HPV), "high-risk" human papillomaviruses (HR-HPV) and "putative high-risk" human papillomaviruses (pHR-HPV). It is also known that HR-HPVs can cause vulvar, anal, vaginal, penile, and oropharyngeal cancer, as well as vaginal intraepithelial neoplasia, anal intraepithelial neoplasia, vulvar intraepithelial neoplasia, and penile intraepithelial neoplasia. Preferably, HPVs are mucosal HPVs; more preferably, HPVs of the current invention are High-risk HPV genotypes (HR-HPVs), which are the main cause for the development of cervical cancer. Preferably, HPVs are HPV 31, 33, 35, 39, 45, 51, 52, 56, 58, 59, 68, 73 and 82, more preferably HPV 6, 16, 18, 31, 33, 35, 39, 45, 51, 56, 59 and 82, most preferably HPV 6, 16, 18, 31, 33, 35, 51 and 59.

The term "L2 N-terminal peptide" refers to a peptide having an amino acid sequence of a peptide occurring in the N-terminus of a HPV L2 polypeptide. HPV L2 polypeptides are known in the art. The full-length L2 polypeptide is one of the two capsid proteins of papillomaviruses and is also referred to as minor capsid protein. Together with the major capsid protein, L1, the full-length L2 polypeptide forms viral capsids. The L2 N-terminal peptide, in the context of the present invention corresponds to amino acids 20 to 50, preferably amino acids 20 to 38 of the L2 polypeptide of an HPV L2 polypeptide. As will be understood by the skilled person, the L2 polypeptides of the various HPV genotypes are not necessarily exactly colinear due to sequence variations, although preferred immunogenic epitopes share a similar sequence. Thus, for amino acid numbering, reference is frequently made to amino acid positions corresponding to the positions of corresponding amino acids in the HPV16 L2 amino acid sequence. Thus, preferably, the L2 N-terminal peptide, in the context of the present invention, corresponds to amino acids 20 to 50, preferably amino acids 20 to 38 of the L2 polypeptide of HPV16. Preferred L2 N-terminal peptides corresponding to amino acids 20 to 50 of the L2 polypeptide of HPV16 are those having the amino acid sequence of SEQ ID NO: 1 (HPV 16), SEQ ID NO: 2 (HPV 18), SEQ ID NO: 3 (HPV 45), SEQ ID NO: 4 (HPV 31), SEQ ID NO: 5 (HPV 33), SEQ ID NO: 6 (HPV 35), SEQ ID NO: 7 (HPV 59), SEQ ID NO: 8 (HPV 56), SEQ ID NO: 9 (HPV 51), SEQ ID NO: 10 (HPV 39), SEQ ID NO: 11 (HPV 82), or SEQ ID NO: 12 (HPV 6). Preferred L2 N-terminal peptides corresponding to amino acids 20 to 38 of the L2 polypeptide of HPV16 are those having the sequence of SEQ ID NO: 13 (HPV 16), SEQ ID NO: 14 (HPV 18), SEQ ID NO: 15 (HPV 45), SEQ ID NO: 16 (HPV 31), SEQ ID NO: 17 (HPV 33), SEQ ID NO: 18 (HPV 35), SEQ ID NO: 19 (HPV 59), SEQ ID NO: 20 (HPV 56), SEQ ID NO: 21 (HPV 51), SEQ ID NO: 22 (HPV 39), SEQ ID NO: 23 (HPV 82), or SEQ ID NO: 24 (HPV 6).

Preferably, the term L2 N-terminal peptide includes variants of the specific N2-terminal peptides as specified herein above. More preferably, variants of the N2-terminal peptides are variants comprising at most two, preferably at most one amino acid deletion(s), insertion(s) and/or substitution(s) per HPV L2 N-terminal peptide. More preferably, variants of the N2-terminal peptides are variants comprising at most two, preferably at most one amino acid substitution(s), preferably conservative substitution, per HPV L2 N-terminal peptide.

The term "multitude of HPV L2 N-terminal peptides" relates to a number of at least 3, preferably at least 5, more preferably 7, 8, 9, 10, 11, or 12, even more preferably 7, 8, or 9, most preferably 8 HPV L2 N-terminal peptides. Preferably, said multitude is a number of from 3 to 11, preferably of from 5 to 10, more preferably of from 7 to 9, most preferably 8 HPV L2 N-terminal peptides. Preferably, the immunogenic polypeptide comprises three copies, more preferably two copies, most preferably one copy of each of said HPV L2 N-terminal peptides.

Preferably, at least two, more preferably at least five, most preferably at least eight HPV L2 N-terminal peptides comprised in said immunogenic polypeptide are non-identical. Thus, preferably, the HPV L2 N-terminal peptides in said immunogenic polypeptide are L2 N-terminal peptides from at least two, more preferably at least five, even more preferably from 7, 8, 9, 10, 11, or 12, most preferably from 8, different HPV genotypes. Preferably, the HPV L2 N-terminal peptides in said immunogenic polypeptide comprise L2 N-terminal peptides of HPV genotypes 6, 16, 18, 31, 33, 35, 39, 45, 51, 56, 59 and 82 or variants thereof comprising at most two, preferably at most one amino acid substitution(s) per HPV L2 N-terminal peptide. More preferably, the HPV L2 N-terminal peptides in said immunogenic polypeptide comprise L2 N-terminal peptides of HPV genotypes 6, 16, 18, 31, 33, 35, 39, 45, 51, 56, 59 and 82. Also preferably, the HPV L2 N-terminal peptides comprise L2 N-terminal peptides of HPV genotypes 6, 16, 18, 31, 33, 35, 51, and 59 or variants thereof comprising at most two, preferably at most one amino acid substitution(s) per HPV L2 N-terminal peptide. More preferably, the HPV L2 N-terminal peptides in said immunogenic polypeptide comprise L2 N-terminal peptides of HPV genotypes 6, 16, 18, 31, 33, 35, 51, and 59.

Preferably, the immunogenic polypeptide exclusively comprises, preferably consists of, L2 N-terminal peptides of HPV genotypes 6, 16, 18, 31, 33, 35, 39, 45, 51, 56, 59 and 82 or variants thereof comprising at most two, preferably at most one amino acid substitution(s) per HPV L2 N-terminal peptide. More preferably, the immunogenic polypeptide exclusively comprises, preferably consists of, one copy each of L2 N-terminal peptides of HPV genotypes 6, 16, 18, 31, 33, 35, 51 and 59 or is a variant of said polypeptide comprising a multitude of HPV L2 N-terminal peptides comprising at most two, preferably at most one amino acid substitution(s) per HPV L2 N-terminal peptide. As used herein, the term "immunogenic polypeptide exclusively comprising" specific L2 N-terminal peptides relates to an immunogenic polypeptide comprising the indicated L2 N-terminal peptides, but not comprising further, non-indicated L2 N-terminal peptides; as will be understood, the term, thus, does not exclude that said immunogenic polypeptide comprises further, non-L2 N-terminal peptide elements, preferably polypeptide domains. Thus, preferably, an immunogenic polypeptide exclusively comprising L2 N-terminal peptides of HPV genotypes 6, 16, 18, 31, 33, 35, 51, and 59 may comprise any number of L2 N-terminal peptides of HPV genotypes 6, 16, 18, 31, 33, 35, 51, and 59, but no L2 N-terminal peptides of other HPV genotypes. Even more preferably, the immunogenic polypeptide exclusively comprises, preferably consists of, L2 N-terminal peptides of HPV genotypes 6, 16, 18, 31, 33, 35, 39, 45, 51, 56, 59 and 82. Still more preferably, the immunogenic polypeptide exclusively comprises, preferably consists of L2 N-terminal peptides of HPV genotypes 6, 16, 18, 31, 33, 35, 51, and 59. Most preferably, the immunogenic polypeptide exclusively comprises, preferably consists of, one copy each of L2 N-terminal peptides of HPV genotypes 6, 16, 18, 31, 33, 35, 51, and 59. Preferably, the immunogenic polypeptide comprises HPV L2 N-terminal peptides in the sequence HPV 16-18-31-33-35-39-45-51-56-59-82, more preferably comprises HPV L2 N-terminal peptides in the sequence HPV 16-18-31-33-35-6-51-59. More preferably, the immunogenic polypeptide comprises one copy of a peptide comprising one copy each of HPV L2 N-terminal peptides in the sequence HPV 16-18-31-33-35-39-45-51-56-59-82; most preferably, the immunogenic polypeptide comprises one copy of a peptide comprising one copy each of HPV L2 N-terminal peptides in the sequence HPV 16-18-31-33-35-6-51-59. Preferably, the immunogenic polypeptide is devoid of an L2 N-terminal peptide of HPV genotype(s) 39, 45, 56, and/or 82.

Preferably, the HPV L2 N-terminal peptides are comprised in the immunogenic polypeptide in a directly contiguous sequence, i.e. not comprising intervening amino acids. More preferably, the HPV L2 N-terminal peptides in the immunogenic polypeptide are separated by one or more linker sequences, wherein said linker sequences may be identical or may be different for the respective L2 N-terminal peptides intervened. Preferably, the linker consists of 5, 3 or 2 amino acids consisting of proline (P) and glycine (G) residues. More preferably, the HPV L2 N-terminal peptides in the immunogenic polypeptide are separated by GGP and/or GGGP linker sequences.

Preferably, the multitude of HPV L2 N-terminal peptides comprises the amino acid sequence, more preferably the multitude of HPV L2 N-terminal peptides consists of the amino acid sequence of SEQ ID NOs: 25 or 26, preferably SEQ ID NO: 25; or is a variant of said sequence comprising at most two, preferably at most one amino acid substitution(s) per HPV L2 N-terminal peptide. More preferably, the multitude HPV L2 N-terminal peptides comprises the amino acid sequence, more preferably the multitude HPV L2 N-terminal peptides consists of an amino acid sequence selected from SEQ ID NOs: 25 or 26, preferably SEQ ID NO: 25. Thus, preferably, immunogenic polypeptide comprises, preferably consists of the amino acid sequence of SEQ ID NO: 25 or 26, preferably SEQ ID NO: 25 or is a variant of said sequence. More preferably, immunogenic polypeptide comprises, preferably consists of the amino acid sequence of SEQ ID NO: 25 or 26, preferably SEQ ID NO: 25.

Preferably, the immunogenic polypeptide further comprises an oligomerization domain. The term "oligomerization domain" is used in its conventional meaning and relates to a polypeptide having the property that polypeptides comprising said domain have a propensity to aggregate. Preferably, the dissociation constant for the oligomerization domain as a separate molecule is at most $10^{-4}$ mol/l, more preferably at most $10^{-5}$ mol/l, most preferably at least $10^{-6}$ mol/l. As will be appreciated, the number of molecules aggregating will in particular depend on the type of oligomerization domain selected. Suitable oligomerization domains are known in the art. Preferably, the immunogenic polypeptide comprises at least one oligomerization domain of (i) an oligomerization domain of a C4-binding protein, preferably of a mammalian C4-binding protein, more preferably of a human or mouse C4-binding protein, most preferably of a mouse C4-binding protein; (ii) an encapsulin polypeptide, preferably an encapsulin polypeptide from a thermophilic archaebacterium, more preferably a *Pyrococcus furiosus* encapsulin polypeptide; (iii) a ferritin polypeptide, preferably a ferritin polypeptide from a thermophilic archaebacterium, more preferably a *Pyrococcus furiosus* ferritin polypeptide; and (iv) a hybrid polypeptide of two different chicken C4-binding proteins, preferably an IMX313 polypeptide or a variant thereof, in particular as described in WO 2007/062819 A2, most preferably an IMX313T polypeptide (SEQ ID NO:60, preferably encoded by SEQ ID NO:61). Preferably, the oligomerization domain comprises a sequence of SEQ ID NO: 55 (*P. furiosus* encapsulin); or comprises a sequence of SEQ ID NO: 56 (*P. furiosus* ferritin).

Also preferably, the immunogenic polypeptide further comprises an enhancer of immunogenicity, preferably at the N-terminus and/or at the C-terminus of said immunogenic polypeptide. Peptide sequences functioning as enhancers of immunogenicity are, in principle, known in the art. Preferably, the enhancer of immunogenicity is CD4+ T-helper epitope, preferably an epitope comprising at least one of (i) p25 from the carboxyl region of *Plasmodium vivax* circumsporozoite protein; (ii) p2 peptide from tetanus toxin; (iii) p30 peptide from tetanus toxin; and (iv) a Pan HLA-DR reactive epitope (PADRE). More preferably, the enhancer of immunogenicity comprises, preferably consists of, a peptide comprising the amino acid sequence of SEQ ID NO: 57 (PADRE), SEQ ID NO: 58 (p30), and/or SEQ IS NO: 59 (p25). Also preferably, the enhancer of immunogenicity is a peptide comprising the amino acid sequence RGD, known to be an integrin binding motif.

In a preferred embodiment, the multitude of L2 N-terminal peptides is comprised in a thioredoxin polypeptide. Thioredoxin polypeptides suitable for including L2 N-terminal peptides are known in the art from WO 2010/070052. Preferably, the thioredoxin is a mammalian, more preferably human, a bacterial, or an archaebacterial thioredoxin. More preferably, the thioredoxin is an archaebacterial thioredoxin, preferably from a thermophilic archaebacterium, preferably of *Pyrococcus furiosus* or of *Methanosaeta thermophila*. Thus, the thioredoxin preferably has the amino acid sequence of SEQ ID NO: 49 (human thioredoxin), preferably encoded by the nucleic acid sequence of SEQ ID NO: 50, or is a variant thereof; or has the amino acid sequence of SEQ ID NO: 47 (mouse thioredoxin), preferably encoded by the nucleic acid sequence of SEQ ID NO: 48, or is a variant thereof; or has the amino acid sequence of SEQ ID NO: 45 (*E. coli* thioredoxin), preferably encoded by the nucleic acid sequence of SEQ ID NO: 46, or is a variant thereof. More preferably, the thioredoxin has the amino acid sequence of SEQ ID NO: 53 (*P. furiosus* thioredoxin), preferably encoded by the nucleic acid sequence of SEQ ID NO: 54, or is a variant thereof; or has the amino acid sequence of SEQ ID NO: 51 (*M. thermophila* thioredoxin), preferably encoded by the nucleic acid sequence of SEQ ID NO: 52, or is a variant thereof. As will be understood by the skilled person, the thioredoxins of the present invention have the biological activity of being a scaffold for the L2 N-terminal peptides, whereas the redox-activity is not required. Accordingly, according to the present invention, variant thioredoxins with a sequence identity of at least 50% to one of the aforesaid thioredoxins are suitable for use in the immunogenic polypeptide. Preferably, the multitude of L2 N-terminal peptides is inserted into the display site of the thioredoxin, as described in detail in WO 2010/070052.

Preferably, the thioredoxin and/or the oligomerization domain and/or the enhancer of immunogenicity have less than 50%, more preferably less than 35%, even more preferably less than 25%, most preferably less than 20% amino acid sequence identity to a human polypeptide, preferably to any human polypeptide identified in assembly GRCh38.p7 of the human genome. More preferably, the thioredoxin and/or the oligomerization domain have less than 50%, more preferably less than 35%, even more preferably less than 25%, most preferably less than 20% amino acid sequence identity to a human polypeptide, preferably to any human polypeptide identified in assembly GRCh38.p7 of the human genome. Also preferably, the thioredoxin and/or the oligomerization domain and/or the enhancer of immunogenicity are polypeptides derived from archaebacterial polypeptides. More preferably, the thioredoxin and/or the oligomerization domain are polypeptides derived from archaebacterial polypeptides.

As will be understood, the aforesaid domains may also be combined in an essentially arbitrary fashion. Preferred combinations are the following:

An immunogenic polypeptide comprising the amino acid sequence of SEQ ID NO: 27, preferably encoded by a polynucleotide comprising the nucleic acid sequence of SEQ ID NO: 28.

An immunogenic polypeptide comprising the amino acid sequence of SEQ ID NO: 29, preferably encoded by a polynucleotide comprising the nucleic acid sequence of SEQ ID NO: 30.

An immunogenic polypeptide comprising the amino acid sequence of SEQ ID NO: 31, preferably encoded by a polynucleotide comprising the nucleic acid sequence of SEQ ID NO: 32.

An immunogenic polypeptide comprising the amino acid sequence of SEQ ID NO: 33.

An immunogenic polypeptide comprising the amino acid sequence of SEQ ID NO: 34, preferably encoded by a polynucleotide comprising the nucleic acid sequence of SEQ ID NO: 35.

An immunogenic polypeptide comprising the amino acid sequence of SEQ ID NO: 36, preferably encoded by a polynucleotide comprising the nucleic acid sequence of SEQ ID NO: 37.

An immunogenic polypeptide comprising the amino acid sequence of SEQ ID NO: 38.

An immunogenic polypeptide comprising the amino acid sequence of SEQ ID NO: 39, preferably encoded by a polynucleotide comprising the nucleic acid sequence of SEQ ID NO: 40.

An immunogenic polypeptide comprising the amino acid sequence of SEQ ID NO: 41, preferably encoded by a polynucleotide comprising the nucleic acid sequence of SEQ ID NO: 42.

An immunogenic polypeptide comprising the amino acid sequence of SEQ ID NO: 43, preferably encoded by a polynucleotide comprising the nucleic acid sequence of SEQ ID NO: 44.

The term "subject", as used herein, relates to an animal, preferably a vertebrate, more preferably a mammal, in particular to livestock like cattle, horse, pig, sheep, and goat, or to a laboratory animal like a rat, mouse, and guinea pig. Most preferably, the subject is a human.

Advantageously, it was found in the work underlying the present invention that polypeptides comprising a multitude of non-identical HPV L2 N-terminal peptides induce improved immunity to HPV and, in particular, mediate improved cross-immunity. This effect was particularly pronounced for polypeptides comprising peptides from eight to eleven HPV genotypes, polypeptides with peptides from eight genotypes surprisingly having best performance.

The definitions made above apply mutatis mutandis to the following. Additional definitions and explanations made further below also apply for all embodiments described in this specification mutatis mutandis.

The present invention further relates to an immunogenic polypeptide of the present invention for use in medicine. The present invention also relates to an immunogenic polypeptide of the present invention for use in vaccination against HPV infection.

The term "vaccination against HPV infection" as used herein, preferably, relates to administering the compounds as specified herein to elicit an immune response against various HPV genotypes. Thus, vaccination stimulates the immune system and establishes or improves immunity to infection with various HPV genotypes. Preferably, vaccination according to the present invention allows for establishing or improving immunity to infection with human papillomavirus genotypes 6, 16, 18, 31, 33, 35, 51, and 59. Preferably, the vaccine according to the present invention also allows for establishing or improving immunity to infection with at least the human papillomavirus genotypes 5, 6, 11, 16, 18, 31, 33, 35, 39, 45, 51 and 59. In a preferred embodiment, vaccination according to the present invention allows for establishing or improving immunity to infection with human papillomavirus genotypes 31, 35, and 51. It is to be understood that the vaccine according to the present invention may comprise further components, in particular as specified elsewhere herein. The skilled person will understand that vaccination may not elicit a significant immune response in all subjects vaccinated. Also, it is to be understood that vaccination may not be effective to prevent infection in all subjects vaccinated. However, the term requires that a, preferably statistically significant, portion of subjects of a cohort or population are effectively vaccinated. Whether a portion is statistically significant can be determined without further ado by the person skilled in the art using various well known statistic evaluation tools, e.g., determination of confidence intervals, p-value determination, Student's t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the treatment shall be effective for at least 60%, at least 70%, at least 80%, or at least 90% of the subjects of a given cohort or population.

Preferably, vaccination further comprises administration of an adjuvant, preferably simultaneously to administration of the immunogenic polypeptide. More preferably, the immunogenic polypeptide and the adjuvant are comprised in a common mixture at administration. Thus, preferably, the immunogenic polypeptide and the adjuvant are mixed before administration. Preferably, the adjuvant comprises (i) alum and a toll like receptor 4 (TLR4) antagonist, preferably synthetic monophosphoryl lipid A (MPLA), and/or (ii) a squalene-based oil-in-water nano-emulsion, preferably AddaVax™.

Preferably, vaccination against HPV infection of the present invention induces a humoral immune response in a subject, i.e., preferably induces the production of antibodies recognizing, preferably specifically recognizing, an HPV L2 polypeptide. The term "specifically recognizing" is understood by the skilled person as the property of a binding agent, e.g. an antibody, to specifically bind to a particular species of molecule, while other molecules from the same chemical class of molecules, e.g. proteins, are not recognized or are recognized to a much lesser extent. Preferably, the binding constant of an antibody specifically recognizing a HPV L2 polypeptide for a HPV L2 polypeptide is at least a factor 100, more preferably at least a factor of at least 1000, most preferably a factor of at least 10000 lower than for any non-HPV L2 polypeptide. Preferably, the antibodies specifically recognizing an HPV L2 polypeptide are antibodies specifically recognizing an HPV capsid. Preferably, the antibodies specifically recognizing an HPV L2 polypeptide are antibodies neutralizing an HPV capsid. Preferably, vaccination against HPV infection induces a humoral and a cellular immune response in a subject.

Accordingly, the present invention also relates to an immunogenic polypeptide according to the present invention for use in generating antibodies specifically recognizing an HPV L2 polypeptide.

Further, the present invention relates to a polynucleotide encoding the immunogenic polypeptide according to the present invention.

As used herein, the term polynucleotide, preferably, includes variants of the specifically indicated polynucleotides. More preferably, the term polynucleotide relates to the specific polynucleotides indicated. The term "polynucleotide variant", as used herein, relates to a variant of a polynucleotide related to herein comprising a nucleic acid sequence characterized in that the sequence can be derived from the aforementioned specific nucleic acid sequence by at least one nucleotide substitution, addition and/or deletion, wherein the polynucleotide variant shall have the activity as specified for the specific polynucleotide. Moreover, it is to be understood that a polynucleotide variant as referred to in accordance with the present invention shall have a nucleic acid sequence which differs due to at least one nucleotide substitution, deletion and/or addition. Preferably, said polynucleotide variant is an ortholog, a paralog or another homolog of the specific polynucleotide. Also preferably, said polynucleotide variant is a naturally occurring allele of the specific polynucleotide. Polynucleotide variants also encompass polynucleotides comprising a nucleic acid sequence which is capable of hybridizing to the aforementioned specific polynucleotides, preferably, under stringent hybridization conditions. These stringent conditions are known to the skilled worker and can be found in Current Protocols in Molecular Biology, John Wiley & Sons, N. Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1× to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably, for example, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, polynucleotide variants are obtainable by PCR-based techniques such as mixed oligonucleotide primer-based amplification of DNA, i.e. using degenerated primers against conserved domains of a polypeptide of the present invention. Conserved domains of a polypeptide may be identified by a sequence comparison of the nucleic acid sequence of the polynucleotide or the amino acid sequence of the polypeptide of the present invention with sequences of other organisms. As a template, DNA or cDNA from bacteria, fungi, plants or, preferably, from animals may be used. Further, variants include polynucleotides comprising nucleic acid sequences which are at least 70%, at least 75%, at least 80%, at least 85%, at least 90%, at least 95%, at least 98% or at least 99% identical to the specifically indicated nucleic acid sequences. Moreover, also encompassed are polynucleotides which comprise nucleic acid sequences encoding amino acid sequences which are at least 70%, at least 75%, at least 80%, at least 85%, at least 90%, at least 95%, at least 98% or at least 99% identical to the amino acid sequences specifically indicated. The percent identity values are, preferably, calculated over the entire amino acid or nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970)) and Smith and Waterman (Adv. Appl. Math. 2; 482-489 (1981))], which are part of the GCG software packet (Genetics Computer Group, 575 Science Drive, Madison, Wis., USA 53711 (1991)), are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

A polynucleotide comprising a fragment of any of the specifically indicated nucleic acid sequences is also encompassed as a variant polynucleotide of the present invention. The fragment shall still encode an immunogenic polypeptide which still has the activity as specified. Accordingly, the immunogenic polypeptide encoded may comprise or consist of the domains of the immunogenic polypeptide of the present invention conferring the said biological activity. A fragment as meant herein, preferably, comprises at least 50, at least 100, at least 250 or at least 500 consecutive nucleotides of any one of the specific nucleic acid sequences or encodes an amino acid sequence comprising at least 20, at least 30, at least 50, at least 80, at least 100 or at least 150 consecutive amino acids of any one of the specific amino acid sequences.

The polynucleotides of the present invention either consist, essentially consist of, or comprise the aforementioned nucleic acid sequences. Thus, they may contain further nucleic acid sequences as well. Specifically, the polynucleotides of the present invention may encode fusion proteins wherein one partner of the fusion protein is an immunogenic polypeptide being encoded by a nucleic acid sequence recited above. Such fusion proteins may comprise as additional part polypeptides for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and are described elsewhere herein.

The polynucleotide of the present invention shall be provided, preferably, either as an isolated polynucleotide (i.e. isolated from its natural context) or in genetically modified form. The polynucleotide, preferably, is DNA, including cDNA, or is RNA. The term encompasses single as well as double stranded polynucleotides. Moreover, preferably, comprised are also chemically modified polynucleotides including naturally occurring modified polynucleotides such as glycosylated or methylated polynucleotides or artificial modified one such as biotinylated polynucleotides.

Furthermore, the present invention relates to a vector comprising the polynucleotide according to the present invention.

The term "vector", preferably, encompasses phage, plasmid, viral or retroviral vectors as well artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the polynucleotide of the present invention, preferably, further comprises selectable markers for propagation and/or selection in a host. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerenes. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells. In a preferred embodiment, the vector is a bacterial vector, preferably having a p15A origin of replication and/or carrying a kanamycin resistance gene.

More preferably, in the vector of the invention the polynucleotide is operatively linked to expression control sequences allowing expression in prokaryotic or eukaryotic cells or isolated fractions thereof. Expression of said polynucleotide comprises transcription of the polynucleotide, preferably into a translatable mRNA. Regulatory elements ensuring expression in eukaryotic cells, preferably mammalian cells, are well known in the art. They, preferably, comprise regulatory sequences ensuring initiation of transcription and, optionally, poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Moreover, inducible expression control sequences may be used in an expression vector encompassed by the present invention. Such inducible vectors may comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pBluescript (Stratagene), pCDM8, pRc/CMV, pcDNA1, pcDNA3 (InVitrogene) or pSPORT1 (GIBCO BRL). Preferably, said vector is an expression vector and a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). In a preferred embodiment, the vector is a bacterial expression vector carrying the nucleic acid sequence encoding the immunogenic polypeptide under the control of the tac promoter; thus more preferably, said vector additionally carries a gene encoding an expressible gene encoding a functional lac inhibitor.

Thus, in a preferred embodiment, the vector is a bacterial expression vector, preferably having a p15A origin of replication, carrying a kanamycin resistance gene, a gene encoding an expressible gene encoding a functional lac inhibitor, and encoding the immunogenic polypeptide under the control of the tac promoter. More preferably, the vector is a vector comprising the sequence of SEQ ID NO: 82.

The present invention also relates to a host cell comprising the polynucleotide according to the present invention and/or the vector according to the present invention.

As used herein, the term "host cell" relates to any cell capable of receiving and, preferably maintaining, the polynucleotide and/or the vector of the present invention. More preferably, the host cell is capable of expressing an immunogenic polypeptide of the present invention encoded on said polynucleotide and/or vector. Preferably, the cell is a bacterial cell, more preferably a cell of a common laboratory bacterial strain known in the art, most preferably an *Escherichia* strain, in particular an *E. coli* strain. Also preferably, the host cell is an eukaryotic cell, preferably a yeast cell, e.g. a cell of a strain of baker's yeast, or is an animal cell. More preferably, the host cell is an insect cell or a mammalian cell, in particular a mouse or rat cell. Most preferably, the host cell is a mammalian cell.

The present invention further relates to a pharmaceutical composition comprising the immunogenic polypeptide according to the present invention, the polynucleotide according the present invention, the vector according the present invention, and/or the host cell according to the present invention; and a pharmaceutically acceptable carrier.

The term "pharmaceutical composition", as used herein, relates to a composition comprising the compound or compounds of the present invention in a pharmaceutically acceptable form and a pharmaceutically acceptable carrier. The compounds of the present invention can be formulated as pharmaceutically acceptable salts. Acceptable salts comprise acetate, methylester, HCl, sulfate, chloride and the like. The pharmaceutical compositions are, preferably, administered topically or systemically. Suitable routes of administration conventionally used for drug administration are oral, intravenous, or parenteral administration as well as inhalation. Preferably, the pharmaceutical composition of the present invention is administered via a parenteral route, preferably subcutaneously, intramuscularly, or intraperitoneally. In case the subject is a human, administration preferably is intramuscularly. However, polynucleotide compounds may also be administered in a gene therapy approach by using viral vectors, viruses or liposomes, and may also be administered topically, e.g. as an ointment. Moreover, the compounds can be administered in combination with other drugs either in a common pharmaceutical composition or as separated pharmaceutical compositions wherein said separated pharmaceutical compositions may be provided in form of a kit of parts. In particular, co-administration of adjuvants is envisaged, as specified elsewhere herein. Preferably, the immunogenic polypeptide, the polynucleotide and the pharmaceutical composition are provided in lyophilized form.

The compounds are, preferably, administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables.

The carrier(s) must be acceptable in the sense of being compatible with the other ingredients of the formulation and being not deleterious to the recipient thereof. The pharmaceutical carrier employed may be, for example, either a solid, a gel or a liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl monostearate or glyceryl distearate alone or with a wax. Said suitable carriers comprise those mentioned above and others well known in the art, see, e.g., Remington's Pharmaceutical Sciences, Mack Publishing Company, Easton, Pa.

The diluent(s) is/are preferably selected so as not to affect the biological activity of the immunogenic polypeptide, polynucleotide, vector, or host cell and potential further pharmaceutically active ingredients. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

A therapeutically effective dose refers to an amount of the compounds to be used in a pharmaceutical composition of the present invention which prevents, ameliorates or treats a condition referred to herein. Therapeutic efficacy and toxicity of compounds can be determined by standard pharmaceutical procedures in cell culture or in experimental animals, e.g., by determining the ED50 (the dose therapeutically effective in 50% of the population) and/or the LD50 (the dose lethal to 50% of the population). The dose ratio between therapeutic and toxic effects is the therapeutic index, and it can be expressed as the ratio, LD50/ED50.

The dosage regimen will be determined by the attending physician, preferably taking into account relevant clinical factors and, preferably, in accordance with any one of the methods described elsewhere herein. As is well known in the medical arts, a dosage for any one patient may depend upon many factors, including the patient's size, body surface area, age, the particular compound to be administered, sex, time and route of administration, general health, and other drugs being administered concurrently. Progress can be monitored by periodic assessment. A typical dose can be, for example, in the range of 1 µg to 10000 µg, preferably per day; however, doses below or above this exemplary range are envisioned, especially considering the aforementioned factors. Generally, the regimen as a regular administration of the pharmaceutical composition should be in the range of 1 µg to 10 mg units per day. If the regimen is a continuous infusion, it should also be in the range of 1 µg to 10 mg units per kilogram of body weight per hour, respectively. However, depending on the subject and the mode of administration, the quantity of substance administration may vary over a wide range to provide from about 0.01 mg per kg body mass to about 10 mg per kg body mass, preferably. The pharmaceutical compositions and formulations referred to herein are administered at least once in order to treat or prevent a disease or condition recited in this specification. However, the said pharmaceutical compositions may be administered more than one time, for example from one to four times daily up to a non-limited number of days.

Specific pharmaceutical compositions are prepared in a manner well known in the pharmaceutical art and comprise at least an immunogenic polypeptide, polynucleotide, vector, or host cell as an active compound in admixture or otherwise associated with a pharmaceutically acceptable carrier or diluent. For making those specific pharmaceutical compositions, the active compound(s) will usually be mixed with a carrier or the diluent, or enclosed or encapsulated in a capsule, sachet, cachet, paper or other suitable containers or vehicles. The resulting formulations are to be adopted to the mode of administration, i.e. in the forms of tablets, capsules, suppositories, solutions, suspensions or the like. Dosage recommendations shall be indicated in the prescriber or user instructions in order to anticipate dose adjustments depending on the considered recipient.

The present invention further relates to a kit comprising an immunogenic polypeptide according to the present invention and an adjuvant.

Moreover, the present invention relates to a method of vaccinating a subject against HPV infection comprising
(a) contacting said subject with an immunogenic polypeptide according to the present invention, a polynucleotide according to the present invention, a vector according to the present invention, and/or a host cell according to the present invention, and
(b) thereby, vaccinating said subject against HPV infection.

The method of vaccinating of the present invention, preferably, is an in vivo method. Moreover, it may comprise steps in addition to those explicitly mentioned above. For example, further steps may relate, e.g., to contacting said subject with an adjuvant as specified elsewhere herein, and/or repeating said contacting with a compound of the present invention to enhance immune response. In the method of vaccinating, the subject, preferably, is a mammal, more preferably is a human.

Moreover, the present invention relates to a method for producing antibodies against an HPV L2 polypeptide, comprising
(a) contacting a subject with an immunogenic polypeptide according to the present invention, a polynucleotide according to the present invention, a vector according to the present invention, and/or a host cell according to the present invention, and
(b) harvesting antibodies generated by said subject from a bodily fluid of said subject and/or harvesting cells producing said antibodies from said subject.

The method for producing antibodies of the present invention, preferably, is an in vivo method performed on a, preferably non-human, subject. Preferably, the non-human subject is sacrificed after the method is performed. Moreover, the method may comprise steps in addition to those explicitly mentioned above. For example, further steps may relate, e.g., to purifying the antibodies harvested, or fusing the cells harvested to generate cell lines producing monoclonal antibodies according to well known methods. Also, one or more of the method steps may be performed by automated equipment.

In view of the above, the following embodiments are preferred:

1. An immunogenic polypeptide comprising a multitude of human papillomavirus (HPV) L2 N-terminal peptides corresponding to amino acids 20 to 50 of the L2 polypeptide of HPV16, wherein said HPV L2 N-terminal peptides are L2 N-terminal peptides from at least two different HPV genotypes.
2. The immunogenic polypeptide of embodiment 1, wherein said multitude is a number of at least 3, preferably at least 5, more preferably 7, 8, 9, 10, 11, or 12, even more preferably 7, 8, or 9, most preferably 8 HPV L2 N-terminal peptides.
3. The immunogenic polypeptide of embodiment 1 or 2, wherein said multitude is a number of from 3 to 11, preferably of from 5 to 10, more preferably of from 7 to 9, most preferably 8 HPV L2 N-terminal peptides.
4. The immunogenic polypeptide of any one of embodiments 1 to 3, wherein said HPV L2 N-terminal peptides are peptides corresponding to amino acids 20 to 38 of the L2 polypeptide of HPV16.
5. The immunogenic polypeptide of any one of embodiments 1 to 4, wherein said HPV L2 N-terminal peptides are L2 N-terminal peptides from at least four, preferably at least five, more preferably 7, 8, 9, 10, 11, or 12, most preferably 8, different HPV genotypes; or are variants thereof comprising at most two, preferably at most one amino acid substitution(s) per HPV L2 N-terminal peptide.
6. The immunogenic polypeptide of any one of embodiments 1 to 5, wherein said HPV L2 N-terminal peptides are L2 N-terminal peptides from at least four, preferably at least five, more preferably 7, 8, 9, 10, 11, or 12, most preferably 8, different HPV genotypes.
7. The immunogenic polypeptide of any one of embodiments 1 to 6, wherein said HPV L2 N-terminal peptides comprise L2 N-terminal peptides of HPV genotypes 6, 16, 18, 31, 33, 35, 39, 45, 51, 56, 59 and 82 or variants thereof comprising at most two, preferably at most one amino acid substitution(s) per HPV L2 N-terminal peptide; preferably wherein said HPV L2 N-terminal peptides comprise L2 N-terminal peptides of HPV genotypes 6, 16, 18, 31, 33, 35, 51, and 59 or variants thereof comprising at most two, preferably at most one amino acid substitution(s) per HPV L2 N-terminal peptide.
8. The immunogenic polypeptide of any one of embodiments 1 to 7, wherein said HPV L2 N-terminal peptides comprise L2 N-terminal peptides of HPV genotypes 6, 16, 18, 31, 33, 35, 39, 45, 51, 56, 59 and 82; preferably wherein said HPV L2 N-terminal peptides comprise L2 N-terminal peptides of HPV genotypes 6, 16, 18, 31, 33, 35, 51 and 59.
9. The immunogenic polypeptide of any one of embodiments 1 to 8, wherein said immunogenic polypeptide comprises three copies, more preferably two copies, most preferably one copy of each of said HPV L2 N-terminal peptides.
10. The immunogenic polypeptide of any one of embodiments 1 to 9, wherein said immunogenic polypeptide exclusively comprises, preferably consists of, L2 N-terminal peptides of HPV genotypes 6, 16, 18, 31, 33, 35, 39, 45, 51, 56, 59 and 82 or variants thereof comprising at most two, preferably at most one amino acid substitution(s) per HPV L2 N-terminal peptide.
11. The immunogenic polypeptide of any one of embodiments 1 to 10, wherein said immunogenic polypeptide exclusively comprises, preferably consists of, L2 N-terminal peptides of HPV genotypes 6, 16, 18, 31, 33, 35, 39, 45, 51, 56, 59 and 82.
12. The immunogenic polypeptide of any one of embodiments 1 to 11, wherein said immunogenic polypeptide exclusively comprises, preferably consists of, one copy each of L2 N-terminal peptides of HPV genotypes 6, 16, 18, 31, 33, 35, 51, and 59 or is a variant of said polypeptide comprising a multitude of HPV L2 N-terminal peptides comprising at most two, preferably at most one amino acid substitution(s) per HPV L2 N-terminal peptide.
13. The immunogenic polypeptide of any one of embodiments 1 to 12, wherein said immunogenic polypeptide exclusively comprises, preferably consists of, one copy each of L2 N-terminal peptides of HPV genotypes 6, 16, 18, 31, 33, 35, 51 and 59.
14. The immunogenic polypeptide of any one of embodiments 1 to 13, wherein said immunogenic polypeptide comprises said HPV L2 N-terminal peptides in the sequence HPV 16-18-31-33-35-39-45-51-56-59-82, more preferably in the sequence HPV 16-18-31-33-35-6-51-59, preferably in a directly contiguous sequence, more preferably separated by a 5, 3 or 2 amino acid linker.
15. The immunogenic polypeptide of any one of embodiments 1 to 14, wherein said multitude HPV L2 N-terminal peptides comprises, preferably consists of SEQ ID NO: 25 or 26 or is a variant of said immunogenic polypeptide comprising at most two, preferably at most one amino acid substitution(s) per HPV L2 N-terminal peptide.
16. The immunogenic polypeptide of any one of embodiments 1 to 15, wherein said immunogenic polypeptide comprises, preferably consists of the amino acid sequence of SEQ ID NO: 25 or 26.
17. The immunogenic polypeptide of any one of embodiments 1 to 16, wherein said immunogenic polypeptide is devoid of an L2 N-terminal peptide of HPV genotype(s) 39, 45, 56, and/or 82.
18. The immunogenic polypeptide of any one of embodiments 1 to 17, further comprising an oligomerization domain, preferably wherein said oligomerization domain is at least one of
  (i) an oligomerization domain of a C4-binding protein, preferably of a mammalian C4-binding protein, more preferably of a human or mouse C4-binding protein, most preferably of a mouse C4-binding protein;
  (ii) an encapsulin polypeptide, preferably an encapsulin polypeptide from a thermophilic archaebacterium, more preferably a *Pyrococcus furiosus* encapsulin polypeptide;
  (iii) a ferritin polypeptide, preferably a ferritin polypeptide from a thermophilic archaebacterium, more preferably a *Pyrococcus furiosus* ferritin polypeptide; and
  (iv) a hybrid polypeptide of two different chicken C4-binding proteins, preferably an IMX313Tpolypeptide.
19. The immunogenic polypeptide of any one of embodiments 1 to 18, wherein said oligomerization domain comprises, preferably consists of, SEQ ID NO: 55 or 56.

20. The immunogenic polypeptide of any one of embodiments 1 to 19, wherein said immunogenic polypeptide further comprises an enhancer of immunogenicity, preferably at the N-terminus and/or at the C-terminus of said immunogenic polypeptide.
21. The immunogenic polypeptide of embodiment 20, wherein said enhancer of immunogenicity is a CD4+ T-helper epitope or is a peptide comprising the amino acid sequence RGD.
22. The immunogenic polypeptide of embodiment 21, wherein said CD4+ T-helper epitope comprises at least one of
  (i) p25 from the carboxyl region of *Plasmodium vivax* circumsporozoite protein;
  (ii) p2 peptide from tetanus toxin;
  (iii) p30 peptide from tetanus toxin; and
  (iv) a Pan HLA-DR reactive epitope (PADRE).
23. The immunogenic polypeptide of any one of embodiments 21 or 22, wherein said CD4+ T-helper epitope comprises, preferably consists of, SEQ ID NO: 57.
24. The immunogenic polypeptide of any one of embodiments 1 to 23, wherein said multitude of HPV L2 N-terminal peptides is comprised in a thioredoxin polypeptide.
25. The immunogenic polypeptide of any one of embodiments 1 to 24, wherein said thioredoxin is a human, bacterial, or an archaebacterial thioredoxin.
26. The immunogenic polypeptide of any one of embodiments 1 to 25, wherein said thioredoxin is a thioredoxin of a thermophilic archaebacterium, preferably of *Pyrococcus furiosus*, preferably having the sequence of SEQ ID NO: 53.
27. The immunogenic polypeptide of any one of embodiments 1 to 26, wherein said multitude of HPV L2 N-terminal peptides is comprised in the display site of said thioredoxin.
28. The immunogenic polypeptide of any one of embodiments 1 to 27, wherein said immunogenic polypeptide is a fusion polypeptide, preferably wherein the elements of said immunogenic polypeptide are contiguous in amino acid sequence.
29. An immunogenic polypeptide according to any one of embodiments 1 to 28 for use in medicine.
30. An immunogenic polypeptide according to any one of embodiments 1 to 28 for use in vaccination against HPV infection.
31. The immunogenic polypeptide for use of embodiment 27, wherein said vaccination is vaccination against at least the HPV genotype 6, 16, 18, 31, 33, 35, 51, and 59 infection, preferably is vaccination against at least the HPV genotype 5, 6, 11, 16, 18, 31, 33, 35, 39, 45, 51 and 59 infection.
32. The immunogenic polypeptide for use of embodiment 30 or 31, wherein said vaccination is vaccination against HPV genotype 31, 35 and 51 infection.
33. The immunogenic polypeptide for use of any one of embodiments 30 to 32, wherein said vaccination further comprises administering an adjuvant, said adjuvant preferably comprising (i) alum and a toll like receptor 4 (TLR4) antagonist, preferably synthetic monophosphoryl lipid A (MPLA), and/or (ii) a squalene-based oil-in-water nano-emulsion, preferably AddaVax™.
34. A immunogenic polypeptide according to any one of embodiments 1 to 28 for use in generating antibodies specifically recognizing an HPV L2 polypeptide.
35. A polynucleotide encoding the immunogenic polypeptide according to any one of embodiments 1 to 28.
36. A vector comprising the polynucleotide according to embodiment 35.
37. A host cell comprising the polynucleotide according to embodiment 35 and/or the vector according to embodiment 36.
38. A pharmaceutical composition comprising the immunogenic polypeptide according to any one of embodiments 1 to 28, the polynucleotide according to embodiment 35, the vector according to embodiment 36, and/or the host cell according to embodiment 37; and a pharmaceutically acceptable carrier.
39. A kit comprising an immunogenic polypeptide according to any one of embodiments 1 to 28 and an adjuvant, said adjuvant preferably comprising (i) alum and a toll like receptor 4 (TLR4) antagonist, preferably synthetic monophosphoryl lipid A (MPLA), and/or (ii) a squalene-based oil-in-water nano-emulsion, preferably AddaVax™.
40. A method of vaccinating a subject against HPV infection comprising
  (a) contacting said subject with an immunogenic polypeptide according to any one of embodiments 1 to 28, a polynucleotide according to embodiment 35, a vector according to embodiment 36, and/or a host cell according to embodiment 37, and
  (b) thereby, vaccinating said subject against HPV infection.
41. The method of vaccinating a subject of embodiment 40, further comprising administering an adjuvant, said adjuvant preferably comprising (i) alum and a toll like receptor 4 (TLR4) antagonist, preferably synthetic monophosphoryl lipid A (MPLA), and or (ii) a squalene-based oil-in-water nano-emulsion, preferably AddaVax™.
42. A method for producing antibodies against an HPV L2 polypeptide, comprising
  (a) contacting a subject with an immunogenic polypeptide according to any one of embodiments 1 to 28, a polynucleotide according to embodiment 35, a vector according to embodiment 36, and/or a host cell according to embodiment 37, and
  (b) harvesting antibodies generated by said subject from a bodily fluid of said subject and/or harvesting cells producing said antibodies from said subject.

All references cited in this specification are herewith incorporated by reference with respect to their entire disclosure content and the disclosure content specifically mentioned in this specification.

FIGURE LEGENDS

FIG. 1: Induction of neutralizing antibody titers by various immunogenic polypeptides comprising Padre sequences in mice; heteromeric PfTrx-8mer and PfTrx-11mer constructs were compared to a mixture of PfTrx-homotrimers (Mix 16/18/51). Panels show titers of neutralizing titers measured in mice against A) HPV16, B) HPV18, C) HPV31, D) HPV45, E) HPV33, F) HPV51, G) HPV35, H) HPV52, and I) HPV58; each value indicated represents one mouse, horizontal lines indicate mean values.

Figure 2:
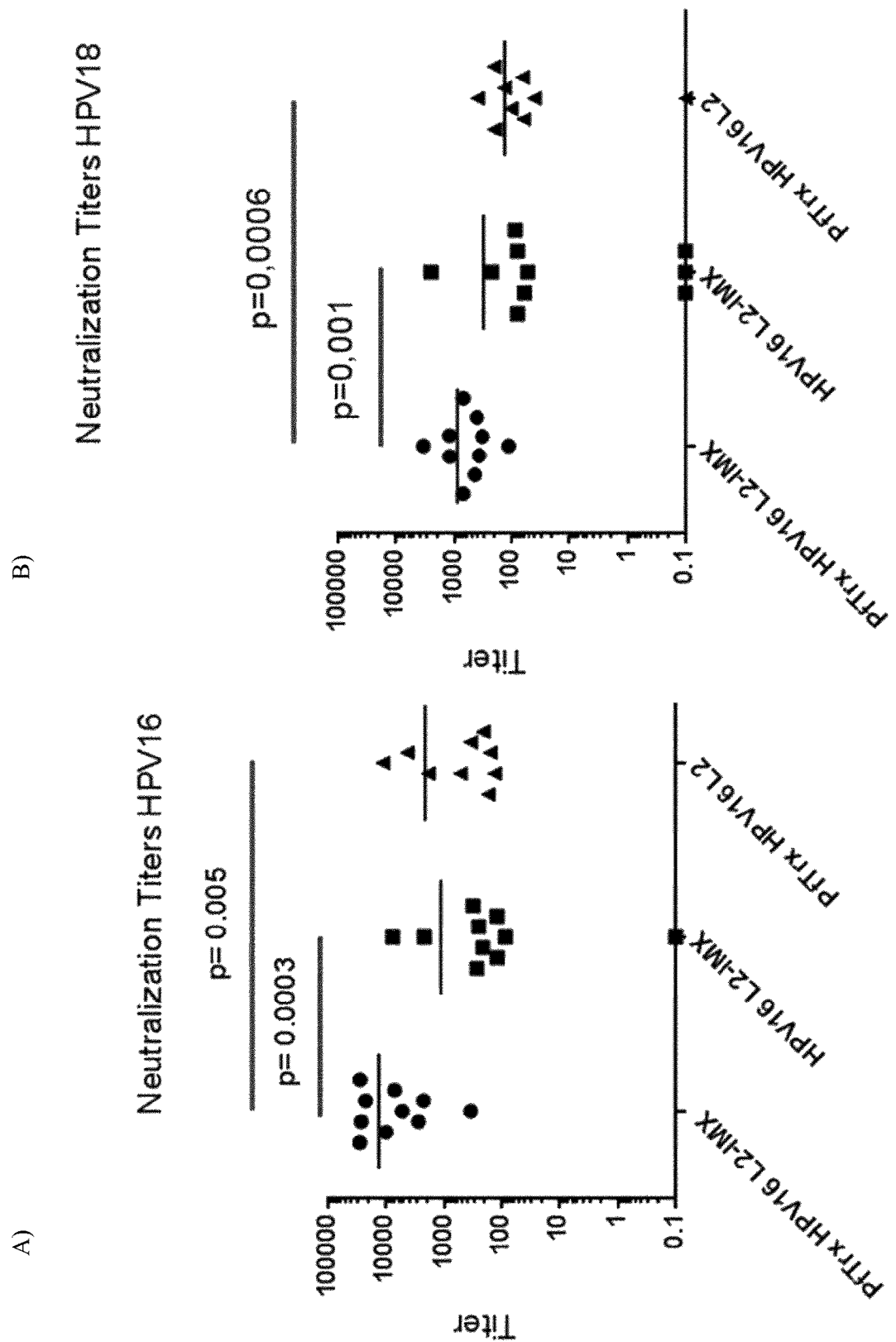
Figure 2:
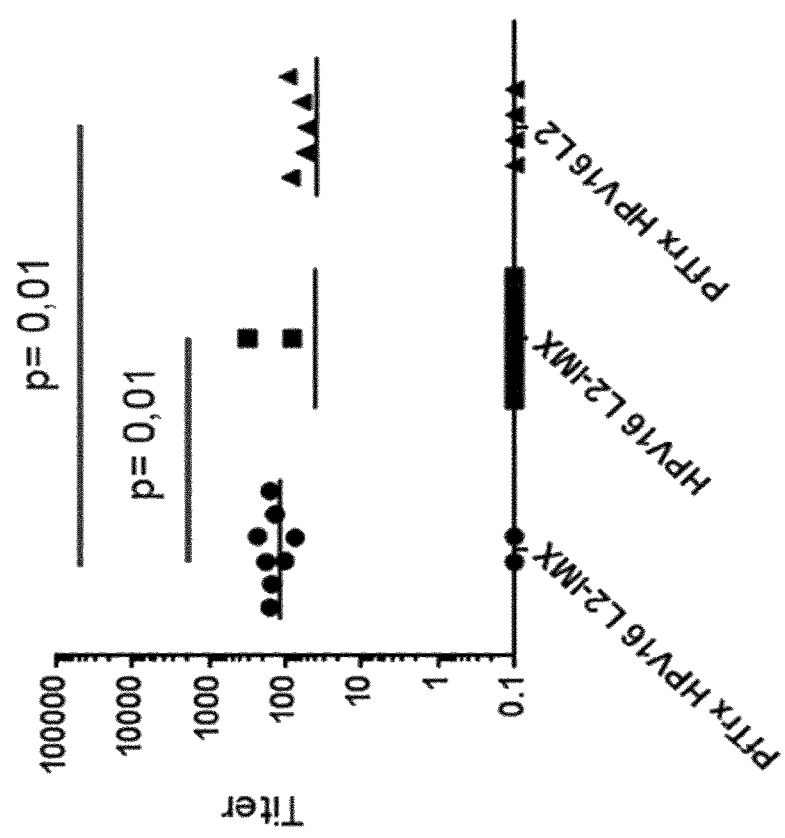

FIG. 2: Induction of neutralizing antibody titers by various immunogenic polypeptides comprising IMX sequences in mice; a homotrimeric HPV16 L2 N-terminal peptide was used as an IMX-fusion, as a PfTrx-fusion, or as a fusion protein containing both IMX and PfTrx. Panels show titers of neutralizing titers measured in mice against A) HPV16, B) HPV18, and C) HPV45; each value indicated represents one mouse, horizontal lines indicate mean values.

FIG. 3: Comparison of adjuvants. PfTrx containing homotrimeric HPV16 L2 N-terminal peptide and further comprising IMX or not was used as an antigen (Trx-L2-IMX, pfTrx-L2-IMX and Trx-L2), A) and B). Moreover, the constructs were compared to mixed 8mer and 11mer constructs, C) to G)). Panels show titers of neutralizing titers measured in 9 to 10 mice against A) HPV16, B) HPV18; C) HPV16, D) HPV18, E) HPV33, F) HPV51, and G) HPV58. A/M: Alum/MPLA; each value indicated represents one mouse, horizontal lines indicate mean values.

FIG. 4: Induction of neutralizing antibody titers by various immunogenic polypeptides comprising IMX sequences in mice; a homotrimeric HPV16 L2 N-terminal peptide was compared to heteromeric PfTrx-8mer and PfTrx-11mer constructs. Panels show titers of neutralizing titers measured in mice against A) HPV16, B) HPV18, C) HPV31, D) HPV33, E) HPV35, F) HPV39, G) HPV45, H) HPV51, I) HPV52, and K) HPV58; each value indicated represents one mouse, horizontal lines indicate mean values.

FIG. 5: Induction of neutralizing antibody titers by various immunogenic polypeptides as indicated. Panels show titers of neutralizing titers measured in mice against A) HPV16, B) HPV18, C) HPV31, D) HPV33, E) HPV35, F) HPV39, G) HPV45, H) HPV51, I) HPV52, and K) HPV58; each value indicated represents one mouse, horizontal lines indicate mean values.

FIG. 6: Amino acid sequences of immunogenic polypeptides according to the invention: A) 11mer heteromeric polypeptide (SEQ ID NO: 25), B) 8mer heteromeric polypeptide (SEQ ID NO: 26), C) 11mer heteromeric polypeptide comprised in P. furiosus thioredoxin (SEQ ID NO: 27, A) 11mer heteromeric polypeptide comprised in P. furiosus thioredoxin (SEQ ID NO: 29).

Figure 7:
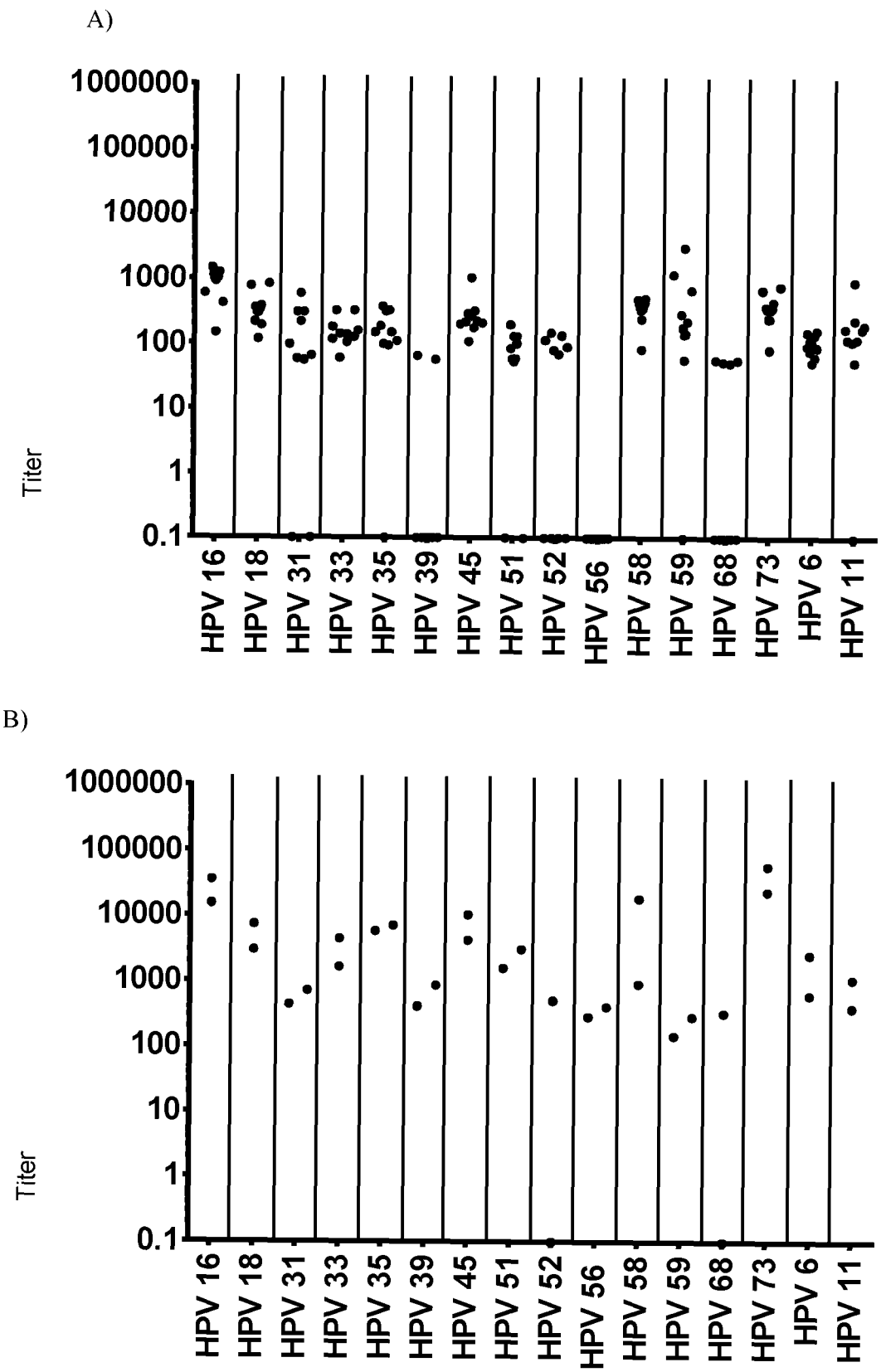

FIG. 7: Neutralization titers of sera from mice (N=10; A)) and guinea pigs (N=2; B)) in a pseudovirion-based neutralization assay (PBNA); the antigen used was PfTrx 8mer-IMX3T3 (SEQ ID NO:43); each dot represents a value obtained with serum from one animal.

FIG. 8: Neutralization titers of sera from mice (N=10; A)) and guinea pigs (N=2; B)) in an L2-enhanced pseudovirion-based neutralization assay (L2-PBNA); the antigen used was PfTrx 8mer-IMX3T3 (SEQ ID NO:43); each dot represents a value obtained with serum from one animal.

The following Examples shall merely illustrate the invention. They shall not be construed, whatsoever, to limit the scope of the invention.

EXAMPLE 1: GENERATION OF IMMUNOGENS AND IMMUNIZATION

In the experiments, various constructs were used: The PfTrx8mer is a P. furiosus thioredoxin with HPV L2 N-terminal peptides corresponding to amino acids 20 to 38 of the L2 polypeptide of HPV16 in the sequence HPV 16-18-31-33-35-6-51-59; the PfTrx 11mer is a P. furiosus thioredoxin with HPV L2 N-terminal peptides corresponding to amino acids 20 to 38 of the L2 polypeptide of HPV16 in the sequence HPV 16-18-31-33-35-39-45-51-56-59-82. The term Mix 16/31/51 relates to a mixture of P. furiosus thioredoxins comprising three HPV16 L2 N-terminal identical peptides corresponding to amino acids 20 to 38 of the L2 polypeptide of HPV16 derived from HPV16, HPV31, and HPV51, respectively. Immunogens comprising the designation "Padre" comprised an additional Padre sequence, immunogens comprising the designation "imx" comprised an additional imx domain. For comparison, corresponding constructs comprising homotrimeric or monomeric HPV16 L2 N-terminal peptides were used (SEQ ID NOs: 62 to 81).

Constructs as indicated were obtained by standard recombinant DNA techniques and molecular cloning according to methods known from textbooks, followed by production in E. coli and purification as described herein below. Immunogenic polypeptides were obtained essentially as described earlier (WO 2010/070052), and as described herein below.

6-8-weeks-old female BALB/c mice were purchased from Charles River Laboratories and were kept in an animal facility under specific pathogen-free conditions. Mice were immunized intramuscularly four times at biweekly intervals with antigens mixed with adjuvants. For the Alum/MPLA experiment 20 µg of the antigen adjuvanted with 50 µg aluminium hydroxide (Brenntag) and 10 µg synthetic monophosphoryl lipid A (MPLA, AvantiLipids). In case of Montanide ISA720 (Seppic, France) and Addavax™ (InvivoGen), 20 µg of the antigen was mixed with 50% V/V of an adjuvant. Guinea pigs were immunized according to standard protocols.

EXAMPLE 2: PSEUDOVIRION-BASED NEUTRALIZATION ASSAYS

Pseudovirion-based neutralization assays (PBNAs) were performed essentially as described in WO 2011/151335. Briefly, 50 µl of diluted serum was combined with 50 µl of diluted pseudovirion and incubated at room temperature for 20 min. Next, 50 µl of HeLa T cells ($2.5 \times 10^5$ cells/ml) was added to the pseudovirion-antibody mixture and incubated for 48 h at 37° C. humidified incubator. The amount of secreted Gaussia luciferase was determined in 10 µl of cell culture medium using the Gaussia glow juice kit (PJK, Germany) according to the manufacturer's instructions. The light emissions of samples were measured 15 minutes after substrate addition.

For the L2-enhanced pseudovirion-based neutralization assay (L2-PBNA), which has essentially the same sensitivity for anti-L1 antibodies, but a strongly increased sensitivity to anti-L2 antibodies, the PBNA was modified essentially as described in Day et al. (2012), Clinical and Vaccine Immunology 19(7):1075. Briefly, in the L2-PBNA, HPV pseudovirions are bound to extracellular matrix and treated with furin, which causes better exposure of L2. Only after this treatment, the actual PBNA is performed. Results of the L2-PBNA with mouse and guinea pig sera are shown in FIG. 8.

EXAMPLE 3: IMX-TRX-L2(20-38)8-MER VACCINE PRODUCTION AND PURIFICATION

Standard procedures were used for bacterial transformation and IPTG-mediated induction (overnight at 30° C.) of recombinant antigen expression. Following sonication-lysis of induced bacterial cells, recovery of the soluble fraction by centrifugation (10,000×g, 15 min), one freezing/thawing cycle applied to the supernatant and an additional centrifugation step as above, the solubilized bacterial lysate was loaded onto a heparin-affinity chromatography column (Hi-Trap Heparin, GE Healthcare equilibrated in 25 mM Tris-HCl, pH 7.5, 100 mM NaCl at a flow of 1.0 ml/min. In a typical medium-scale preparation, 50 ml of soluble lysate, derived from a 500 ml bacterial culture, were applied to a 1 ml Hi-Trap Heparin column, which was eluted with a 30 ml, 0.1 M-2.0 M NaCl linear gradient in starting buffer. As revealed by SDS-PAGE analysis of the eluted protein (native MW: 248,339; subunit MW: 35,477), heparin-affinity fractionation afforded a nearly 90% antigen purification in a single step. When necessary, further purification (practically to a near-homogeneity, 100% level) was achieved by gel filtration chromatography on a Superdex 200 column (24 ml; GE Healthcare) equilibrated and run in 25 mM Tris/HCl-150 mM NaCl at a flow-rate of 0.7 ml/min.

The invention claimed is:

1. An immunogenic polypeptide comprising a multitude of human papillomavirus (HPV) L2 N-terminal peptides consisting of amino acids corresponding to amino acids 20 to 38 of the L2 polypeptide of HPV16, wherein said HPV L2 N-terminal peptides are L2 N-terminal peptides from at least four different HPV genotypes; or are variants thereof comprising at most two amino acid substitutions per HPV L2 N-terminal peptide; and wherein (a) said multitude HPV L2 N-terminal peptides comprises SEP ID NO: 25 or 26 or is a variant of said immunogenic polypeptide comprising at most two amino acid substitutions per HPV L2 N-terminal peptide or (b) the immunogenic polypeptide comprises:
   (i) the amino acid sequence of SEP ID NO: 27, preferably encoded by a polynucleotide comprising the nucleic acid sequence of SEP ID NO: 28;
   (ii) the amino acid sequence of SEP ID NO: 29;
   (iii) the amino acid sequence of SEP ID NO: 31;
   (iv) the amino acid sequence of SEP ID NO: 33;
   (v) the amino acid sequence of SEP ID NO: 34;
   (vi) the amino acid sequence of SEP ID NO: 36;
   (vii) the amino acid sequence of SEP ID NO: 38;
   (viii) the amino acid sequence of SEP ID NO: 39;
   (ix) the amino acid sequence of SEP ID NO: 41; or
   (x) the amino acid sequence of SEP ID NO: 43.

2. The immunogenic polypeptide of claim 1, wherein said multitude is a number of from 5 to 10.

3. The immunogenic polypeptide of claim 1, wherein said HPV L2 N-terminal peptides are L2 N-terminal peptides from at least five different HPV genotypes.

4. The immunogenic polypeptide of claim 1, wherein said immunogenic polypeptide comprises said HPV L2 N-terminal peptides in the sequence HPV 16-18-31-33-35-39-45-51-56-59-82.

5. The immunogenic polypeptide of claim 1, further comprising an oligomerization domain.

6. The immunogenic polypeptide of claim 1, wherein said immunogenic polypeptide further comprises an enhancer of immunogenicity.

7. The immunogenic polypeptide of claim 1, wherein said multitude of HPV L2 N-terminal peptides is comprised in a thioredoxin polypeptide.

8. A polynucleotide encoding the immunogenic polypeptide according to claim 1.

9. The immunogenic polypeptide of claim 5, wherein said oligomerization domain is at least one of
   (i) an oligomerization domain of a C4-binding protein;
   (ii) an encapsulin polypeptide;
   (iii) a ferritin polypeptide; and
   (iv) a hybrid polypeptide of two different chicken C4-binding proteins.

10. The immunogenic polypeptide of claim 5, wherein said oligomerization domain is an IMX3T3 polypeptide.

11. A method of vaccinating a subject against HPV infection comprising
   (a) contacting said subject with an immunogenic polypeptide according to claim 1, and
   (b) thereby, vaccinating said subject against HPV infection.

12. The method of claim 11, wherein said vaccination is vaccination against at least the HPV genotype 6, 16, 18, 31, 33, 35, 51, and 59 infection.

13. The method of claim 11, wherein said vaccination further comprises administering an adjuvant.

14. The method of claim 13, wherein said adjuvant comprises (i) alum and a toll like receptor 4 (TLR4) antagonist, and/or (ii) a squalene-based oil-in-water nano-emulsion.

* * * * *

UNITED STATES PATENT AND TRADEMARK OFFICE
CERTIFICATE OF CORRECTION

PATENT NO. : 10,736,954 B2
APPLICATION NO. : 16/308358
DATED : August 11, 2020
INVENTOR(S) : Angelo Bolchi et al.

Page 1 of 1

It is certified that error appears in the above-identified patent and that said Letters Patent is hereby corrected as shown below:

In the Claims

Claim 1, Column 103, Line 28, replace --HP V16-- with --HPV16--.

Claim 1, Column 103, Line 33, replace --SEP ID NO: 25-- with --SEQ ID NO: 25--.

Claim 1, Column 103, Line 37, replace --SEP ID NO: 27-- with --SEQ ID NO: 27--.

Claim 1, Column 103, Lines 37-39, delete ", preferably encoded by a polynucleotide comprising the nucleic acid sequence of SEP ID NO: 28".

Claim 1, Column 103, Line 40, replace --SEP ID NO: 29-- with --SEQ ID NO: 29--.

Claim 1, Column 103, Line 41, replace --SEP ID NO: 31-- with --SEQ ID NO: 31--.

Claim 1, Column 103, Line 42, replace --SEP ID NO: 33-- with --SEQ ID NO: 33--.

Claim 1, Column 103, Line 43, replace --SEP ID NO: 34-- with --SEQ ID NO: 34--.

Claim 1, Column 103, Line 44, replace --SEP ID NO: 36-- with --SEQ ID NO: 36--.

Claim 1, Column 103, Line 45, replace --SEP ID NO: 38-- with --SEQ ID NO: 38--.

Claim 1, Column 103, Line 46, replace --SEP ID NO: 39-- with --SEQ ID NO: 39--.

Claim 1, Column 103, Line 47, replace --SEP ID NO: 41-- with --SEQ ID NO: 41--.

Claim 1, Column 103, Line 48, replace --SEP ID NO: 43-- with --SEQ ID NO: 43--.

Signed and Sealed this
Twenty-ninth Day of March, 2022

Drew Hirshfeld
*Performing the Functions and Duties of the
Under Secretary of Commerce for Intellectual Property and
Director of the United States Patent and Trademark Office*